United States Patent
Pellicciari et al.

(10) Patent No.: US 7,932,244 B2
(45) Date of Patent: Apr. 26, 2011

(54) BILE ACID DERIVATIVES AS FXR LIGANDS FOR THE PREVENTION OR TREATMENT OF FXR-MEDIATED DISEASES OR CONDITIONS

(75) Inventors: Roberto Pellicciari, Perugia (IT); Stefano Fiorucci, Perugia (IT); Mark Pruzanski, New York, NY (US)

(73) Assignee: Intercept Pharmaceuticals, Inc., New York, NY (US)

( * ) Notice: Subject to any disclaimer, the term of this patent is extended or adjusted under 35 U.S.C. 154(b) by 737 days.

(21) Appl. No.: 11/819,517

(22) Filed: Jun. 27, 2007

(65) Prior Publication Data
US 2008/0182832 A1 Jul. 31, 2008

Related U.S. Application Data

(60) Provisional application No. 60/816,635, filed on Jun. 27, 2006.

(51) Int. Cl.
*A61K 31/575* (2006.01)
*C07C 9/00* (2006.01)

(52) U.S. Cl. ........................ 514/182; 552/553

(58) Field of Classification Search .............. 552/553; 514/182
See application file for complete search history.

(56) References Cited

U.S. PATENT DOCUMENTS

| | | | |
|---|---|---|---|
| 5,014,206 | A | 5/1991 | Scribner et al. |
| 5,121,853 | A | 6/1992 | Edelhoff et al. |
| 5,326,939 | A | 7/1994 | Schafer et al. |
| 5,392,926 | A | 2/1995 | Schafer et al. |
| 5,565,846 | A | 10/1996 | Geiszler et al. |
| 6,191,691 | B1 | 2/2001 | Serrault et al. |
| 6,448,898 | B1 | 9/2002 | Kasik |
| 7,078,396 | B2 | 7/2006 | Song et al. |
| 7,138,390 | B2 | 11/2006 | Pellicciari et al. |
| 2003/0112155 | A1 | 6/2003 | Landre et al. |
| 2004/0027243 | A1 | 12/2004 | Carrender |

FOREIGN PATENT DOCUMENTS

| | | |
|---|---|---|
| EP | 1392714 | 3/2004 |
| EP | 1568706 | 8/2005 |
| WO | WO-00/37077 | 6/2000 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
International Search Report for Application No. PCT/US07/14829 dated Dec. 12, 2007.
Fiorucci, S., et al., Gastroenterology (2004).
Forman, BM. et al., Cell 81:687-693 (1995).
Mangelsdorf, DJ., et al., Cell 83:841-850 (1995).
Pellicciari, R., et al., J. Med Chem. 15;45:3569-72 (2002).
Seol, W., et al., Mol. Endocrinnol. 9:72-85 (1995).
Russell, DW, Cell 97:539-542 (1999).

* cited by examiner

*Primary Examiner* — Barbara P Badio
(74) *Attorney, Agent, or Firm* — Mintz, Levin, Cohn, Ferris, Glovsky, and Popeo, P.C.; Ivor R. Elrifi, Esq.; Jennifer L. Loebach, Esq.

(57) ABSTRACT

The present invention relates to compounds of formula (I):

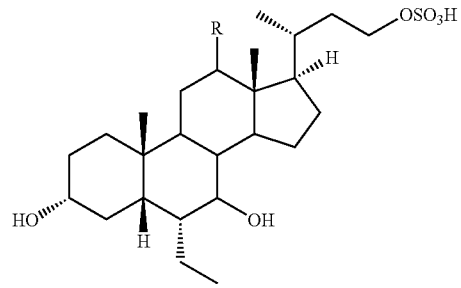

wherein R is hydrogen or alpha-hydroxy,
the hydroxyl group in position 7 is in the alpha or beta position;
and pharmaceutically acceptable salts, solvates or amino acid conjugates thereof.

8 Claims, 48 Drawing Sheets

BILE ACID DERIVATIVES AS FXR LIGANDS FOR THE PREVENTION OR TREATMENT OF FXR-MEDIATED DISEASES OR CONDITIONS

FIELD OF THE INVENTION

The present invention relates to Farnesoid X receptor (FXR) modulators which can be used for the treatment of cholestatic disorders, in particular to bile acid derivatives wherein the $C_6$ contains an ethyl and the $C_{24}$ carboxy group is transformed into a sulphate group.

BACKGROUND OF THE INVENTION

Farnesoid X Receptor (FXR) is an orphan nuclear receptor initially identified from a rat liver cDNA library (B M. Forman, et al., Cell 81:687-693 (1995)) that is most closely related to the insect ecdysone receptor. FXR is a member of the nuclear receptor family of ligand-activated transcription factors that includes receptors for the steroid, retinoid, and thyroid hormones (D J. Mangelsdorf, et al., Cell 83:841-850 (1995)). Northern and in situ analysis show that FXR is most abundantly expressed in the liver, intestine, kidney, and adrenal (B M. Forman, et al., Cell 81:687-693 (1995) and W. Seol, et al., Mol. Endocrinnol. 9:72-85 (1995)). FXR binds to DNA as a heterodimer with the 9-cis retinoic acid receptor (RXR). The FXR/RXR heterodimer preferentially binds to response elements composed of two nuclear receptor half sites of the consensus AG(G/T)TCA organized as an inverted repeat and separated by a single nucleotide (IR-1 motif) (B M. Forman, et al., Cell 81:687-693 (1995)). An early report showed that rat FXR is activated by micromolar concentrations of farnesoids such as farnesol and juvenile hormone (B M. Forman, et al., Cell 81:687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published 29 Jun. 2000)). As discussed therein, the bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: bile acids down-regulate the transcription of cytochrome P450 7a (CYP7a), which encodes the enzyme that catalyzes the rate limiting step in bile acid biosynthesis. There is data to suggest that FXR is involved in the repression of CYP7a expression by bile acids, although the precise mechanism remains unclear (D W. Russell, Cell 97:539-542 (1999)). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters. Thus FXR is involved in both the stimulation (IBABP) and the repression (CYP7a) of target genes involved in bile acid and cholesterol homeostasis.

EP 1392714 discloses 3α,7α-dihydroxy-6α-ethyl-5β-cholan-24-oic acid (hereinafter also referred to as 6-ethyl-chenodeoxycholic acid, 6-EDCA), solvates and amino acids conjugates thereof as FXR agonists, which can be used in the preparation of medicaments for the prevention or treatment of FXR-mediated diseases or conditions.

EP 1568796 discloses 6-ethyl-ursodeoxycholic acid (6-EUDCA) derivatives as FXR agonists and their use in the prevention or treatment of FXR-mediated diseases or conditions.

BRIEF SUMMARY OF THE INVENTION

According to a first aspect, the present invention provides compounds of formula (I):

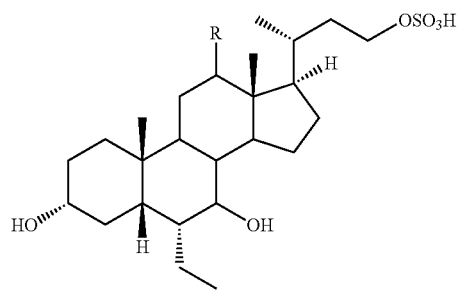

wherein R is hydrogen or alpha-hydroxy, the hydroxyl group in position 7 is in the alpha or beta position;

and pharmaceutically acceptable salts, solvates or amino acid conjugates thereof.

In one embodiment, the compound of formula (I) is in the form of a chenodeoxycholic acid derivative. In another embodiment, the compound of formula (I) is in the form of a ursodeoxycholic acid derivative. In still another embodiment, the compound of formula (I) is in the form of a cholic acid derivative.

In another embodiment, the compound of formula (I) is in the form of a triethyl ammonium salt:

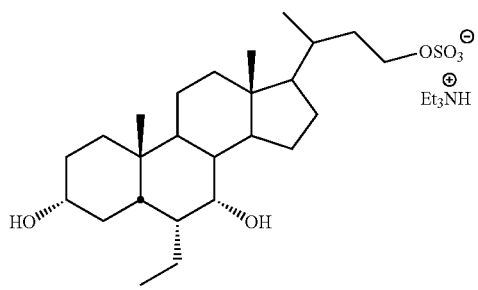

6. In another embodiment, the compound of formula (I) is in the form of a sodium salt:

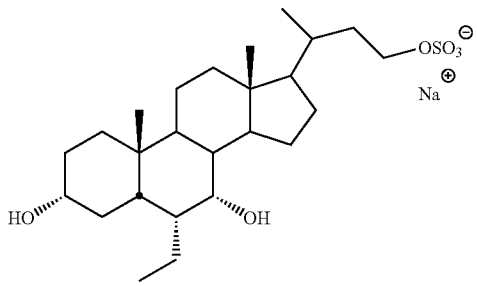

In another aspect, the present invention provides a method for the prevention or treatment of an FXR mediated disease or condition. The method comprises administering a therapeutically effective amount of a compound of formula (I). The present invention also provides the use of a compound of formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesteremia, or hyperlipidemiachronic liver disease, gastrointestinal disease, renal disease, cardiovascular disease, metabolic disease, cancer (i.e., colorectal cancer), or neurological indications such as stroke. In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extra-hepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis. In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease. In certain embodiments, the cardiovascular disease is atherosclerosis, arteriosclerosis, dyslipidemia, hypercholesterolemia, or hypertriglyceridemia. In certain embodiments, the metabolic disease is insulin resistance, Type I and Type II diabetes, or obesity.

In another aspect, the present invention provides a pharmaceutical composition comprising a compound of formula (I) and a pharmaceutically acceptable carrier or diluent.

In another aspect, the present invention provides a process for preparing a compound of formula (I) and pharmaceutically acceptable salts, solvates or amino acid conjugates thereof.

DETAILED DESCRIPTION OF THE INVENTION

Figure 1:
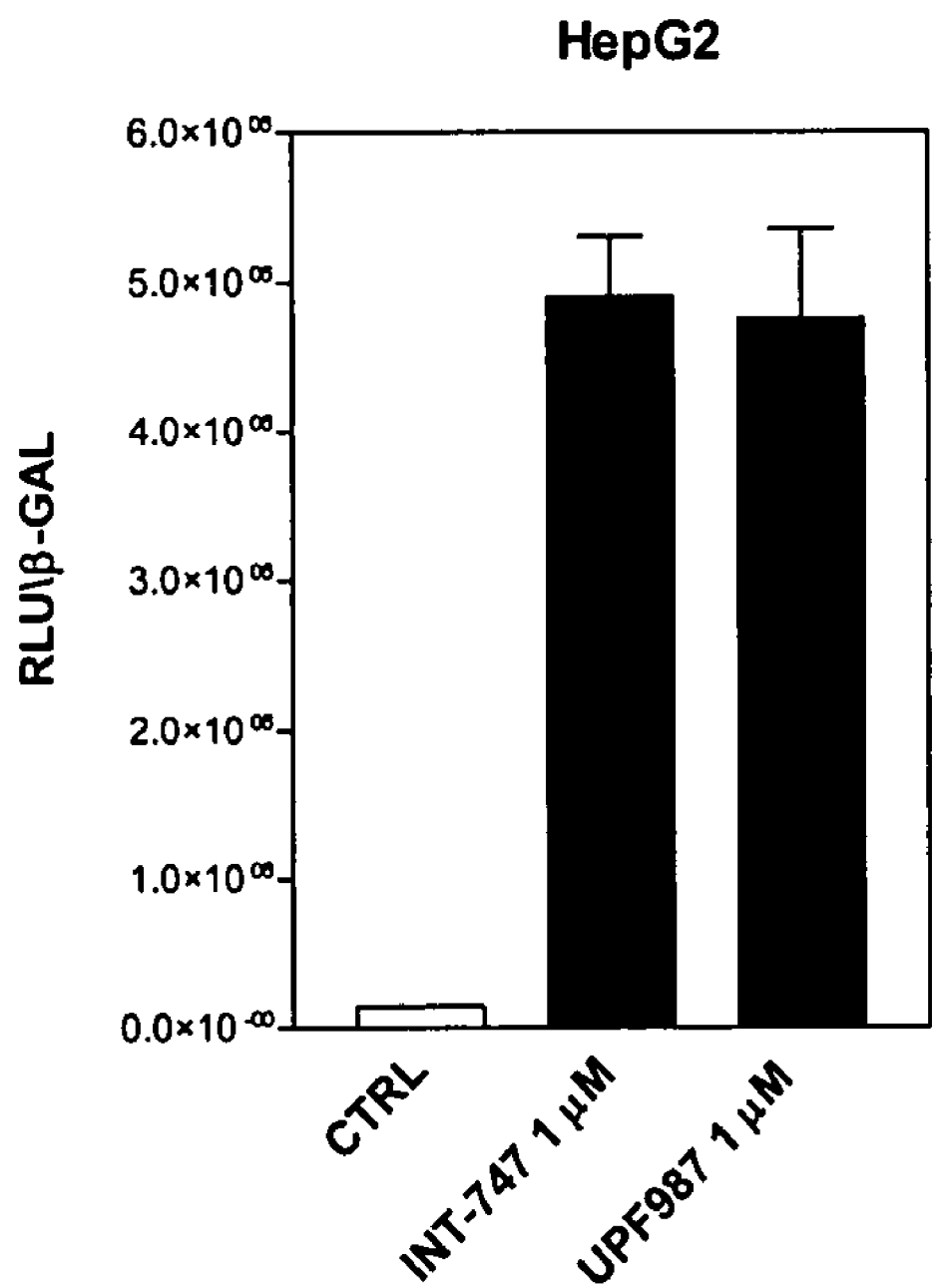
FIG. 1 shows the transactivation assay result in a graph format. Each data point is the average of triplicate assays. CTRL: control; INT-747: 6-ECDCA; UPF-987.
Figure 2:
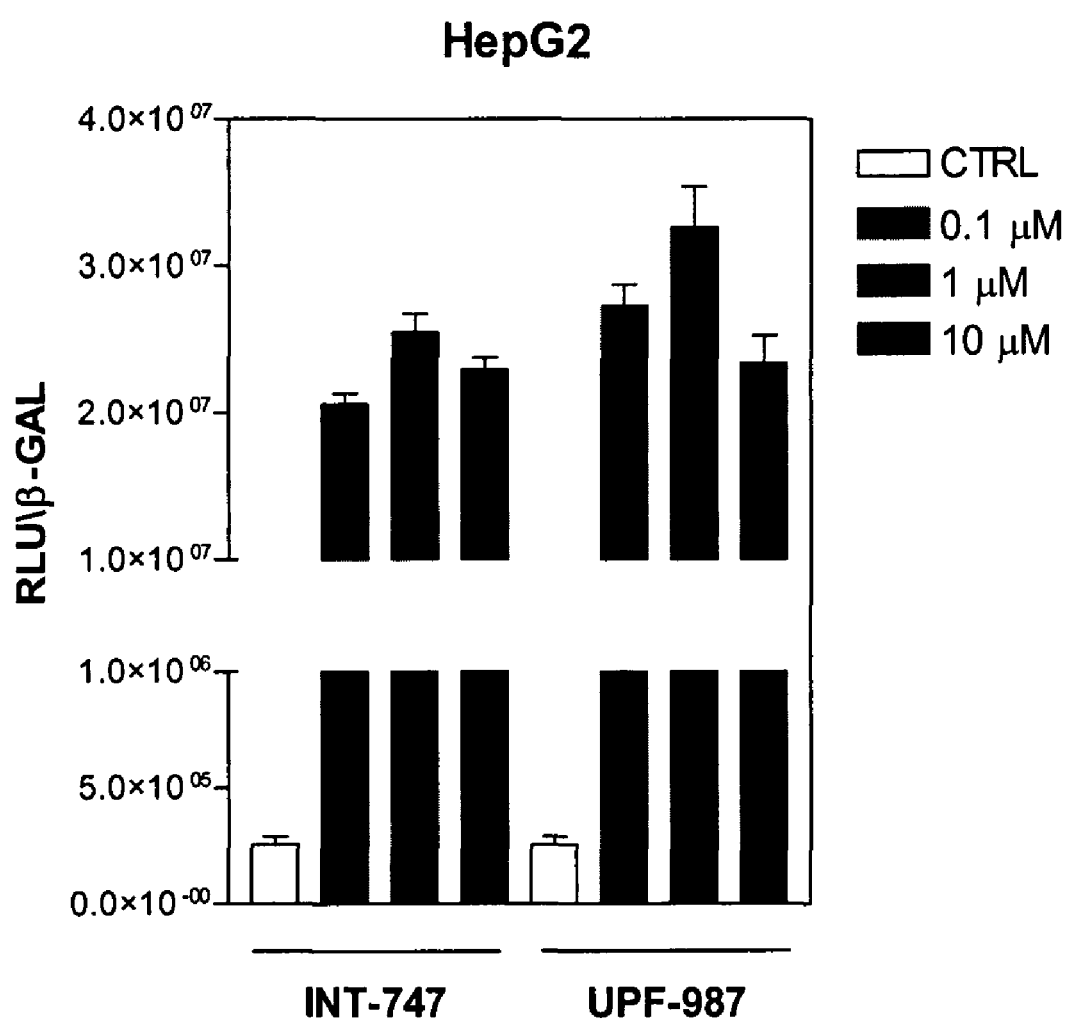
FIG. 2 shows the dose response of INT-747 and UPF-987 in the transactivation assay.

The present invention relates to compounds of general formula (I):

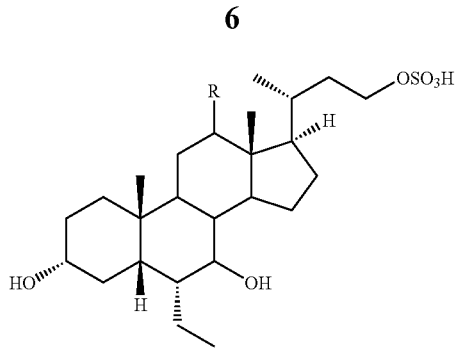

wherein R is hydrogen or alpha-hydroxy,
the hydroxyl group in position 7 is in the alpha or beta position;
and pharmaceutically acceptable salts, solvates or amino acid conjugates thereof.

Suitable pharmaceutically acceptable salts according to the present invention will be readily determined by one skilled in the art and will include, for example, basic salts such as alkali or alkaline-earth metallic salts made from aluminium, calcium, lithium, magnesium, potassium, sodium, and zinc or organic salts made from N,N'-dibenzylethylenediamine, chlorprocaine, choline, diethanolamine, ethylendiamine, meglumine (N-methylglucamine), and procaine. Salts with pharmaceutically acceptable amines such as lysine, arginine, tromethamine, triethylamine and the like can also be used. Such salts of the compounds of formula (I) may be prepared using conventional techniques, from the compound of Formula (I) by reacting, for example, the appropriate base with the compound of Formula (I).

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" is a crystal form containing the compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

As used herein, the term "amino acid conjugates" refers to conjugates of the compounds of formula (I) with any suitable amino acid. Preferably, such suitable amino acid conjugates of the compounds of formula (I) will have the added advantage of enhanced integrity in bile or intestinal fluids. Suitable amino acids include but are not limited to glycine and taurine. Thus, the present invention encompasses the glycine and taurine conjugates of any of the compounds of formula (I).

In one embodiment, the compound of formula I is a chenodeoxycholic acid derivative, wherein the hydroxyl group in 7 is in the alpha position and R is hydrogen.

In another embodiment, the compound of formula I is a ursodeoxycholic acid derivative, wherein the hydroxyl group in 7 is in the beta position and R is hydrogen.

In another embodiment, the compound of formula I is a cholic acid derivative, wherein the hydroxyl group in 7 is in the alpha position and R is alpha-hydroxy.

Hereinafter all references to "compounds of formula (I)" refer to compounds of formula (I) as described above together with their and pharmaceutically acceptable salts, solvates or amino acid conjugates thereof.

The compounds of formula I may be prepared starting from the 6-ethyl-7-keto-cholic acids, prepared as disclosed in EP 1392714 and EP 1568796, suitably protected at the 3-hydroxy moiety, by a reaction sequence comprising the transformation of the C24 carboxy group into a iodine atom, the conversion of the latter into an hydroxyl group, reduction of the 7-keto group to give the corresponding 3-alpha or 3-beta hydroxyl group, the selective sulfonylation of the C24 hydroxy group and the deprotection of the 3-hydroxy group.

The reaction scheme and the reagents used in each step are reported in the following scheme showing the preparation of 3α,7α,23-trihydroxy-6α-ethyl-24-nor-5β-cholan-23-sulphate in the form of triethylammonium salt (UPF-987 or compound (9) below). The same scheme may be adapted, by suitably substituting the reagents and/or starting materials and optionally by also changing reaction sequences and protective groups, for the preparation of other compounds of formula I.

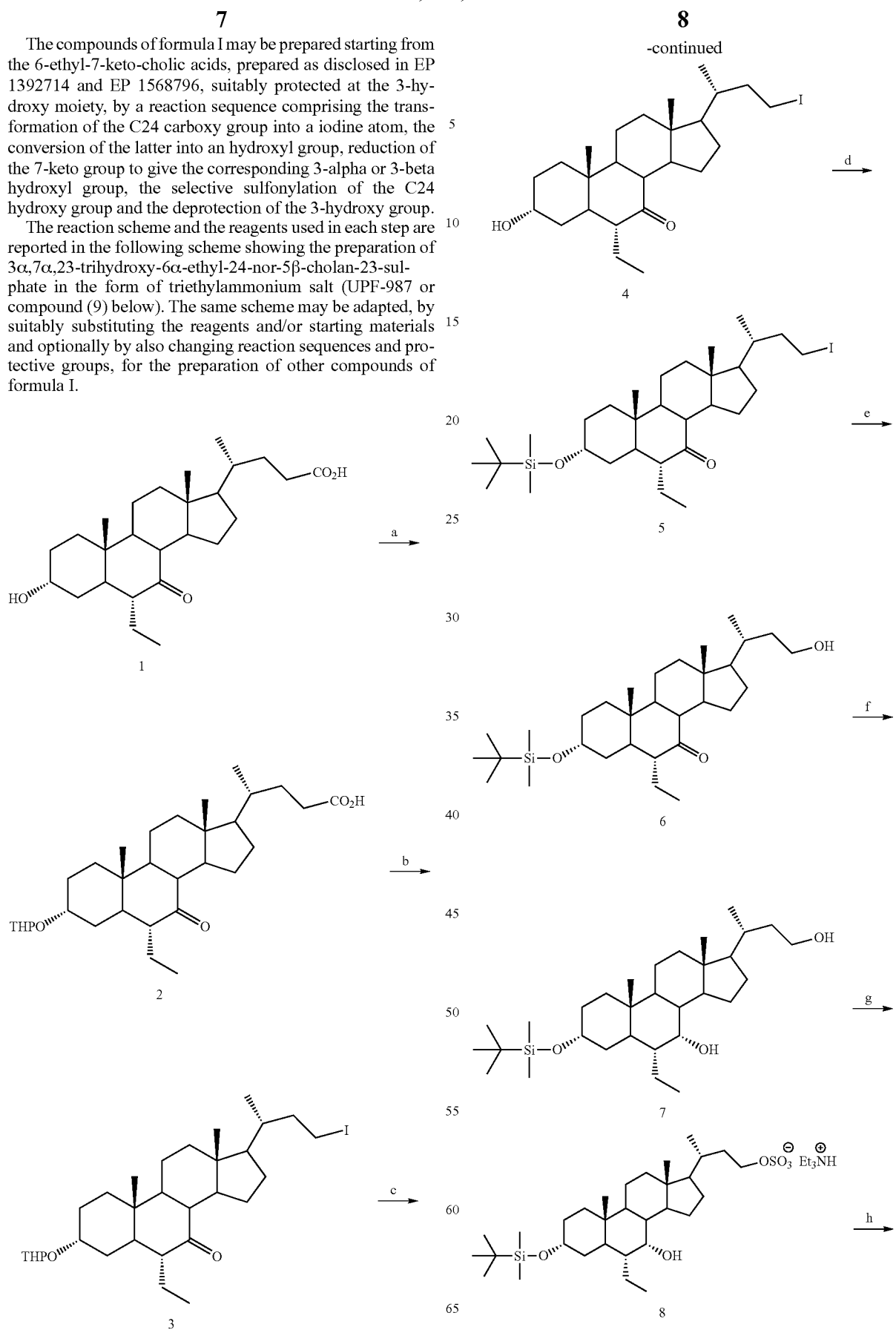

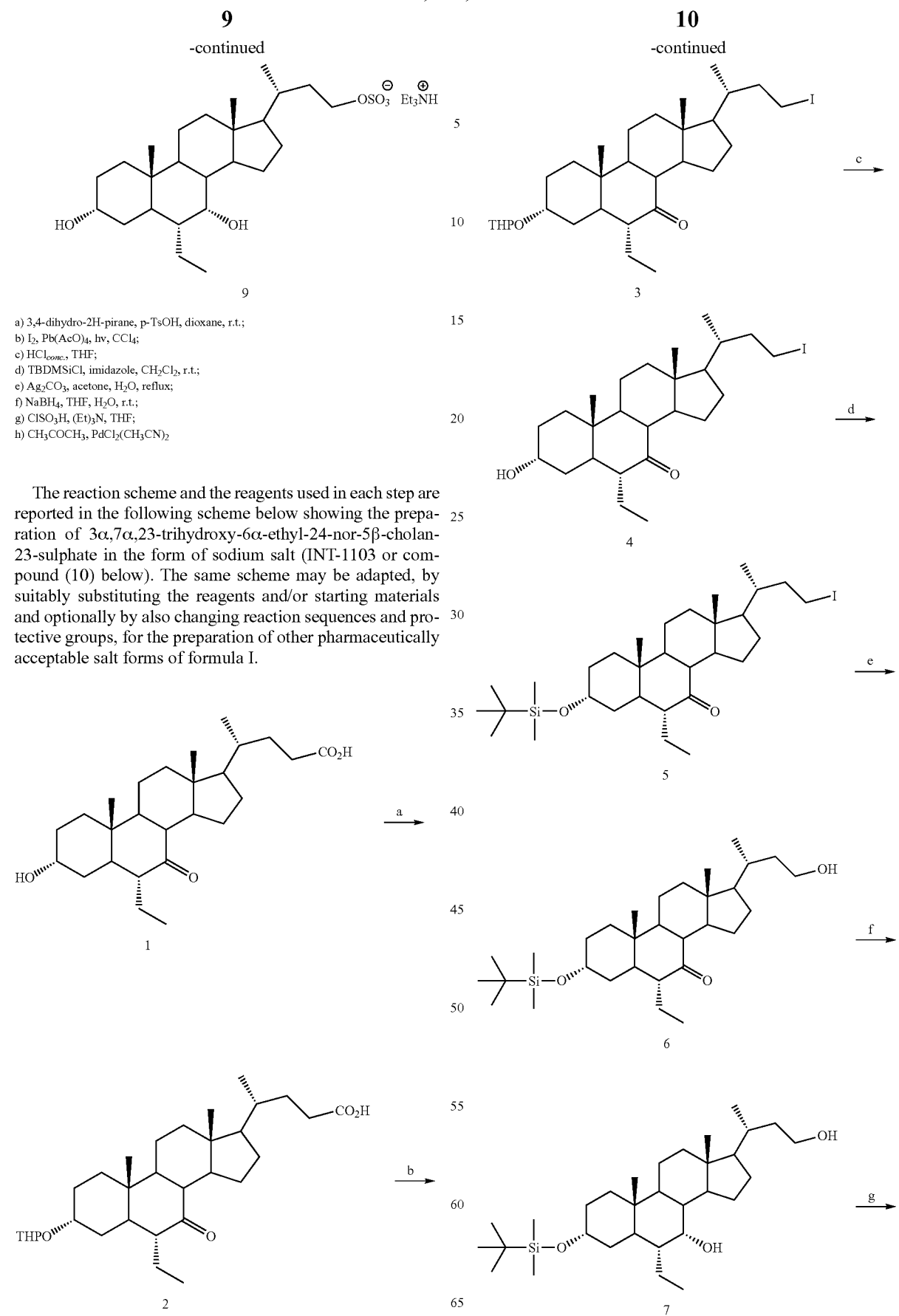

a) 3,4-dihydro-2H-pirane, p-TsOH, dioxane, r.t.;
b) I$_2$, Pb(AcO)$_4$, hv, CCl$_4$;
c) HCl$_{conc.}$, THF;
d) TBDMSiCl, imidazole, CH$_2$Cl$_2$, r.t.;
e) Ag$_2$CO$_3$, acetone, H$_2$O, reflux;
f) NaBH$_4$, THF, H$_2$O, r.t.;
g) ClSO$_3$H, (Et)$_3$N, THF;
h) CH$_3$COCH$_3$, PdCl$_2$(CH$_3$CN)$_2$ The reaction scheme and the reagents used in each step are reported in the following scheme below showing the preparation of 3α,7α,23-trihydroxy-6α-ethyl-24-nor-5β-cholan-23-sulphate in the form of sodium salt (INT-1103 or compound (10) below). The same scheme may be adapted, by suitably substituting the reagents and/or starting materials and optionally by also changing reaction sequences and protective groups, for the preparation of other pharmaceutically acceptable salt forms of formula I.

-continued

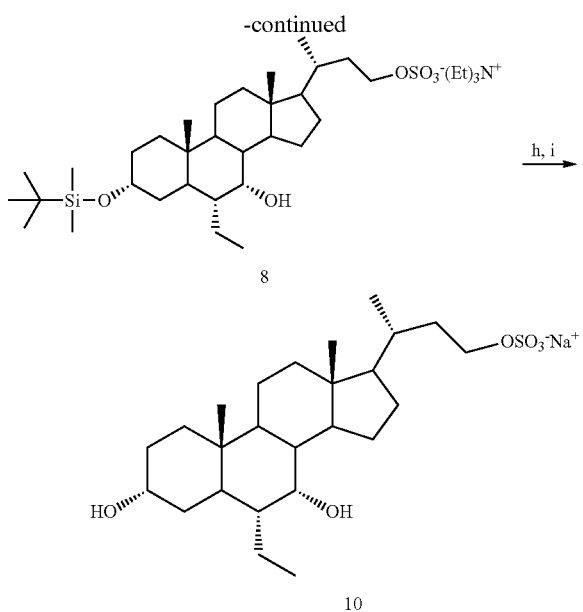

a) 3,4 dihydro-2H-pyrane, p-TsOH, dioxane, t.a.;
b) I$_2$, Pb(AcO)$_4$, hv, CCl$_4$;
c) HCl$_{gas}$, DME;
d) TBDMSCl, imidazole, CH$_2$Cl$_2$, t.a.;
e) Ag$_2$CO$_3$, acetone, H$_2$O, reflux;
f) NaBH$_4$, THF, H$_2$O, r.t.;
g) ClSO$_3$H, (Et)$_3$N, THF;
h) H$_2$O, acetone, PdCl$_2$(CH3CN)$_2$,
i) NaOH, MeOH As explained in greater detail in the experimental section, compound 9 was tested in a cell-free assay and transactivation assay in a human hepatocyte cell line and in vivo in intact mice and rats rendered cholestatic by administration of alfa-nafthylsiotiocyanate (ANIT). In the FRET assay, the compound was found to be approximately 1000 fold more potent than chenodeoxycholic acid (CDCA) in activating FXR. In the tranactivation assay Compound 9 caused 2 fold induction of bile acid transporter, BSEP (bile salt export pump) and the small heterodimeric partner (SHP, an atypical nuclear receptor that lacks a DNA-binding domain). Further it potently suppressed Cyp7A1, SREPB-1c and the fatty acid synthase (FAS), thus indicating that FXR activation by the compound of the invention allows selective modulation of genes involved in bile acid synthesis as well as in lipid, cholesterol and glucose metabolism. Therefore, compounds of formula (I) act as selective modulators of the bile acid transporters and increase the flux of biliary acids in the liver; furthermore, they potently regulate genes involved in lipid and cholesterol metabolism and for this reason they can be used for the prevention or treatment of FXR-mediated diseases or conditions, which include chronic liver disease (involving one or more of cholestasis, steatosis, inflammation, fibrosis, and cirrhosis), gastrointestinal disease, renal disease, cardiovascular disease, and metabolic disease. Chronic liver diseases which may be prevented or treated using compounds of formula (I) include but are not limited to primary biliary cirrhosis (PBC), primary sclerosing cholangitis (PSC), cerebrotendinous xanthomatosis (CTX), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency. Gastrointestinal diseases which may be prevented or treated using compounds of formula (I) include but are not limited to inflammatory bowel disease (IBD) (including Crohn's disease and ulcerative colitis), irritable bowel syndrome (IBS), bacterial overgrowth, malabsorption, post-radiation colitis, and microscopic colitis. Renal diseases which may be prevented or treated using compounds of formula (I) include but are not limited to diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease. Cardiovascular diseases which may be prevented or treated using compounds of formula (I) include but are not limited to atherosclerosis, arteriosclerosis, dyslipidemia, hypercholesterolemia, and hypertriglyceridemia. Metabolic diseases which may be prevented or treated using compounds of formula (I) include but are not limited to insulin resistance, Type I and Type II diabetes, and obesity.

The methods of the present invention comprise the step of administering a therapeutically effective amount of a compound of formula (I). As used herein, the term "therapeutically effective amount" refers to an amount of a compound of formula (I) which is sufficient to achieve the stated effect. Accordingly, a therapeutically effective amount of a compound of formula (I) used in a method for the prevention or treatment of FXR mediated diseases or conditions will be an amount sufficient to prevent or treat the FXR mediated disease or condition. Similarly, a therapeutically effective amount of a compound of formula (I) for use in a method for the prophylaxis or treatment of cholestatic liver diseases or increasing bile flow will be an amount sufficient to increase bile flow to the intestine.

The amount of the compound of formula (I) which is required to achieve the desired biological effect will depend on a number of factors such as the use for which it is intended, the means of administration, and the recipient, and will be ultimately at the discretion of the attendant physician or veterinarian. In general, a typical daily dose for the treatment of FXR mediated diseases and conditions, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prophylaxis and treatment of cholestatic liver diseases.

Thus, in a further aspect, the present invention provides pharmaceutical compositions comprising, as active ingredient, a compound of formula (I) together, and/or in admixture, with at least one pharmaceutical carrier or diluent. These pharmaceutical compositions may be used in the prophylaxis and treatment of the foregoing diseases or conditions.

The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of FXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5-10 μm, preferably 1-5 μm, to ensure delivery into the bronchial tree. For nasal administration, a particle size in the range 10-500 μm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

Therefore, according to a further aspect of the present invention, there is provided the use of the compounds of formula (I) in the preparation of medicaments for the prevention or treatment of FXR mediated diseases or conditions.

The invention will be hereinafter illustrated in more detail in the following Examples.

Example 1

Chemistry. Melting points were determined with a Buchi 535 electrothermal apparatus and are uncorrected. NMR spectra were obtained with a Bruker AC 200 MHz spectromer, and the chemical shifts are reported in parts per million (ppm). The abbreviations used are as follows: s, singlet; bs, broad singlet; d, doublet; dd, double doublet; m, multiplet; q, quartet, t, triplet. Flash column chromatography was performed using Merck silica gel 60 (0.040-0.063 mm). TLC was carried out on precoated TLC plates with silica gel 60 F-254 (Merck). Spots were visualized with phosphomolybdate reagent (5% solution in EtOH). The reactions were carried out under a nitrogen atmosphere.

3α-Tetrahydropyranyloxy-7-keto-5β-cholan-24-oic Acid (2)

3,4-dihydro-2H-pyrane (1.74 ml, 19 mmol) in dioxane (12 ml) was dropped slowly to a solution of p-Toluenesulfonic acid (115 mg, 0.6 ml) and 6α-ethyl-7-ketolithocholic acid (5.0 g, 12 mmol) in dioxane (55 ml). The reaction mixture was stirred at room temperature for 2 hours. Water (40 ml) was then added, and the mixture was partially concentrated under vacuum and extracted with EtOAc (4×25 ml). The combined organic fractions were washed with brine (1×50 ml), dried over anhydrous $Na_2SO_4$ and evaporated under vacuum to afford 6 g of compound 2. The crude derivative was used for the next step without further purification.

$^1$H NMR: (200 MHz, $CDCl_3$) δ: 0.68 (3H, s, C-18 Me); 0.8 (3H, t, J=4 Hz, C-26); 0.98 (3H, d, J=6.5, C-21 Me); 1.17 (3H, s, C-19 Me); 3.4-3.7 (4H, m, C-23 $CH_2$, C-6'); 3.8-3.9 (1H, m, C-3); 2.6-2.8 (1H, m, C-6).

$^{13}$C NMR (50.3 MHz, $CDCl_3$) δ: 212.41, 179.42, 54.75, 52.10, 21.79, 18.30, 12.04.

3α-Tetrahydropyranyloxy-7-keto-24-nor-5β-cholan-23-I (3)

Under irradiation with a 300 w tungsten lamp, iodine (5 g, 20 mmol) in $CCl_4$ (75 ml) was added dropwise to a solution of 2 (5.5 g, 11 mmol) and lead tetra-acetate (4.9 g, 11 mmol) in $CCl_4$ (200 ml). The reaction mixture was stirred until the colour was permanent (18 h). The mixture was cooled and filtered on celite. The organic phase was washed with a 5% $Na_2S_2O_3$ solution, 5% NaOH, brine (15 ml), dried over anhydrous $Na_2SO_4$ and evaporated under vacuum. The residue was purified by silica gel flash chromatography using a mixture of light petroleum/EtOAc 95/5 as mobile phase to give 4.6 g of compound 3 (40% yield).

$^1$H NMR: (200 MHz, $CDCl_3$) δ: 0.54 (3H, s, C-18 Me); 0.68 (3H, t, J=7.36 MHz, C-25); 0.79 (3H, d, J=5.2 MHz, C-21); 1.09 (3H, s, C-19); 2.55 (1H, m, C-26); 2.96 (1H, m, C-23); 3.16 (1H, m, C-23); 3.20 (1H, m, C-6'); 3.76 (1H, m, C-6'); 4.59 (1H, m, C-2').

$^{13}$C NMR (50.3 MHz, $CDCl_3$) δ: 212.50, 96.56, 95.99, 74.90, 74.60, 62.63, 54.63, 52.08, 50.78, 50.58, 49.84, 48.91, 43.38, 42.70, 40.11, 38.90, 36.92, 35.81, 34.34, 34.10, 31.07, 30.06, 29.61, 28.26, 27.85, 25.97, 25.42, 24.54, 23.49, 21.75, 19.76, 19.59, 18.88, 17.84, 12.05, 11.98, 5.26.

3α-hydroxy-6α-ethyl-7-keto-24-nor-5β-cholan-23-I (4)

The compound 3 (2.2 g, 3.8 mmol) was stirred in a solution of HCl 37% in THF (50 ml) overnight at room temperature. The reaction mixture was washed with a saturated solution of $NaHCO_3$ (20 ml), $H_2O$ (20 ml), brine (20 ml) dried over $Na_2SO_4$ and evaporated under vacuum to afford 1.4 g of compound 4 (80% yield). The crude derivative was used for the next step without further purification.

$^1$H NMR: (200 MHz, $CDCl_3$) δ: 0.68 (3H, s, C-18 Me); 0.82 (3H, t, J=7.36 MHz, C-21); 0.93 (3H, t, J=5.2 Hz, C-21 Me); 1.26 (3H, s, C-19 Me); 3.08 (1H, m, C-23); 3.37 (1H, m, C-23); 3.61 (1H, m, C-3).

$^{13}$C NMR (50.3 MHz, $CDCl_3$) δ: 212.81, 71.09, 54.63, 51.93, 50.60, 49.84, 48.93, 43.64, 42.70, 40.11, 38.92, 36.92, 35.63, 34.19, 31.71, 31.06, 29.78, 28.25, 27.89, 25.96, 25.42, 24.51, 23.48, 21.79, 19.56, 18.77, 18.22, 17.85, 12.02, 11.95, 5.22.

3α-tert-Buthyldimethylsilyloxy-6α-ethyl-7-keto-24-nor-5β-cholan-23-I (5)

To a solution of 4 (1.4 g, 2.8 mmol) in $CH_2Cl_2$ (30 ml), tert-butyldimethylsilylchloride (496 mg, 3.22 mmol) and imidazole (230 mg, 3.36 mmol) were added and the mixture was stirred overnight at room temperature. The reaction mixture was washed with a saturated solution of $NaHCO_3$ (30 ml), brine (30 ml), and dried over anhydrous $Na_2SO_4$. The organic phase was evaporated under vacuum to afford 1.5 g of compound 5 (87% yield). The crude derivative was used for the next step without further purification.

$^1$H NMR: (200 MHz, $CDCl_3$) δ: 0.02 (6H, s, $(CH_3)_2Si$); 0.65 (3H, s, C-18 Me); 0.85 (9H, s, $(CH_3)_3CSi$); 1.19 (3H, s, C-19); 3.16 (1H, m, C-23); 3.30 (1H, m, C-23); 3.48 (1H m, C-3).

$^{13}$C NMR (50.3 MHz, $CDCl_3$) δ: 212.56, 71.93, 54.63, 51.89, 50.62, 49.81, 48.90, 43.34, 42.72, 40.11, 38.89, 36.92, 35.62, 34.37, 31.97, 30.34, 28.26, 25.83, 25.61, 24.57, 23.48, 21.77, 18.81, 17.84, 12.02, 11.92, 5.27, −4.70.

3α-tert-Buthyldimethylsilyloxy-6α-ethyl-7-keto-24-nor-5β-cholan-23-ole (6)

To a solution of 5 (1.2 g, 1.96 mmol) in acetone (12 ml), $Ag_2CO_3$ (1.1 g, 3.9 mmol) was added. The reaction mixture was refluxed overnight and then cooled to r.t., filtered on celite washed with acetone and the combined organic phases were concentrated to yield 1 g of compound 6. The crude derivative was used for the next step without further purification.

$^1$H NMR: (200 MHz, $CDCl_3$) δ: 0.02 (6H, s, $(CH_3)_2Si$); 0.65 (3H, s, C-18 Me); 0.88 (9H, s, $(CH_3)_3CSi$); 3.16 (1H, m, C-23); 3.37 (1H m, C-3); 3.69 (2H, m, C-23).

$^{13}$C NMR (50.3 MHz, $CDCl_3$) δ: 212.64, 71.96, 60.84, 55.27, 50.66, 49.87, 48.94, 43.37, 42.69, 38.94, 35.64, 34.39, 32.70, 32.00, 30.36, 29.68, 28.53, 25.85, 24.64, 23.50, 21.80, 18.84, 12.01, 11.94, −4.68.

3α-tert-Buthyldimethylsilyloxy-7α-hydroxy-6α-ethyl-24-nor-5β-cholan-23-ole (7)

To a solution of 6 (1 g, 1.96 mmol) in a mixture of THF (50 ml) and $H_2O$ (12.5 ml), $NaBH_4$ (740 mg, 19.6 mmol) was added and the mixture was stirred at room temperature for 1 hours and 30 minutes. The reaction solution was partially concentrated under vacuum and extracted with $CHCl_3$ (3×20 ml). The combined organic layers were washed with brine (1×50 ml), dried over anhydrous $Na_2SO_4$, and evaporated under vacuum. The crude residue was purified by silica gel flash chromatography using a mixture of $CH_2Cl_2$:MeOH 99:1 as mobile phase to give 0.8 g of 7 (81% yield).

$^1$H NMR: (200 MHz, $CDCl_3$) δ: 0.04 (6H, s, $(CH_3)_2Si$); 0.66 (3H, s, C-18 Me); 0.88 (9H, s, $(CH_3)_3CSi$); 3.16 (1H, m, C-23); 3.37 (1H m, C-3); 3.69 (1H, m, C-7, 2H, m, C-23).

$^{13}$C NMR (50.3 MHz, $CDCl_3$) δ: 73.30, 70.85, 60.82, 56.31, 50.55, 45.28, 42.77, 41.17, 40.03, 39.62, 38.95, 35.74, 35.52, 34.10, 33.14, 32.93, 31.01, 28.40, 25.98, 23.70, 23.18, 22.22, 20.72, 18.79, 11.62, −4.60.

3α-tert-Buthyldimethylsilyloxy-7α-hydroxy-6α-ethyl-24-nor-5β-cholan-23-sulphate triethyl ammonium salt (8)

To a solution of 7 (0.5 g, 0.99 mmol) in THF (7 ml) cooled at −3° C., $Et_3N$ (0.3 ml, 2.1 mmol) was added and the resulting mixture was stirred for 10 min. $ClSO_3H$ (0.1 ml, 1.5 mmol) was added and the mixture was stirred overnight at room temperature. Water (10 ml) was then added and the mixture was extracted with $CH_2Cl_2$ (3×15 ml), dried over anhydride $Na_2SO_4$ and evaporated under vacuum. The crude sulphate derivative was used for the next step without further purification.

3α,7α,23-trihydroxy-6α-ethyl-24-nor-5β-cholan-23-sulphate triethyl ammonium salt (9)

To a solution of 8 (0.5 g, 0.77 mmol) in acetone (8 ml), $PdCl_2(CH_3CN)_2$ (10 mg, 0.05 eq) was added and the mixture was stirred at room temperature for 3 hours. The reaction mixture was filtered, concentrated under vacuum and purified by medium pressure Lichroprep RP-8 using a $MeOH/H_2O$ 8/2 mixture as mobile phase to afford 0.115 g of 9, mp 118-121° C.

$^1$H NMR (200 MHz, $CD_3OD$) δ: 0.70 (3H, s, C-18 Me); 0.91 (3H, m, C-21 Me, 3H, C-25); 0.98 (3H, d, J=6.4 Hz, C-19 Me); 1.32 (9H, t, J=7.3 Hz, $(CH_3-CH_2)_3N$); 3.20 (6H, q, J=7.31 Hz, $(CH_3-CH_2-)_3N$, 3.31 (1H, m, C-3); 3.65 (1H, bs, C-7); 4.03 (2H, m, $CH_2$-23).

$^{13}$C NMR ($CD_3OD$) δ: 9.23, 12.05, 12.19, 19.14, 21.97, 23.52, 23.76, 24.57, 34.23, 34.51, 36.56, 36.65, 36.79, 41.06, 41.55, 43.13, 47.73, 50.28, 51.68, 57.80, 67.19, 71.16, 73.23.

3α,7α,23-trihydroxy-6α-ethyl-24-nor-5β-cholan-23-sulphate sodium salt (10)

To a solution of 8 (0.4 g, 0.72 mmol) in a mixture of acetone (4 ml) and $H_2O$ (0.08 ml), $PdCl_2(CH_3CN)_2$ (10 mg, 0.05 eq) was added and the resulting mixture was stirred at room temperature for 3 hours. The reaction mixture was filtered over celite and concentrated under vacuum. The resulting residue was treated with a methanolic solution of 10% NaOH for 2 h. The resulting mixture was concentrated under vacuum and submitted to liquid medium pressure purification using a mixture of $CH_3OH/H_2O$ (7:3) as mobile phase to afford 0.09 g of 10 (25% yield).

Example 2

Biological Activities

Tests were first carried out in order to verify whether UPF-987 modulates FXR-regulated genes, in comparison with chenodeoxycholic acid (CDCA). CDCA is a primary bile acid that functions as an endogenous ligand of the farnesoid-x-receptor (FXR; NR1H4). The biological activity of UPF-987 on FXR activity was first tested in an in vitro assay using the fluorescence resonance energy transfer (FRET) cell free assay, described in Pellicciari R., et al. J Med Chem. 2002 15; 45:3569-72.

Briefly, reactions contained europium-labeled anti-GST antibody and streptavidin-conjugated allophycocyanin, FXR GST-LBD fusion proteins and biotinylated SRC1 sensor peptide. Reactions were incubated at room temperature for 1 h in FRET buffer (10 mM Hepes, pH 7.9, 150 mM NaCl, 2 mM MgCl2, 1 mM EDTA, 0.1 mg/ml BSA). FRET was measured on a Victor 1420 multilabel counter.

In the FRET cell-free assay, the recruitment of Scr-1, a co-activating factor for FXR, occurs at a concentration of compound that is almost 300-fold lower than that required for the natural FXR-ligand CDCA (Table 1).

TABLE 1

Activity of UPF-987 on Human FXR on FRET

| Compound Tested | Cell-Free Assay $EC_{50}$ (μM) | Efficacy[1] |
|---|---|---|
| UPF-987 | 0.014 | 111 |
| CDCA | 4 | 100 ± 3 |

[1]Relative recruitment of the SRC1 peptide to FXR where CDCA = 100%.
All data are mean ± SE, n = 4.

It was also evaluated if UPF-987 modulated FXR-regulated genes in a cellular assay using a human hepatocyte cell line (HepG2). In a cell transfection assay using the HepG2 cell line, UPF-987 proved a potent FXR ligand. Exposure of HepG2 cells to UPF-987 transactivates FXR. In other experiments using liver cells transfected with viral constructs carrying the FXR gene or other nuclear receptors cloned upstream to the luciferase gene, it was found that UPF-987 functions as a selective FXR ligand in mouse, rat, and human hepatocytes. A detailed description of these methods can be found in the following reference: Fiorucci S., et al. *Gastroenterology* 2004.

Briefly, for luciferase assay, HepG2 cells were cultured in E-MEM supplemented with 1% penicillin/streptomycin, 1% L-glutamine and 10% fetal bovine serum (high glucose) (CELBIO). Cells were grown at 37° C. in 5% $CO_2$. All the transfections were making using a calcium phosphate coprecipitation method in the presence of 25 μM chloroquine as inhibitor for DNA degradation. Transient transfections were performed using 500 ng of reporter vector phsp27-TKLUC, 200 ng pCMV-βgal, as internal control for transfection efficiency, and 50 ng of each receptor expression plasmid pSG5-FXR, pSG5-RXR. The pGEM vector was added to normalize the amounts of DNA transfected in each assay (2.5 μg). The transfection efficiency was evaluated by O-gal expression, obtained by co-transfecting the cells with pCMV-βgal plasmid. Forty-Eight hours post-transfection, HepG2 cells were stimulated with 1 μM UPF-987 for 18 h. Control cultures received vehicle (0.1% DMSO) alone. Cells were lysed in 100 μl diluted reporter lysis buffer (Promega), and 0.2 μl cellular lisate was assayed for luciferase activity using Luciferase Assay System (Promega). Luminescence was measured using an automated luminometer. Luciferase activities were normalized for transfection efficiencies by dividing the relative light units by O-galactosidase activity.
Regulation of FXR Target Gene Expression by UPF-987 in HepG2 Cells To establish if UPF-987 is a FXR modulator and exerts differential activities, human HepG2 cells were exposed to UPF-987, CDCA (natural FXR ligand) and to its 6-ethyl-derivative, 6-ECDCA, which is a potent FXR ligand. The effects of these ligands on FXR responsive genes was then investigated by quantitative reverse transcription PCR (qRT-PCR).

Figure 3:
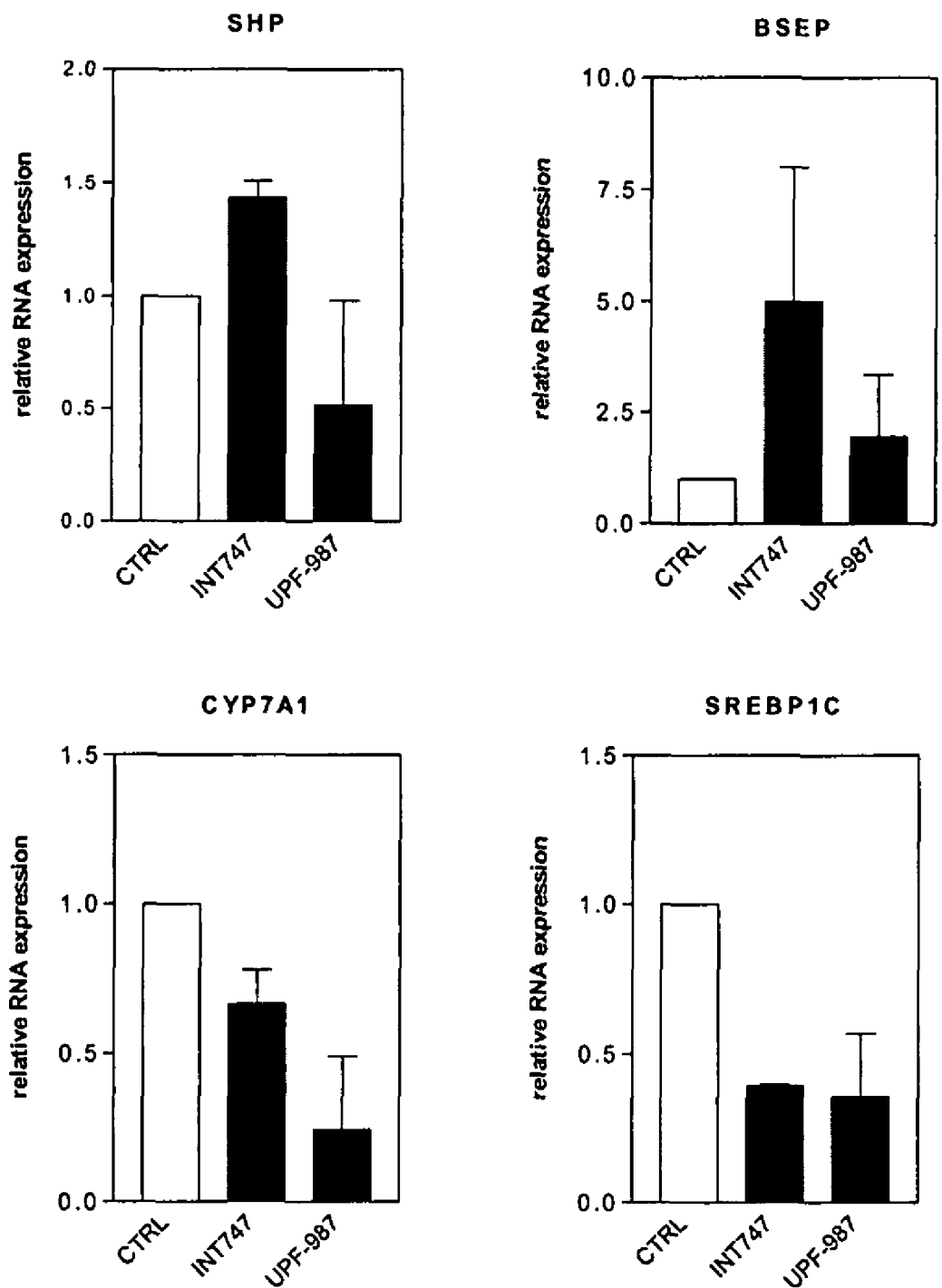
FIG. 3 shows FXR target gene expression in vitro. The result is the mean of two quantitative Real-Time PCR experiments.
Figure 4:
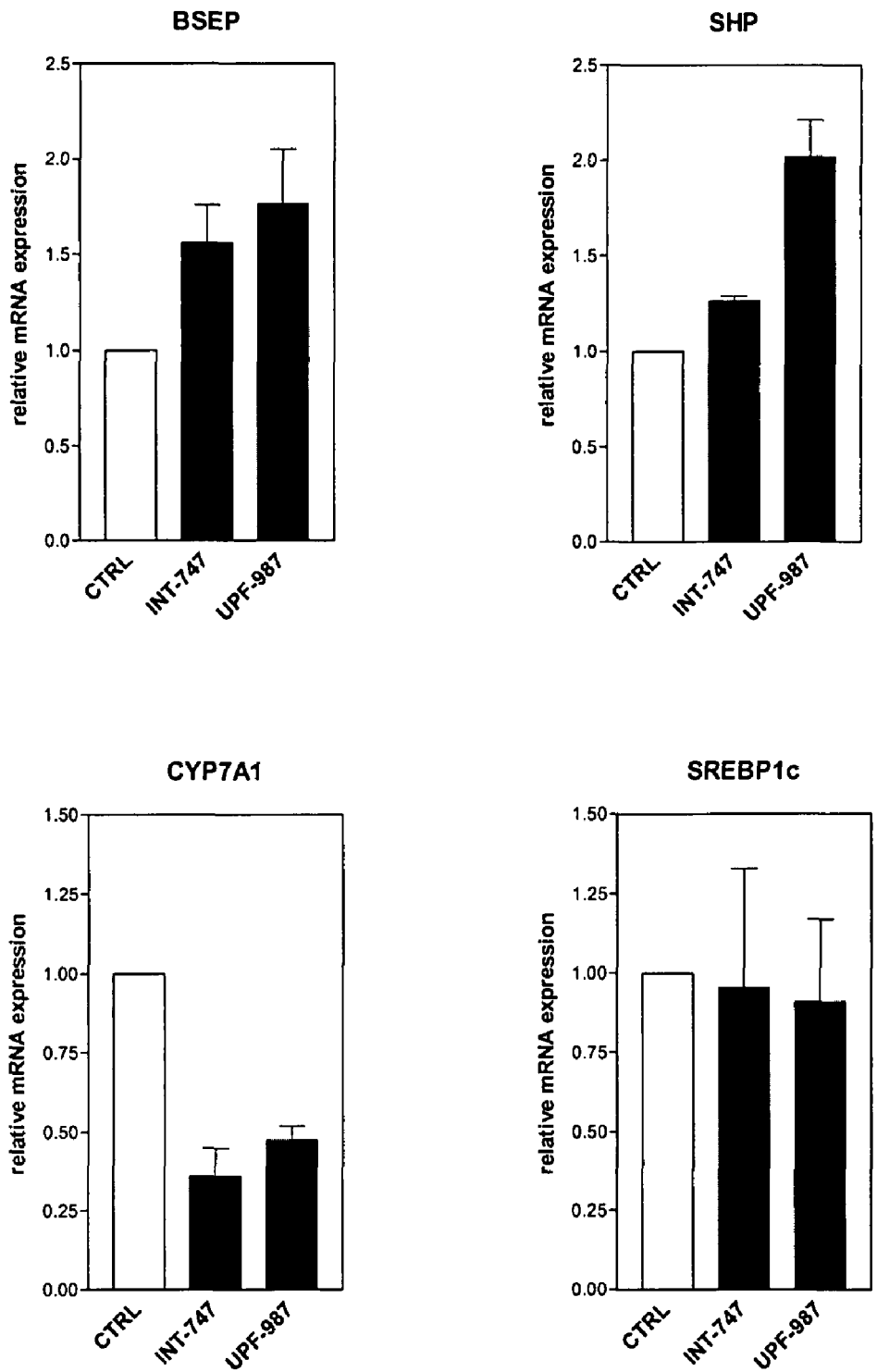
FIG. 4 shows representative FXR target gene expression in cells derived from mouse liver in vivo. The data is the mean of two quantitative Real-Time PCR experiments.

Briefly, all PCR primers were designed using PRIMER3-OUTPUT software using published sequence data from the NCBI database. Total RNA was isolated (TRIzol reagen, Invitrogen srl, Milan, Italy) from specimens taken from livers. One microgram of purified RNA was treated with DNAse I for 10 minutes at room temperature, followed by incubation at 95° C. for 3 minutes in the presence of 2.5 mmol/L EDTA. The RNA was reverse transcribed with Superscript III (Invitrogen, Carsbad, Calif.) in 20 μL reaction volume using random primers. For quantitative RT-PCR, 100 ng template was dissolved in a 25 μL containing 0.3 μmol/L of each primer and 12.5 μL of 2×SYBR Green PCR Master mix (Fynnzimes- DyNAmo SYBRR Green qPCR mix). All reactions were performed in triplicate, and the thermal cycling conditions were as follows: 2 minutes at 95° C., followed by 50 cycles of 95° C. for 20 seconds, 55° C. for 20 seconds and 72° C. for 30 seconds on iCycler iQ instrument (Bio-Rad, Hercules, Calif.). The mean value of the replicates for each sample was calculated and expressed as the cycle threshold (CT; cycle number at which each PCR reaction reaches a predetermined fluorescent threshold, set within the linear range of all reactions). The amount of gene expression was then calculated as the difference (ΔCT) between the CT value of the sample for the target gene and the mean CT value of that sample for the endogenous control (GAPDH). Relative expression was calculated as the difference (ΔΔCT) between ΔCT values of the test control sample for each target gene. The relative mRNA expression was shown as 2-ΔΔCT (FIG. 3). The Primers (SEQ ID NOS.: 1-10) used in Real-Time PCR were:

```
Hgapdh (SEQ ID NOS.: 1 & 2):
gaaggtgaaggtcggagt
and catgggtggaatcatattggaa;

hCYP7A1 (SEQ ID NOS.: 3 & 4):
caccttgaggacggttccta
and cgatccaaagggcatgtagt;

Hshp (SEQ ID NOS.: 5 & 6):
gctgtctggagtccttctgg
and ccaatgatagggcgaaagaagag;

Hbsep (SEQ ID NOS.: 7 & 8):
gggccattgtacgagatcctaa
and tgcaccgtcttttcactttctg;

hSREBP1c (SEQ ID NOS.: 9 & 10):
gcaaggccatcgactacatt
and ggtcagtgtgtcctccacct.
```

In contrast to FIG. 3, a different in vitro experiment using quantitative reverse transcription PCR, demonstrated that while no direct cell toxicity was observed upon exposure to any of these ligands, exposure of HepG2 cells to CDCA and its 6-ECDCA derivative, resulted in a 2-3 fold induction of SHP, an FXR regulated gene. By contrast, despite the fact that UPF-987 is a FXR ligand (see above), it stimulates SHP expression. All the FXR ligands tested, namely CDCA, 6-ECDCA and UPF-987 exerted the same effect on CYP7α1 (all agents caused a 60-70% reduction of the expression of CYP7α1 mRNA). In addition, exposure to UPF-987 induced BSEP and SHP mRNA expression (approximately 2-3 fold induction). This effect was significantly more pronounced with UPF-987 than with the other FXR ligands. Furthermore, similarly to the other ligands, exposure to UPF-987 resulted in a potent inhibition of SREPB-1c and FAS mRNA expression. Taken together, these data suggest that UPF-987 is an FXR modulator that functions as a potent FXR ligand, and unexpectedly alters FXR regulated genes, causing significant induction of bile acid transporters (for example BSEP) and potent suppression of lipid-related genes. In addition, UPF-987 represses the expression of Cyp7α1, a gene that is critically involved in bile acid synthesis from cholesterol. The regulation of these FXR target genes suggests that UPF-987 is a gene-selective FXR ligand that may inhibit bile acid biosynthesis through the classical pathway while increasing bile acid secretion from hepatocytes, without interfering with SHP expression. This effect is desirable, since it narrows the pharmacological activities of these FXR ligands, and might prevent metabolic activation typically associated with SHP induction.

Results of In vitro pharmacology studies on UPF-987 are shown in Table 2 below.

TABLE 2

| | | In Vitro Pharmacology Studies on UPF-987 | | | |
|---|---|---|---|---|---|
| Cells | Test Article | Doses | Species | Endpoints | Summary Findings |
| Cell free assay | UPF-987 CDCA | Concentrations ranging from 1 nM to 100 μM | n/a | Potency of UPF-987 as an FXR ligand in a cell free assay using FRET assay | The results of these experiments show that UPF-987 is a potent ligand of FXR ($EC_{50}$ ~ 14 nM) |
| Hepatoma cell line(HepG2) | UPF-987 CDCA 6-ECDCA | Concentrations ranging from 1 to 100 μM | Human | Potency on regulation of FXR and FXR regulated genes (SHP, CYP7α1, CYP8β1, SREPB1c, | UPF-987 causes transactivation of FXR. UPF-987 is a potent inducer of BSEP and SHP. UPF-987 is potent inhibitor of Cyp7A1 and |

TABLE 2-continued

In Vitro Pharmacology Studies on UPF-987

| Cells | Test Article | Doses | Species | Endpoints | Summary Findings |
|---|---|---|---|---|---|
| In vivo testing Intact mouse | UPF-987 CDCA 6E-CDCA | 5 mg/kg intraperitoneal 4 days | Mice | FAS and BSEP) Regulation of FXR related genes (SHP, CYP7α1, CYP8β1, SREPB1c, FAS and BSEP) in vivo | SREBP1c mRNA expression UPF-987 administration induces liver expression of BSEP and SHP and inhibits liver Cyp7A1, SREBP1c and FAS mRNA expression |
| In vivo testing ANIT-induced cholestasis | UPF-987 | 5 mg/kg oral 7 days administration | Rats | Biochemical assessment of cholestasis | UPF-987 administration reduces ANIT induced cholestasis as measured by serum liver enzymes (AST, bilirubin, Alc. Phosphatase and cholesterol) and modulates liver expression of NTCP, BSEP and CYP7A1 mRNA expression |

Example 3

Regulation of FXR Target Genes by UPF-987 In Vivo

Background

Compound 9 is also referred to as UPF-987. FXR plays a key role in the transcriptional regulation of genes involved in bile acid metabolism and lipid/cholesterol and glucose homeostasis. The regulation of these interactions is highly complex and contains multiple feedback loops to self-regulate the transcriptional circuits. The overlapping range of agonistic and antagonistic ligands, as well as of target genes shared by FXR with other metabolic nuclear receptors including PPARs and LXR, may serve as a redundant safety mechanism to elicit a protective response so that even when one pathway is compromised, a salvage pathway takes over. Crucial to the complexity of putative convergent and divergent functions of the metabolic nuclear receptors are their transcriptional coactivators and corepressors, that will be recruited in various manner from FXR modulators.

FXR modulators will be used for the treatment of the inflammatory, cholestatic, fibrotic liver disorders, and metabolic disorders including hypertriglyceridemic and hypercholesterolemic states and, by extension, atherosclerosis and its complications.

In conclusion, FXR is emerging as a particularly intriguing therapeutic target, not only for the promising application associated with its modulation but also for its peculiar mechanism of ligand recognition and gene activation.

Materials and Methods

Animals

Six- to eight-week old female Balb/c mice were obtained from Charles River (Charles River Laboratories, Inc., Wilmington, Mass.). Animals were fed a standard chow pellet diet, had free access to water, and were maintained on a 12-h light/dark cycle. All procedures in this study were approved by the Animal Study Committees of the University of Perugia (Italy) according to governmental guidelines for animal care. Animals were treated for 5 days by intraperitoneal injection of 6-ECDCA 5 mg/Kg/day, while control animals were treated with vehicle alone (methyl-cellulose). At the end of the experiment mice were sacrificed and liver was removed to perform Real Time PCR analysis of FXR target genes.

Quantitative Real-Time PCR

Quantitative Real-Time PCR was performed as above (see 1.1 Materials and Methods). The primers (SEQ ID NOS.: 11-20) used were:

```
Mgapdh (SEQ ID NOS.: 11 & 12):
ctgagtatgtcgtggagtctac
and gttggtggtgcaggatgcattg Mbsep (SEQ ID NOS.: 13 & 14):
aaatcggatggtttgactgc
and tgacagcgagaatcaccaag mSHP (SEQ ID NOS.: 15 & 16):
tctcttcttccgccctatca
and aagggcttgctggacagtta mCYP7A1 (SEQ ID NOS.: 17 & 18):
aagccatgatgcaaaacctc
and gccggaaatacttggtcaaa
```

Figure 5:
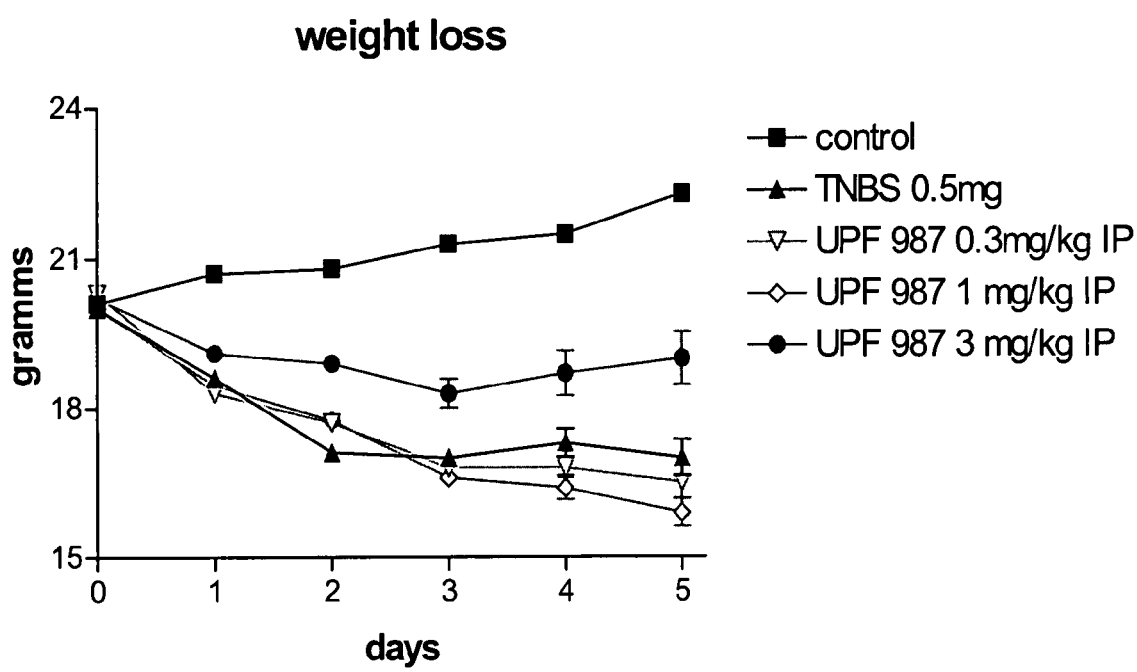
FIG. 5 shows the effect of UPF-987 on weight loss induced by TNBS.
Figure 6:
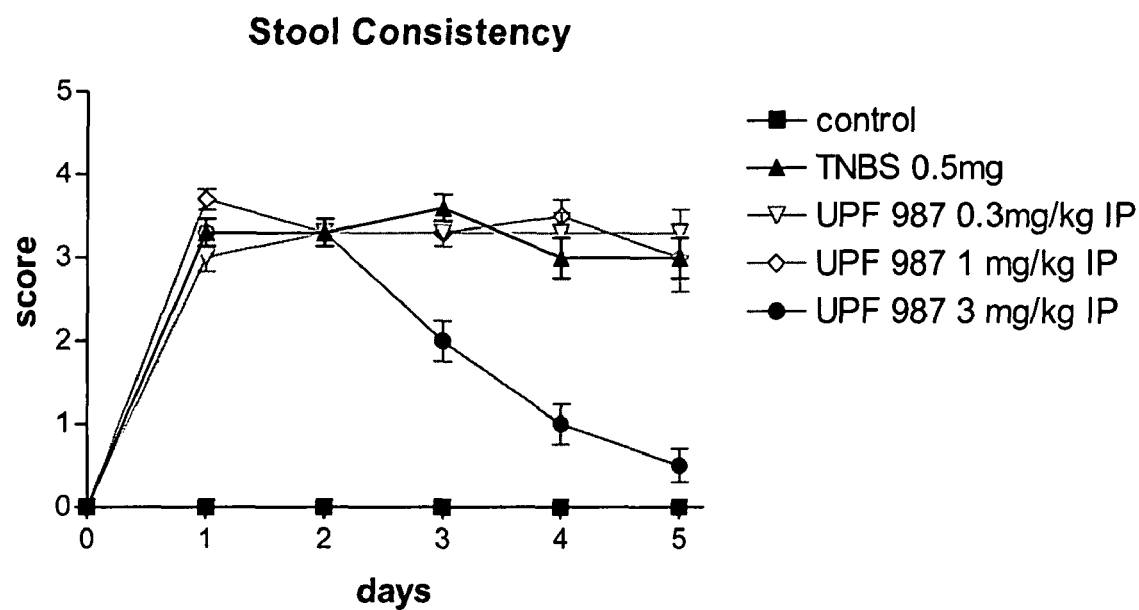
FIG. 6 shows the effect of UPF-987 on stool consistency.
Figure 7:
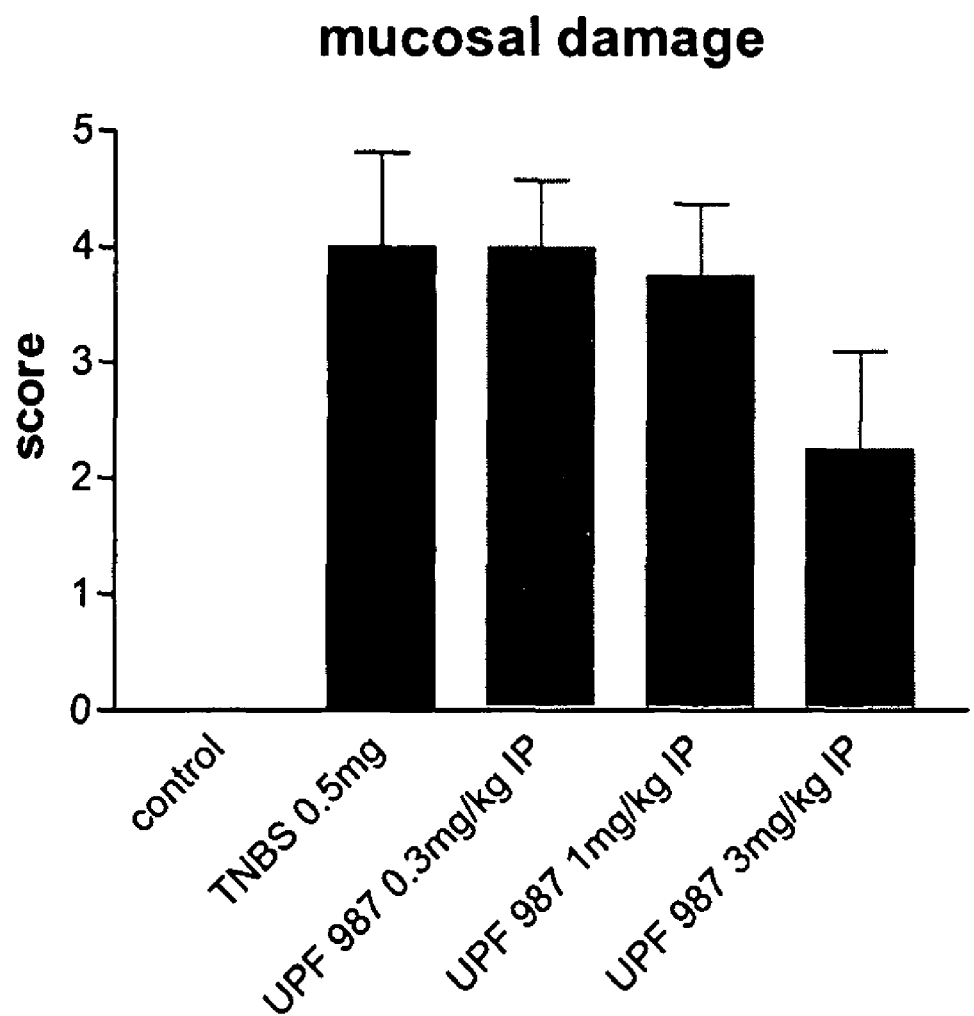
FIG. 7 shows the effect of UPF-987 on mucosal damage score.
Figure 8:
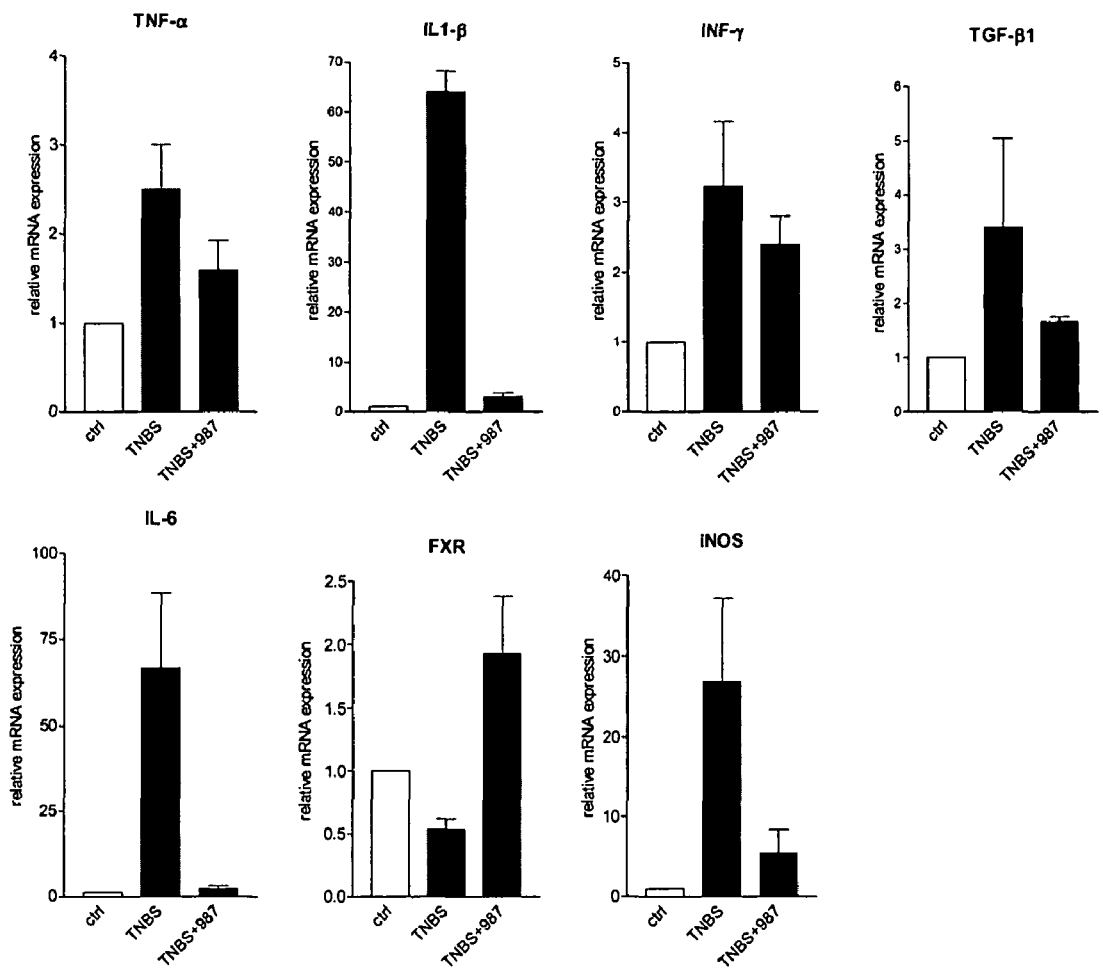
FIG. 8 shows the effect of UPF-987 on mouse colon genes expression. The result is the mean of two quantitative Real-Time PCR experiments.
Figure 9:
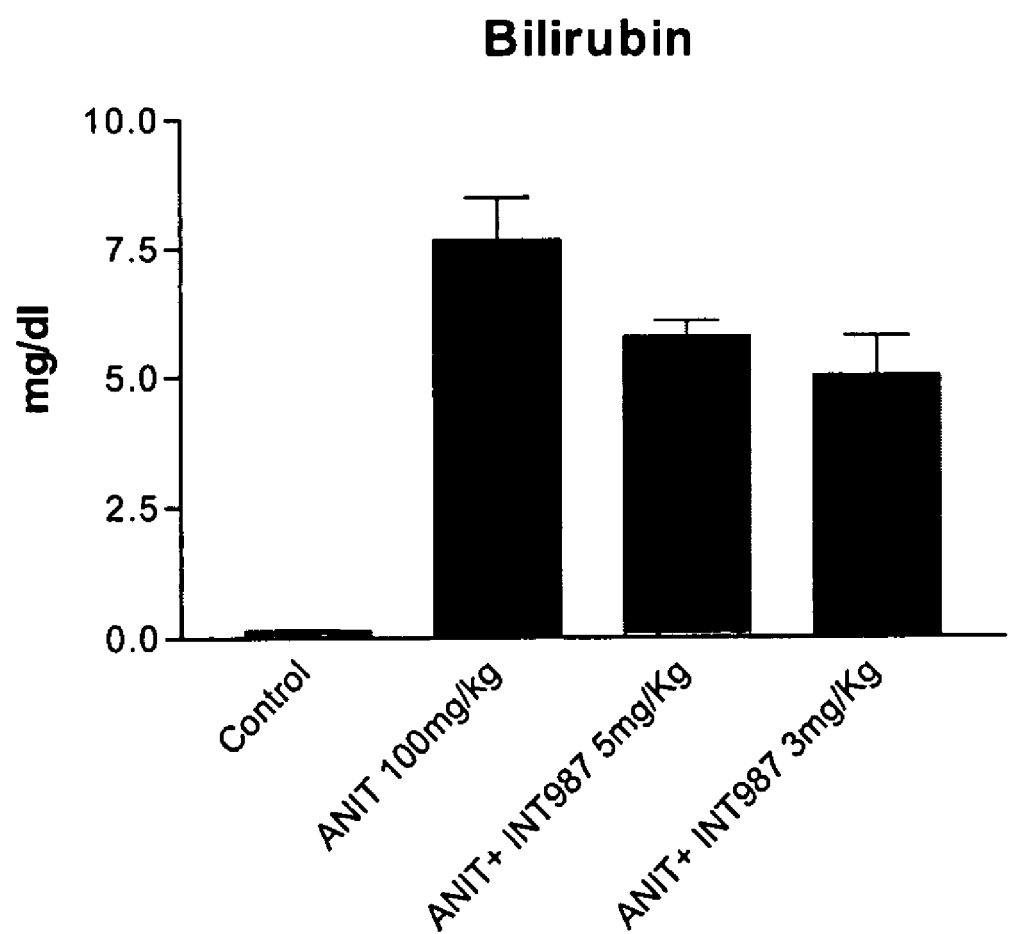
FIG. 9 shows the effect of UPF-987 on plasmatic bilirubin in ANIT-induced cholestasis.
Figure 10:
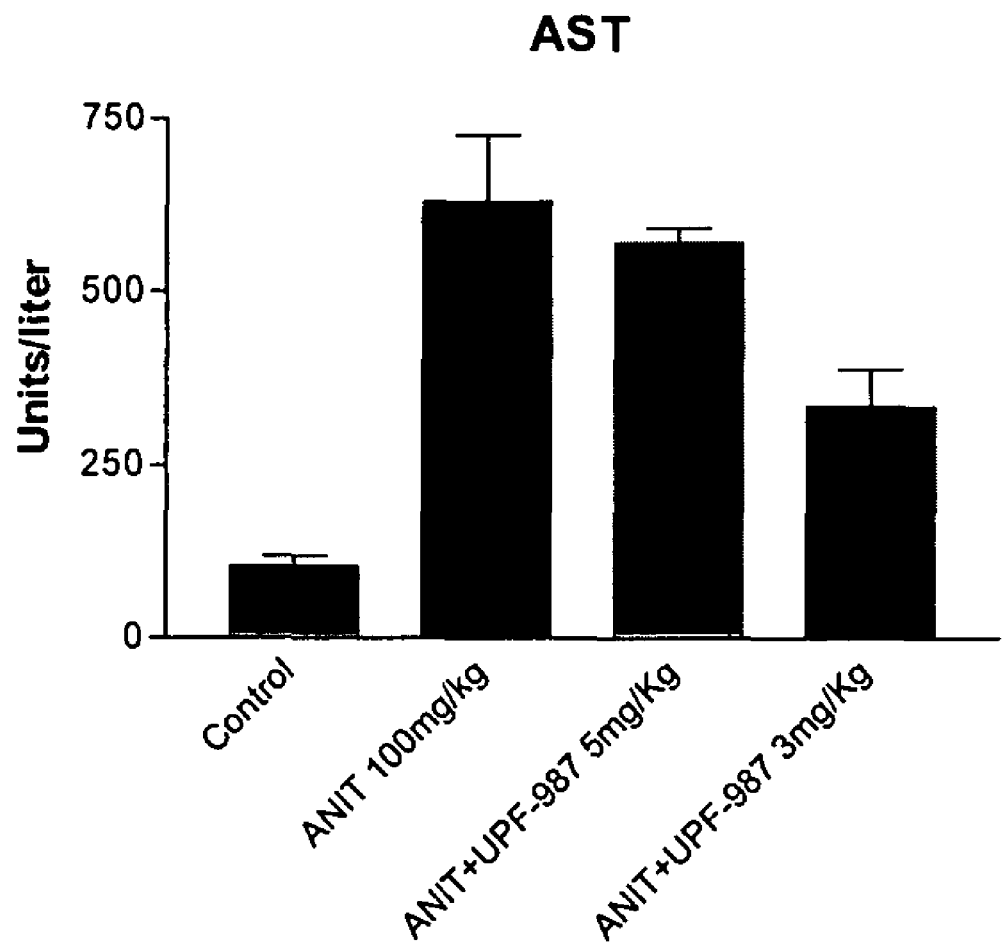
FIG. 10 shows the effect of UPF-987 on plasmatic AST in ANIT-induced cholestasis.
Figure 11:
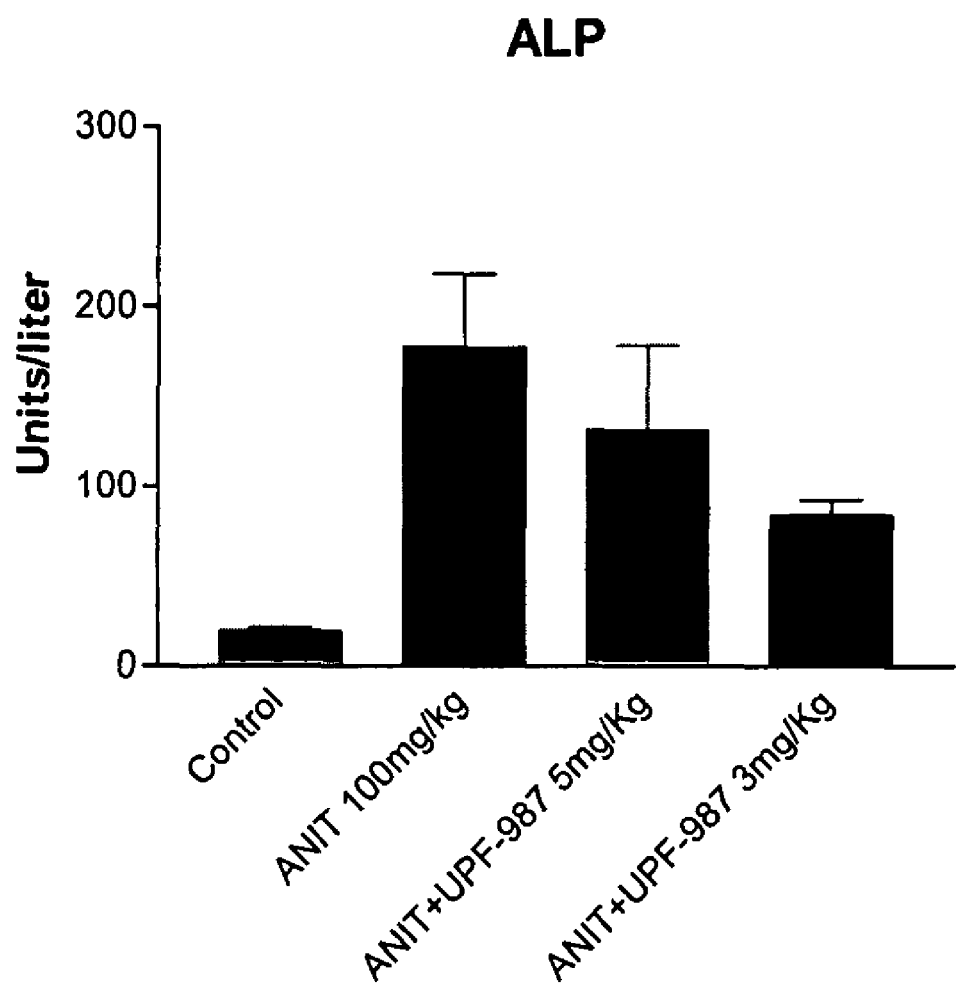
FIG. 11 shows the effect of UPF-987 on plasmatic ALP in ANIT-induced cholestasis.
Figure 12:
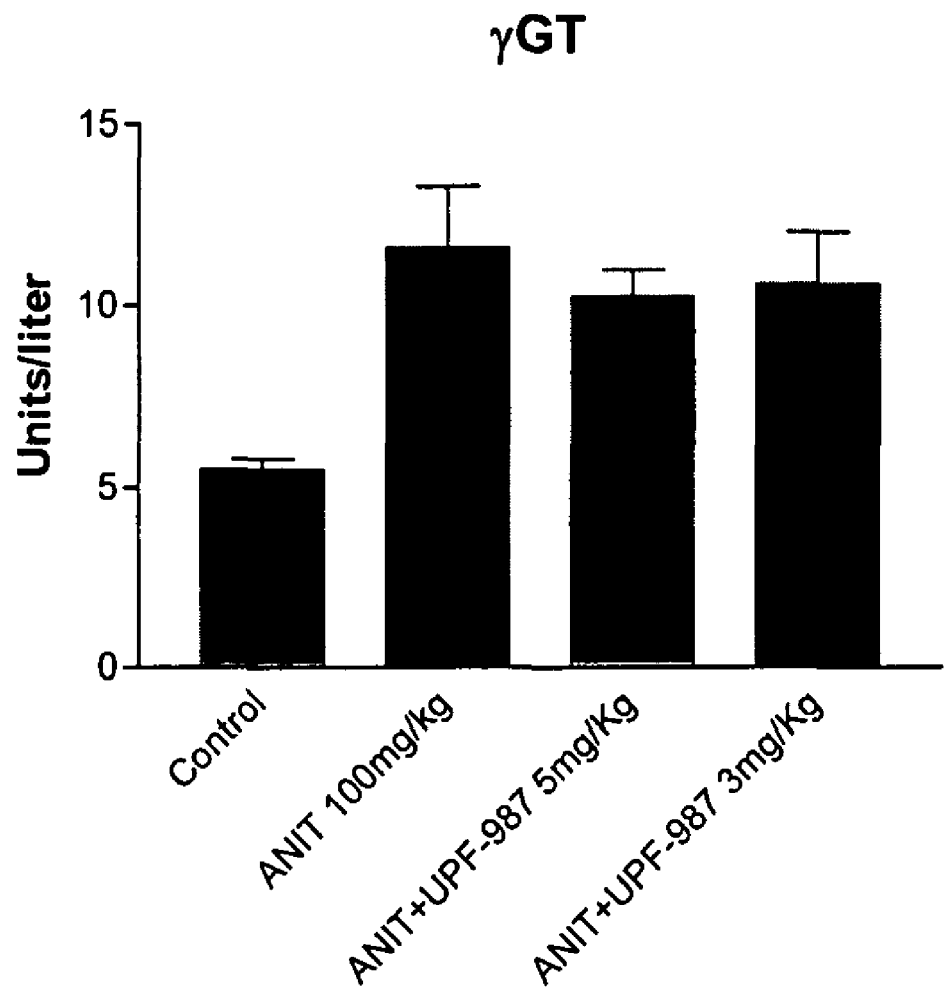
FIG. 12 shows the effect of UPF-987 on plasmatic gammaGT in ANIT-induced cholestasis.
Figure 13:
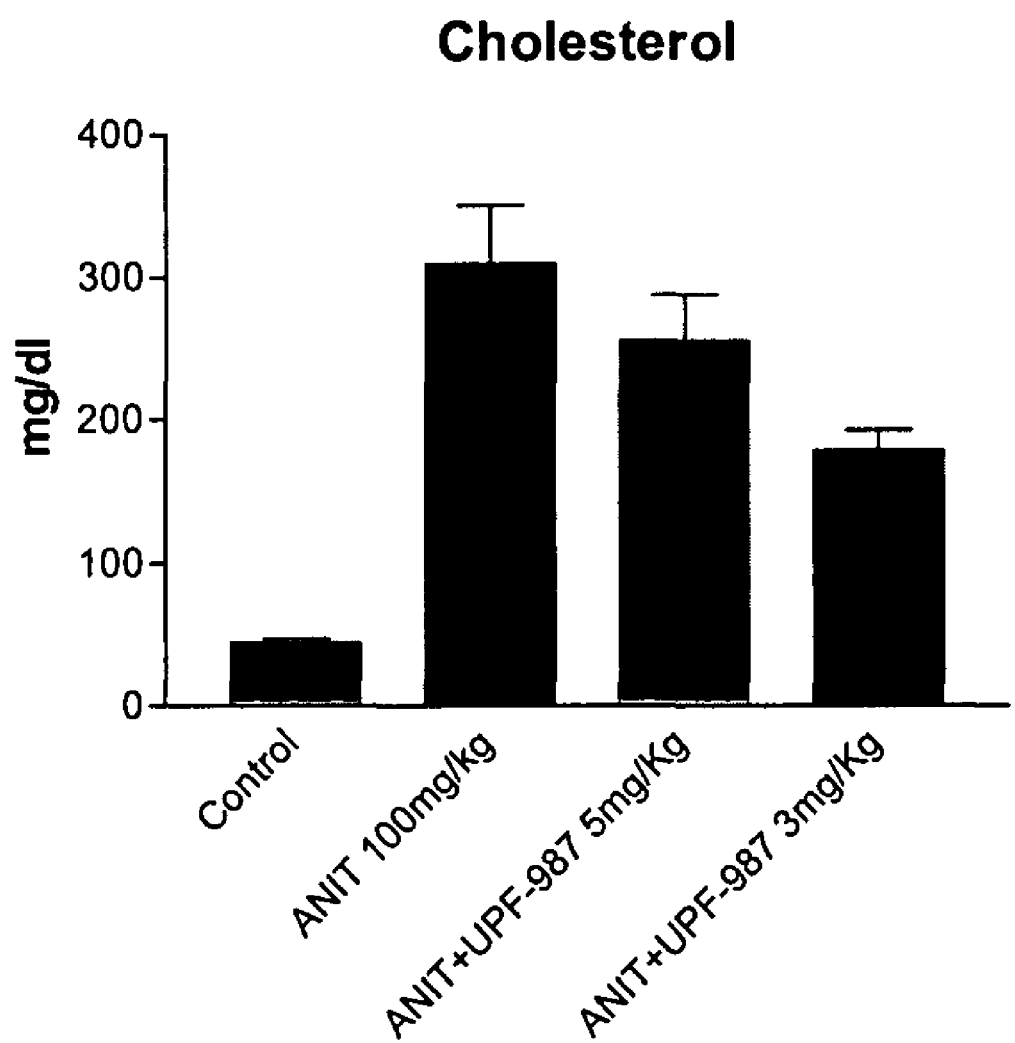
FIG. 13 shows the effect of UPF-987 on plasmatic cholesterol in ANIT-induced cholestasis.
Figure 14:
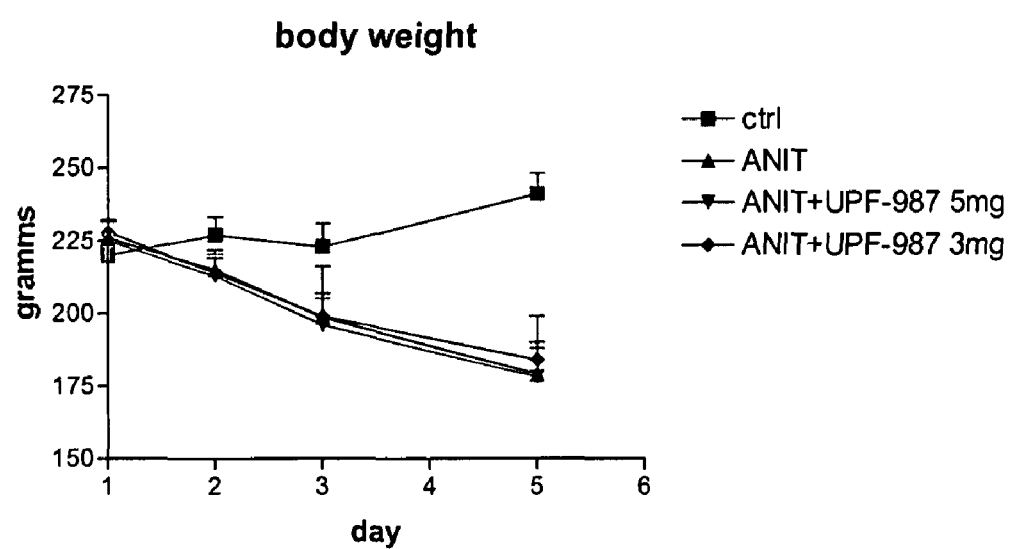
FIG. 14 shows the effect of UPF-987 on body weight in ANIT-induced cholestasis.
Figure 15:
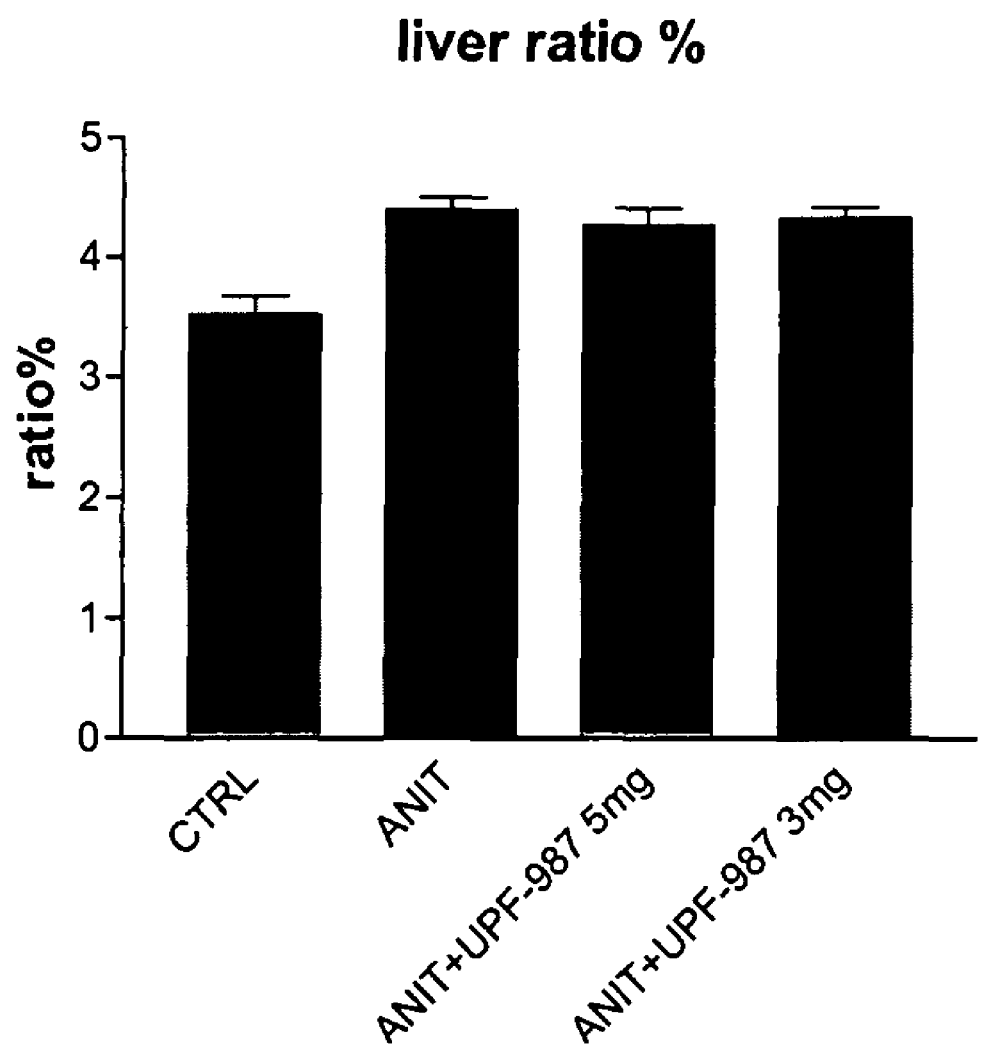
FIG. 15 shows the effect of UPF-987 on liver weight in ANIT-induced cholestasis.
Figure 16:
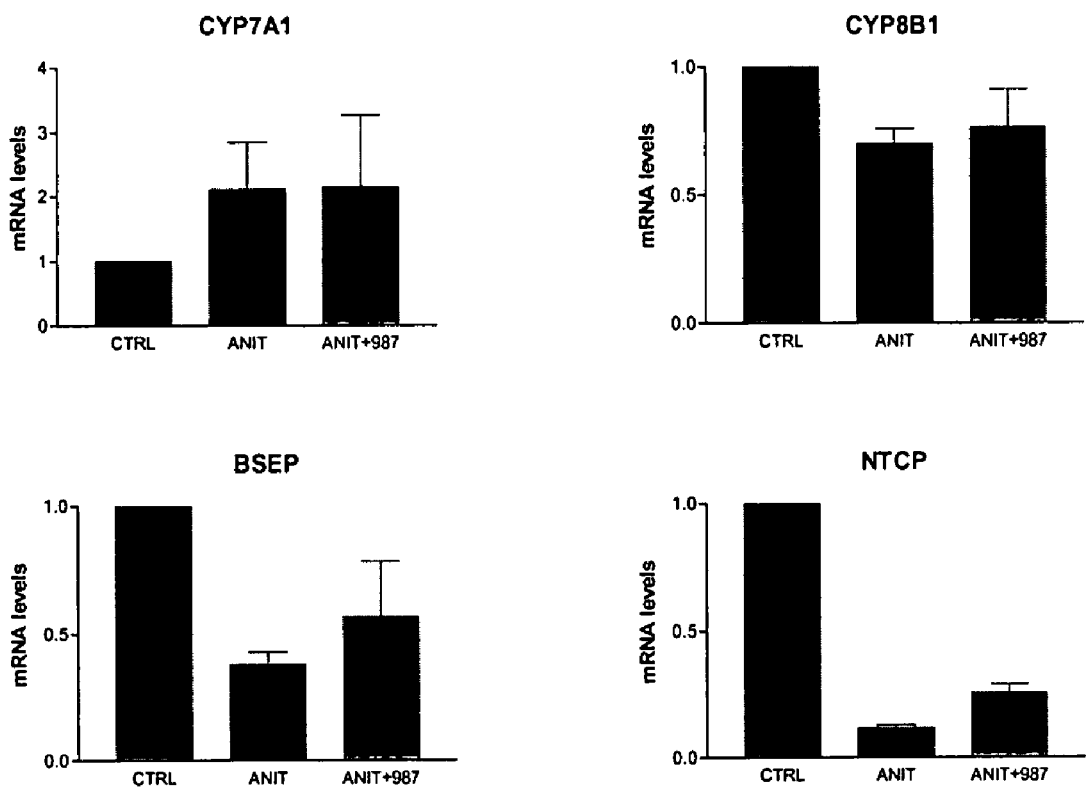
FIG. 16 shows the effect of UPF-987 on FXR target genes expression in the liver of ANIT-induced cholestatic rat. The result is the mean of two quantitative Real-Time PCR experiments.
Figure 17:
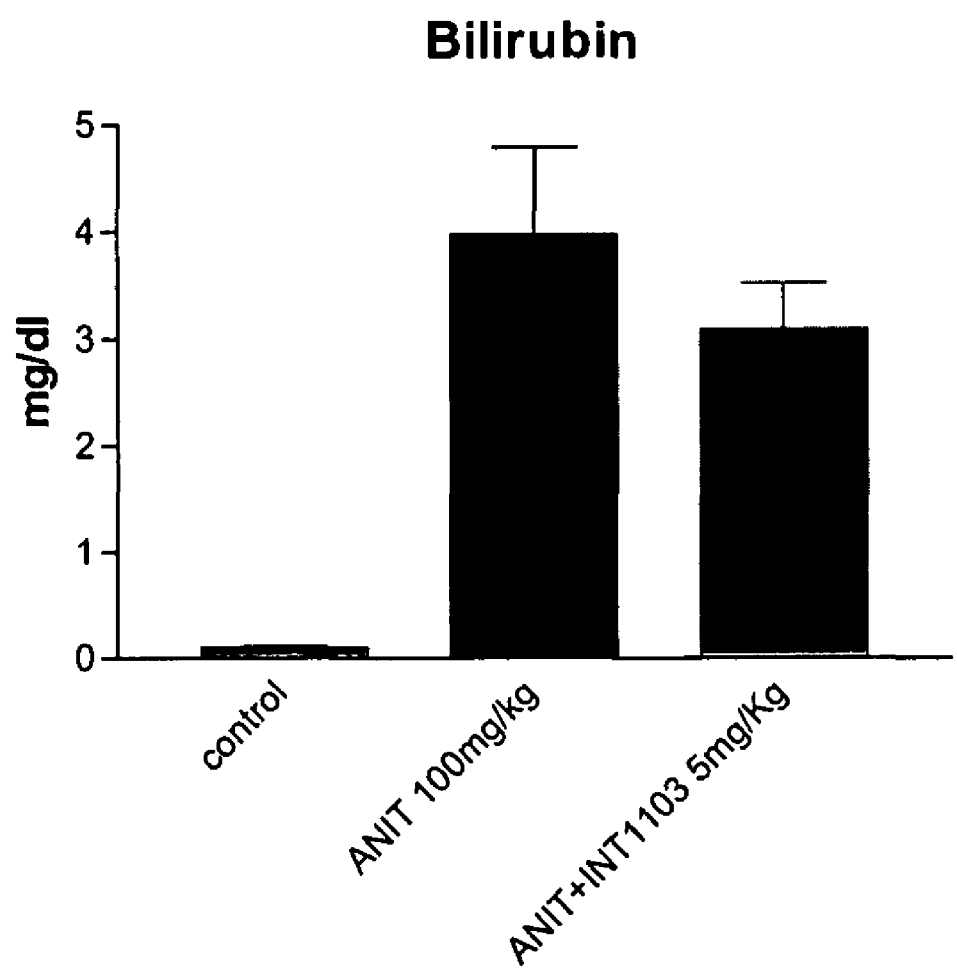
FIG. 17 shows the effect of INT-1103 on plasmatic bilirubin in ANIT-induced cholestasic rats.
Figure 18:
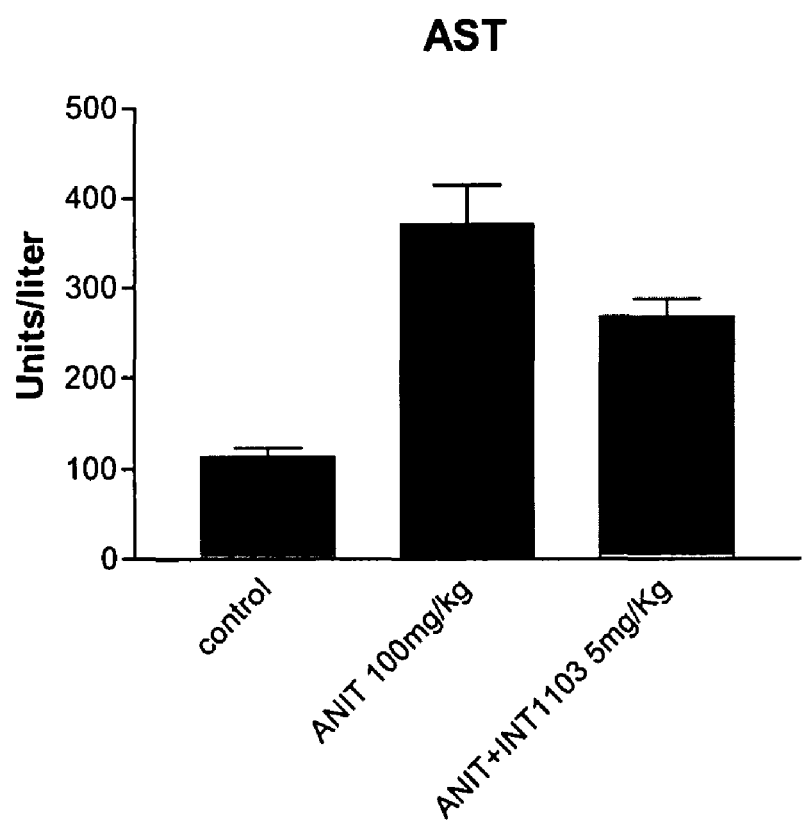
FIG. 18 shows the effect of INT-1103 on plasmatic AST in ANIT-induced cholestasic rats.
Figure 19:
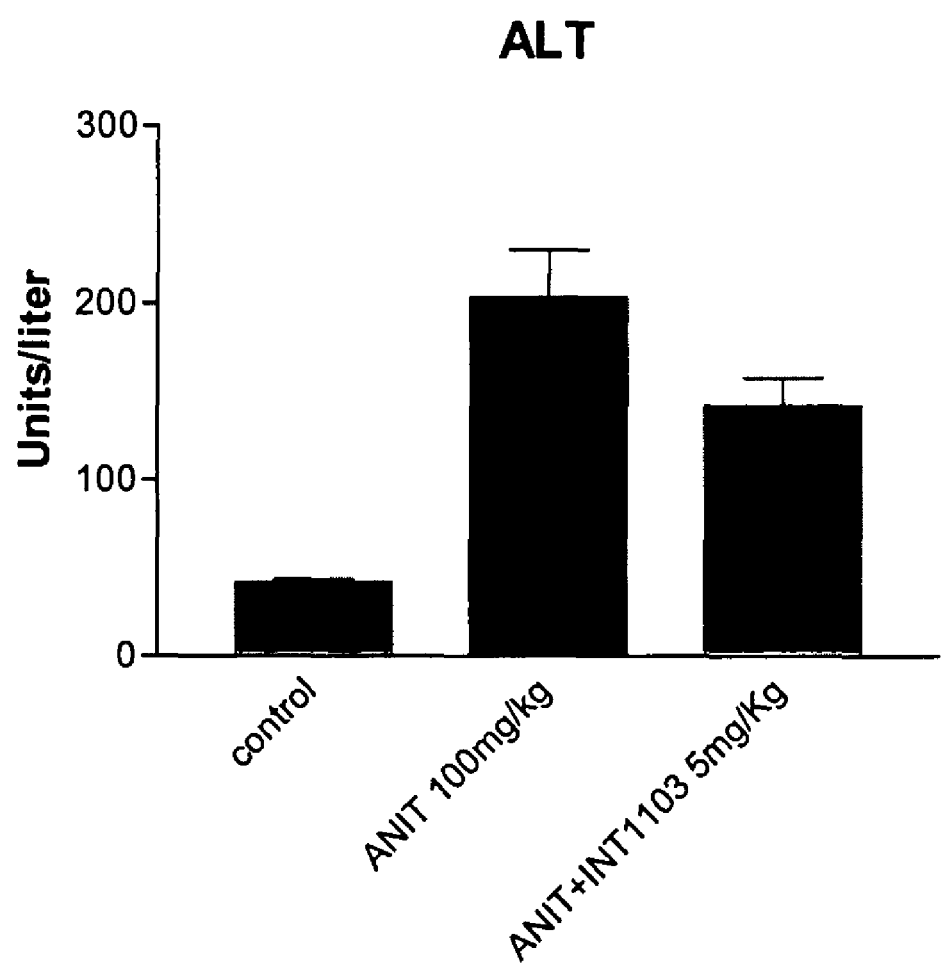
FIG. 19 shows the effect of INT-1103 on plasmatic ALT in ANIT-induced cholestasic rats.
Figure 20:
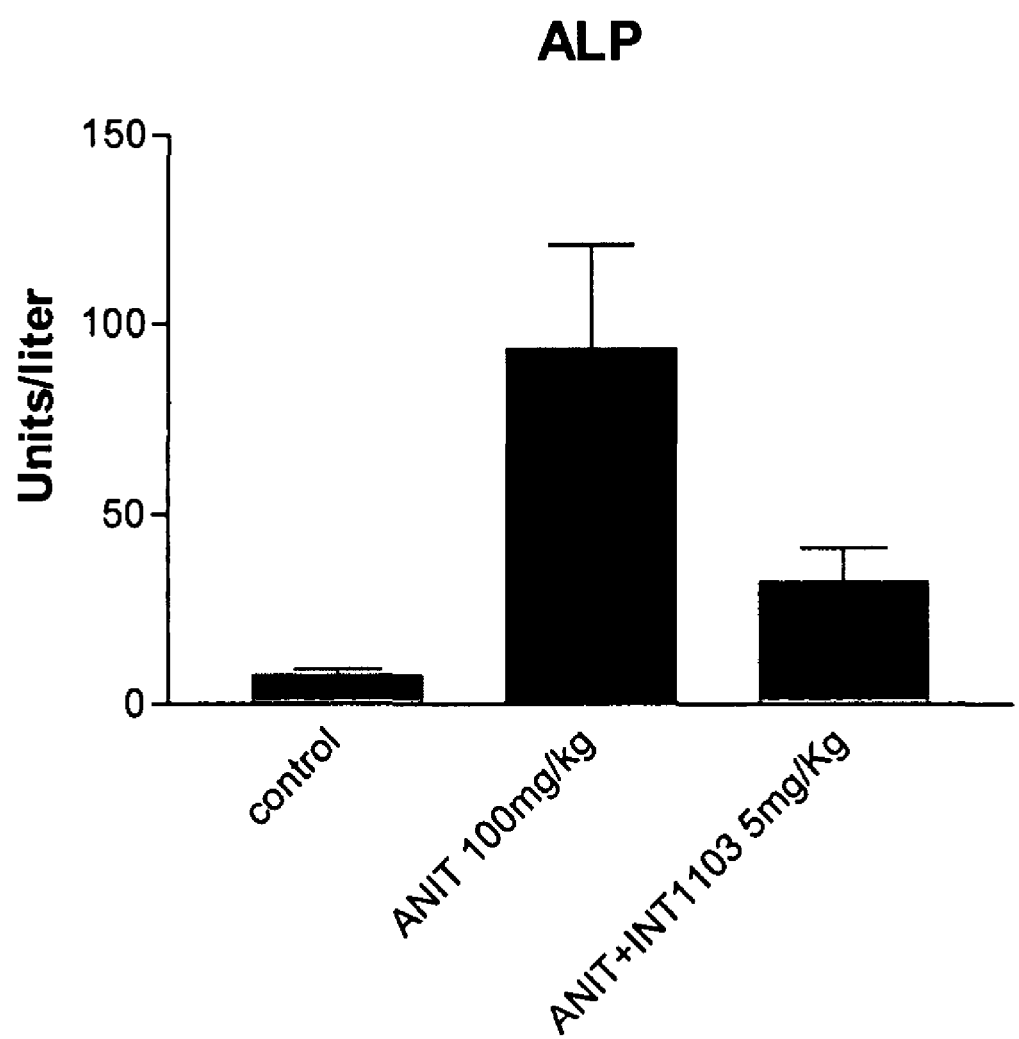
FIG. 20 shows the effect of INT-1103 on plasmatic ALP in ANIT-induced cholestasic rats.
Figure 21:
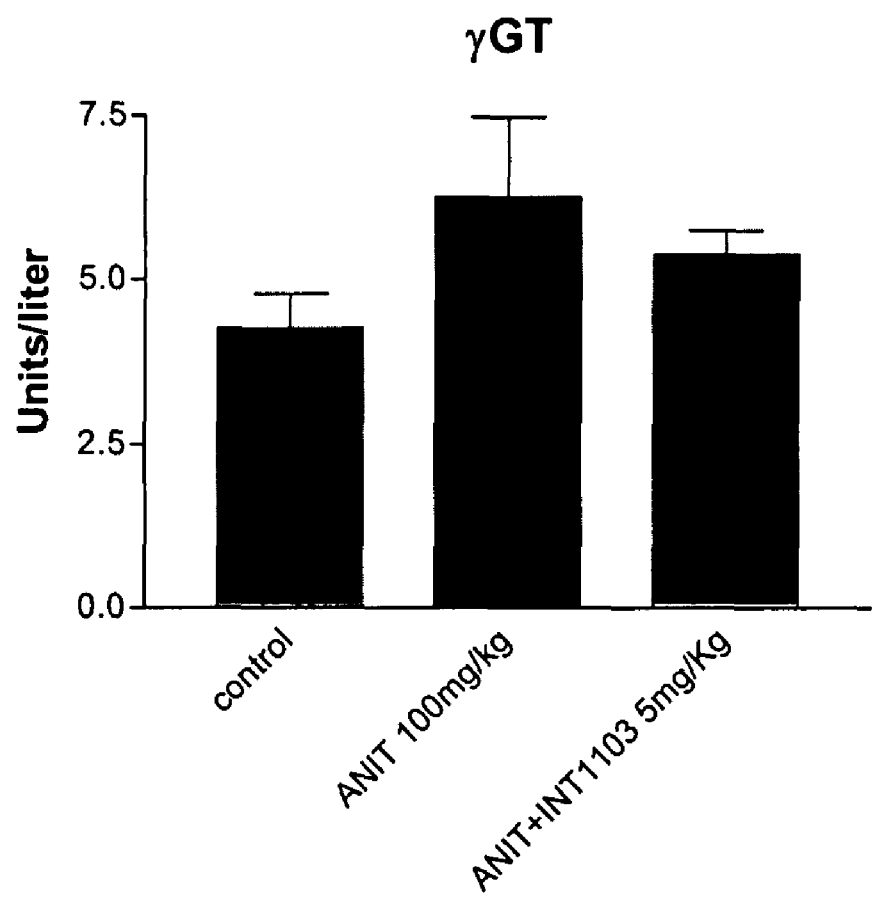
FIG. 21 shows the effect of INT-1103 on plasmatic gammaGT in ANIT-induced cholestasic rats.
Figure 22:
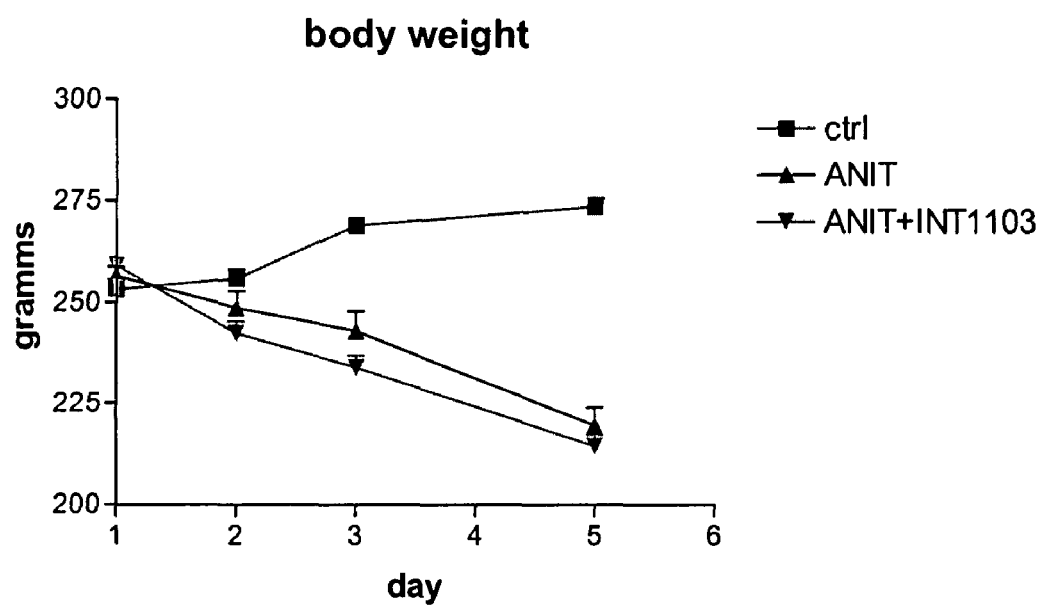
FIG. 22 shows the effect of INT-1103 on body weight in ANIT-induced cholestasic rats.
Figure 23:
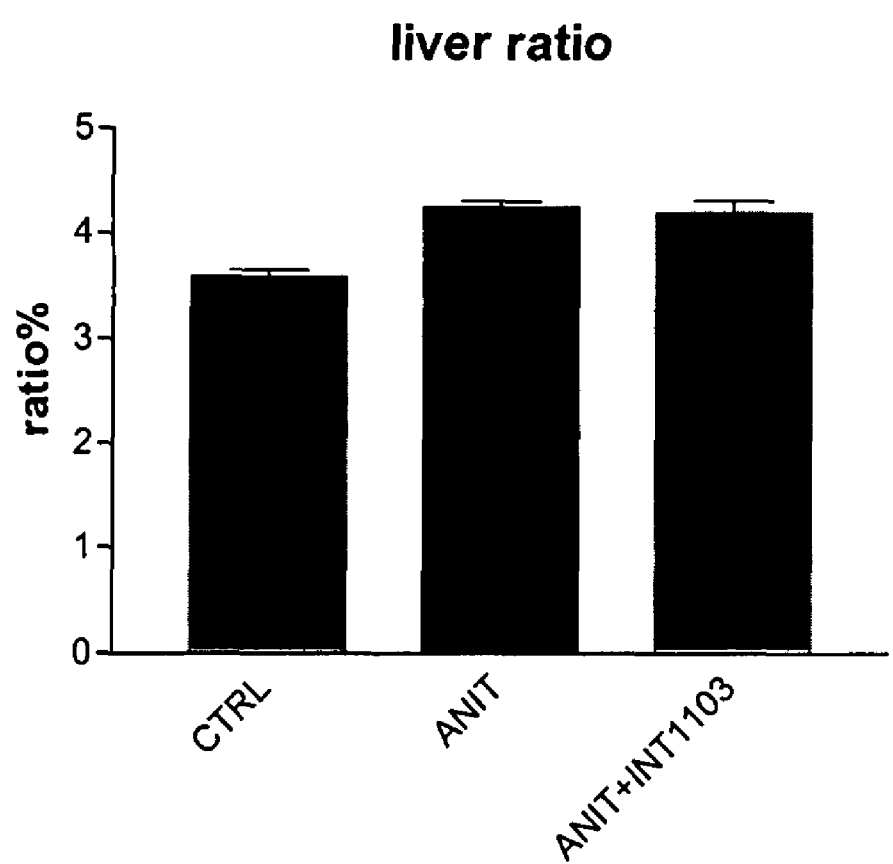
FIG. 23 shows the resulting liver ratio (liver weight/body weight×100).
Figure 24:
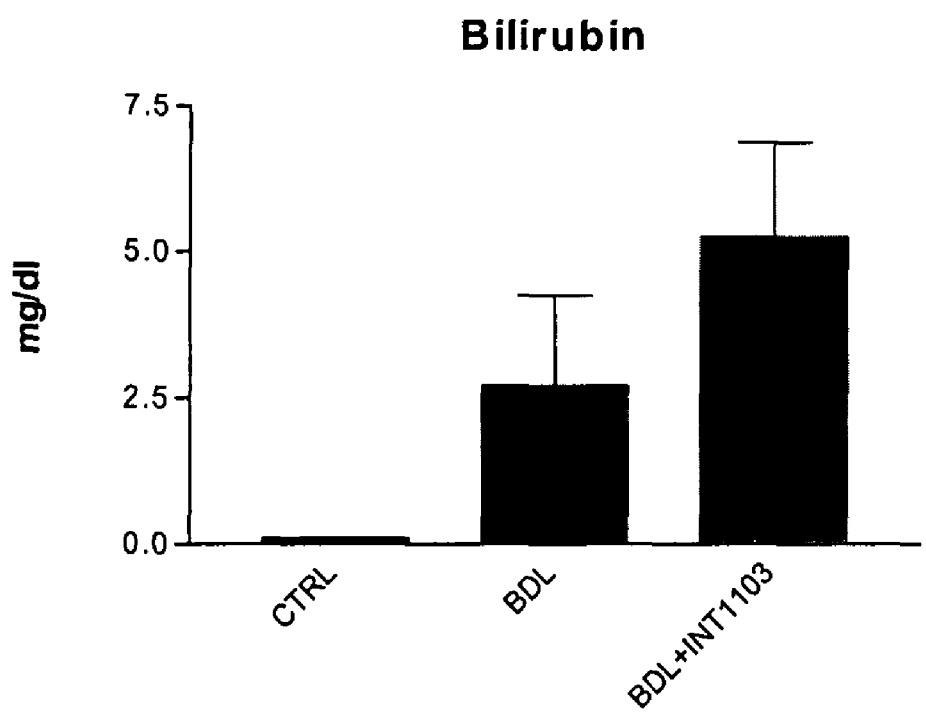
FIG. 24 shows the effect of INT-1103 on plasmatic bilirubin in BDL-induced cholestasic rats.
Figure 25:
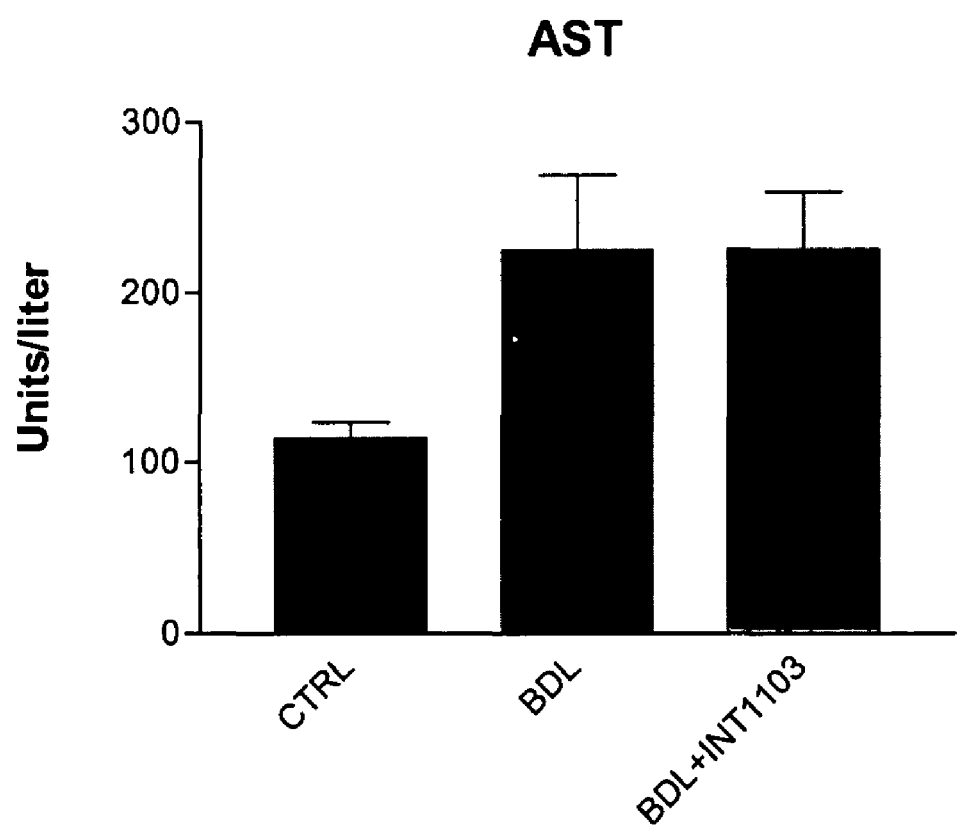
FIG. 25 shows the effect of INT-1103 on plasmatic AST in BDL-induced cholestasic rats.
Figure 26:
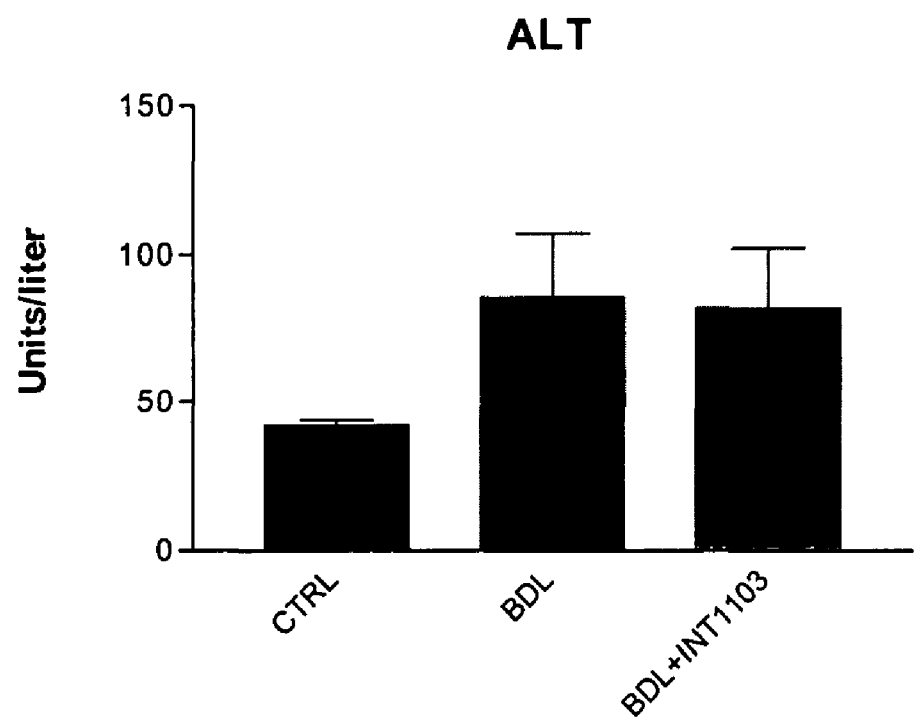
FIG. 26 shows the effect of INT-1103 on plasmatic ALT in BDL-induced cholestasic rats.
Figure 27:
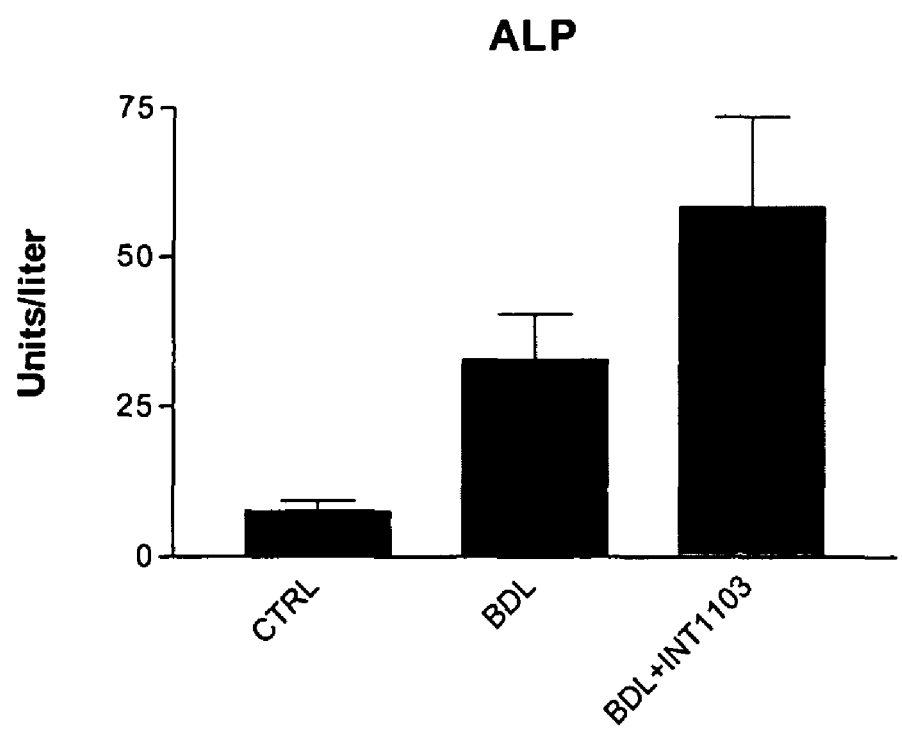
FIG. 27 shows the effect of INT-1103 on plasmatic ALP in BDL-induced cholestasic rats.
Figure 28:
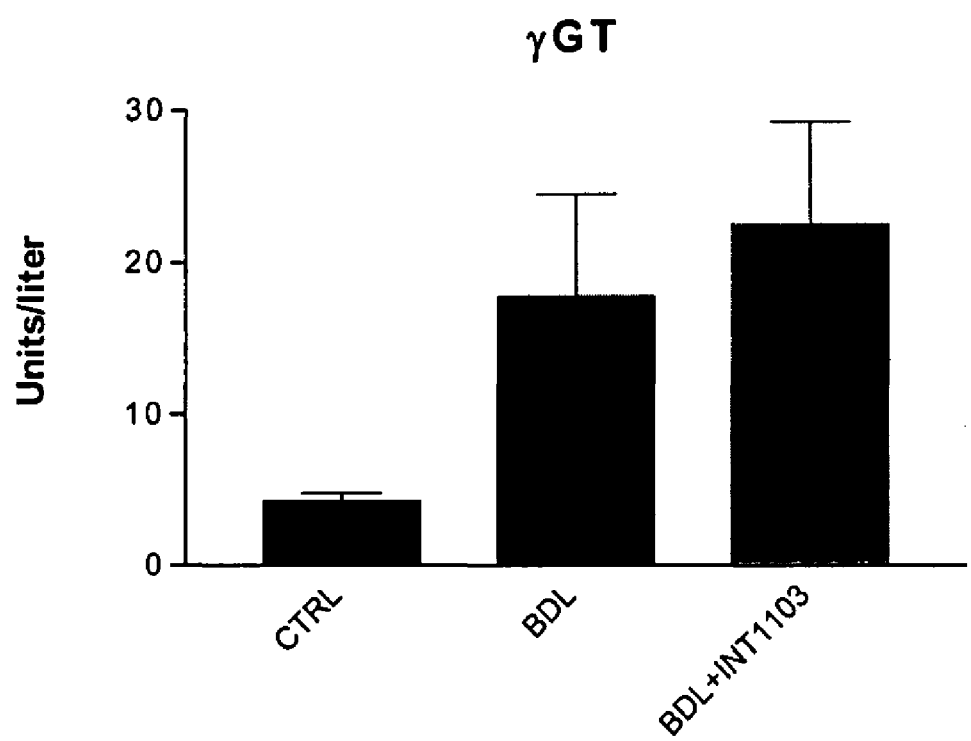
FIG. 28 shows the effect of INT-1103 on plasmatic gammaGT in BDL-induced cholestasic rats.
Figure 29:
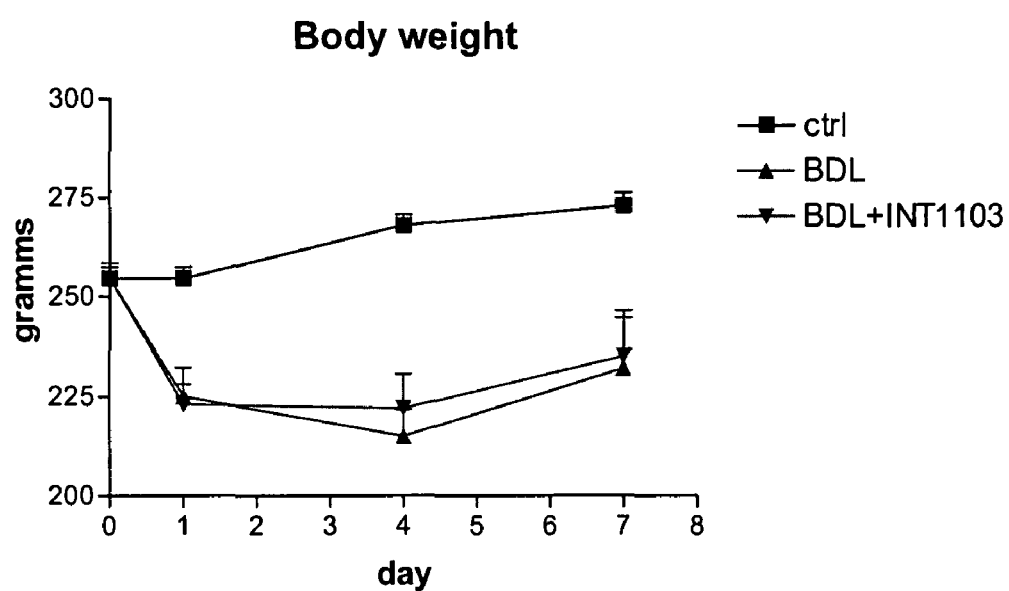
FIG. 29 shows the effect of INT-1103 on body weight in BDL-induced cholestasic rats.
Figure 30:
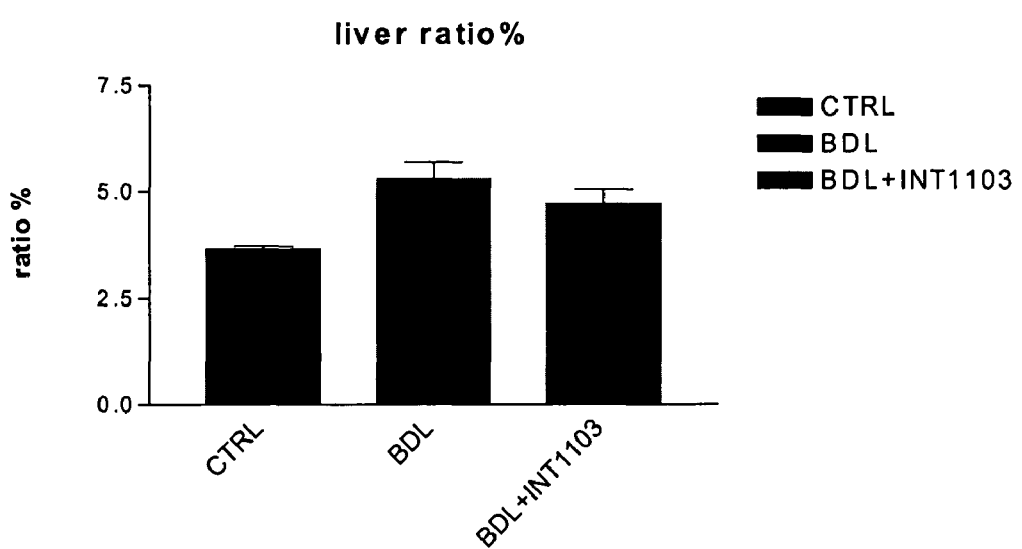
FIG. 30 shows the resulting liver ratio (liver weight/body weight×100).
Figure 31:
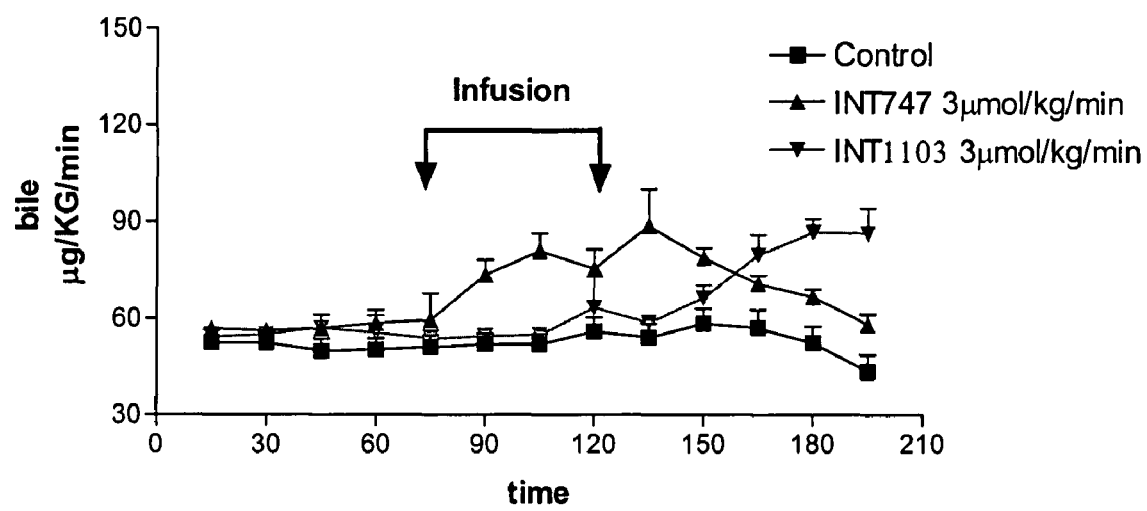
FIG. 31 shows the effect of INT-1103 and INT-747 on bile flow in naïve rats.
Figure 32:
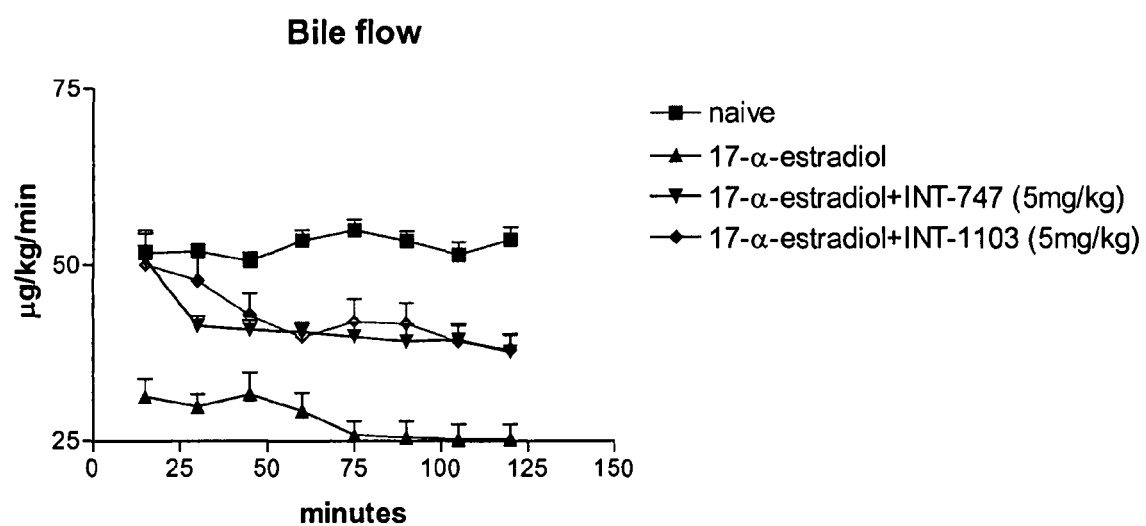
FIG. 32 shows the effect of INT-1103 and INT-747 on bile flow in estrogen colestatic rats.
Figure 33:
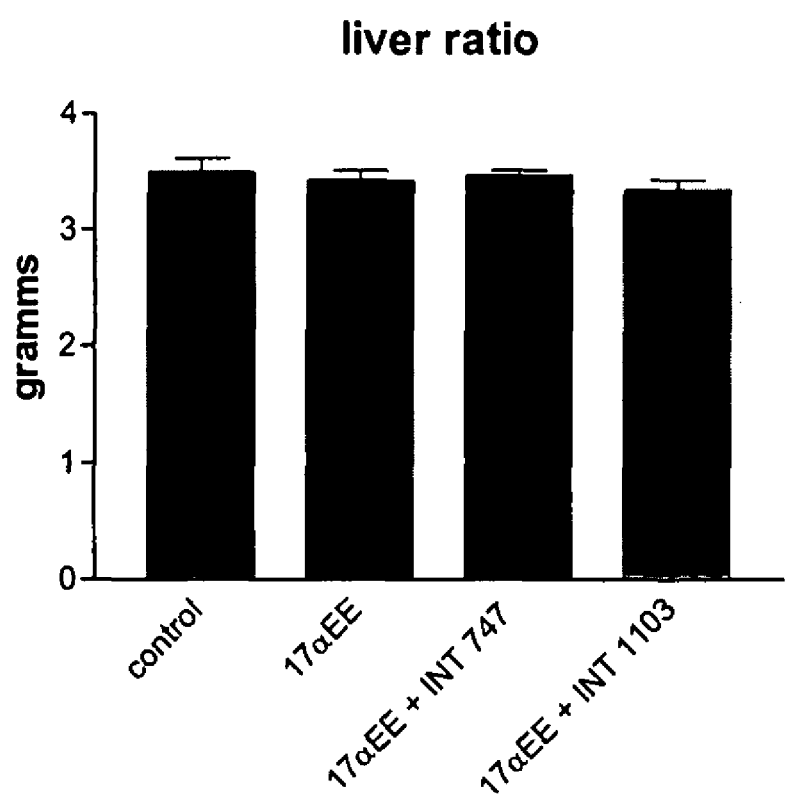
FIG. 33 shows the effect of INT-1103 and INT-747 on liver ratio in estrogen colestatic rats.
Figure 34:
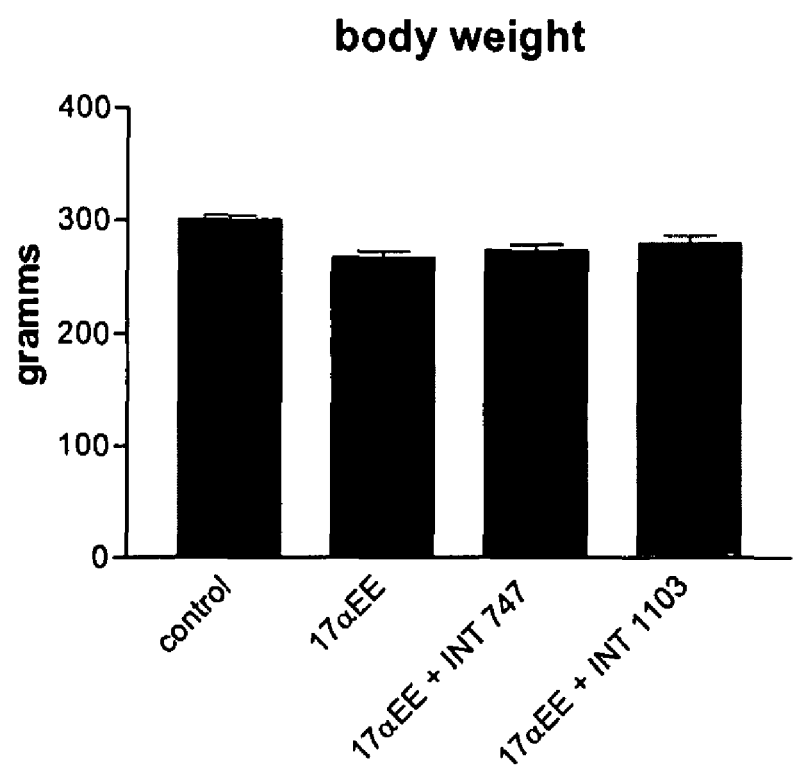
FIG. 34 shows the effect of INT-1103 and INT-747 on body weight in estrogen colestatic rats.
Figure 35:
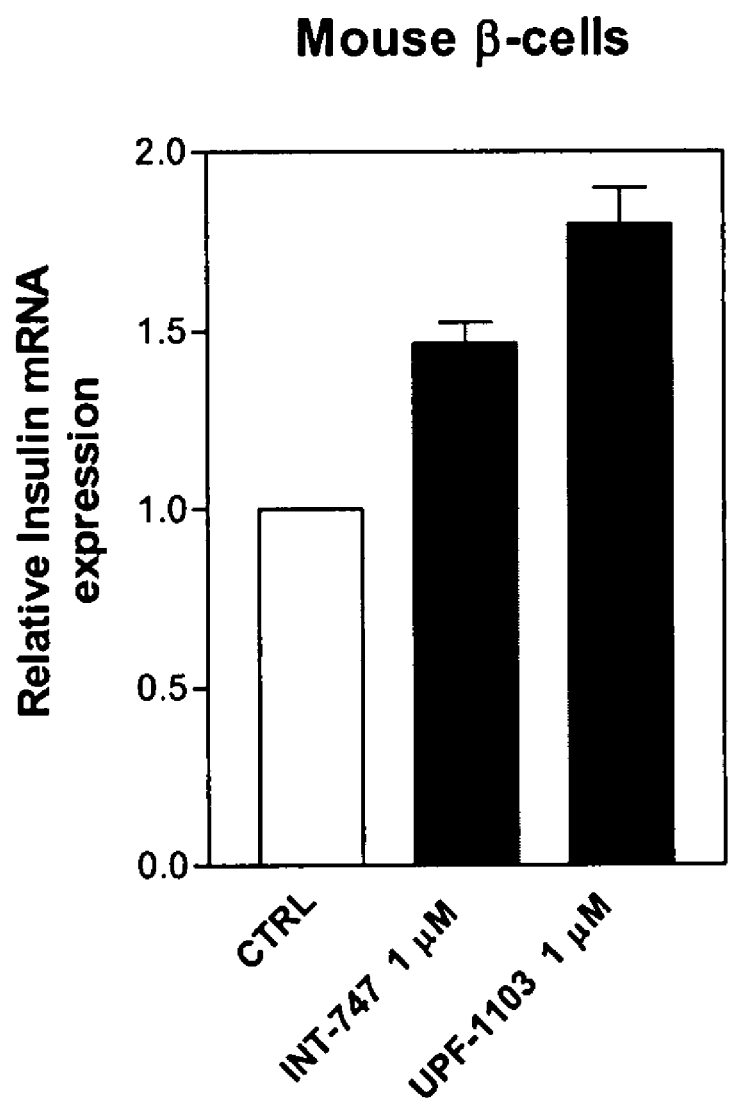
FIG. 35 shows the resulting insulin gene expression by Quantitative Real-Time PCR.
Figure 36:
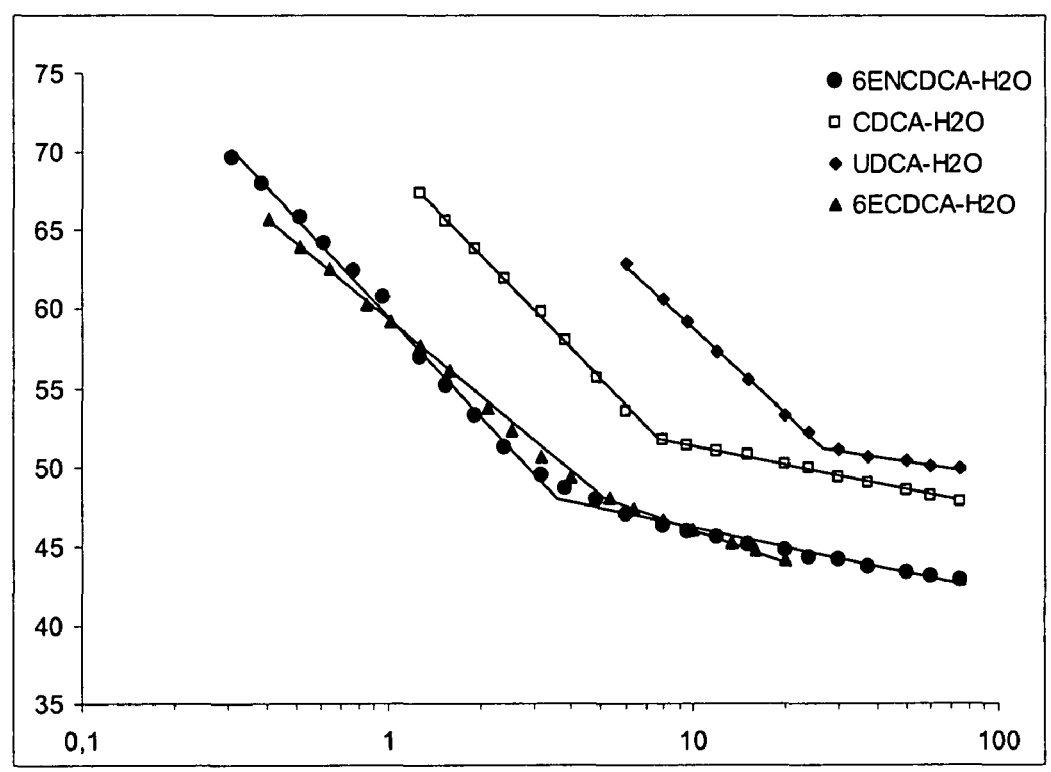
FIG. 36 shows the surface tension (dyne/cm) plotted against the logarithm of the bile salt concentration (mM) in water.

-continued mSREBP1c (SEQ ID NOS.: 19 & 20):
gatcaaagaggagccagtgc
and tagatggtggctgctgagtg Results In vivo administration of the UPF-987 to intact mice for 4 days at the dose of 5 mg/kg resulted in a potent induction of BSEP and SHP in the liver. Despite encouraging yet inconsistent target gene expression data with preliminary in vitro assays discussed above, the observed in vivo data suggest potent downregulation (60-70% reduction) of Cyp7a1. UPF-987 which also caused 90% inhibition of SREBP-1c and reduced FAS mRNA expression in the liver (FIG. 5).

Example 4

Evaluation of UPF-987 Anti-Inflammatory Activity in TNBS Mouse Model of Colitis

Materials and Methods
Colitis Models

The intracolonic application of the hapten TNBS causes acute and chronic colitis in rodents. Mucosal inflammation in TNBS-colitis has a prominent neutrophilic infiltrate, but also comprises influx of CCR1+ and CCR5+ macrophages and monocytes as well as a prominent IL-12 and IFN-dependent T lymphocyte (Th1) activation. Histopathological features resemble human Crohn's disease, transmural inflammation, granulomas, fissuring ulcers and "skip lesions" (regions of ulceration separated by regions of normal mucosa". TNBS-colitis serves as a useful pre-clinical model for testing established and innovative treatments for Crohn's disease.

Animals

Animals were monitored daily for appearance of diarrhea, loss of body weight, and survival. At the end of the experiment, surviving mice were sacrificed, blood samples collected by cardiac puncture, and a 7 cm segment of colon was excised, weighed, and macroscopic damage was evaluated.

Induction of Colitis and Study Design

Colitis was induced in BALB/c mice (8 weeks old) by intra-rectal administration of TNBS (0.5 mg/mouse) Beginning three hours later and continuing at 24-h intervals for five days, the mice were administered intra-peritoneally, UPF-987 (0.3-1-3 mg/kg) or vehicle (methyl cellulose 1%). Each group consisted of 5 or 7 mice. The mice were sacrificed 18 h after the final administration of the test drug or vehicle. The severity of colitis was scored by assessing the macroscopic appearance. The latter is an index of granulocyte infiltration in the tissue. The macroscopic scoring of colitis has been described in detail by Fiorucci et al, and involved blind scoring on a 0 (normal) to 4 (severe damage) scale. Body weight and stool consistency was recorded at the start and end of the study. Tissue samples were collected from the distal colon of each mouse and processed, as described previously.

Macroscopic Grading of Colitis

Colons were examined under a dissecting microscope (×5) and graded for macroscopic lesions on a scale from 0 to 10 based on criteria reflecting inflammation, such as hyperemia, thickening of the bowel, and the extent of ulceration.

Quantitative Real-Time PCR

Mouse colon genes expression was evaluated by quantitative real-time polymerase chain reaction (RT-PCR) like previously described. Total RNA was isolated from speciments taken from distal colon. Followed primers were designed using PRIMER3-OUTPUT software, using published sequence data from the NCBI database:

mGAPDH:
ctgagtatgtcgtggagtctac
and gttggtggtgcaggatgcattg mTNFα:
acggcatggatctcaaagac
and gtgggtgagcacgtagt mIL1β:
tcacagcagcacatcaacaa
and tgtcctcatcctcgaaggtc mIL6:
ccggagaggagacttcacag
and tccacgatttcccagagaac mINFγ:
gctttgcagctcttcctcat
and gtcaccatccttttgccagt miNOS:
acgagacggataggcagaga
and cacatgcaaggaagggaact mTGFβ1:
ttgcttcagctccacagaga
and tggttgtagagggcaaggac mFXR:
tgtgagggctgcaaaggttt
and acatccccatctctctgcac Example 5

Evaluation of Efficacy of UPF-987 in Rat Cholestatic Model (ANIT)

Background

Cholestasis results in intrahepatic accumulation of cytotoxic bile acids which cause liver injury ultimately leading to biliary fibrosis and cirrhosis. Cholestatic liver damage is counteracted by a variety of intrinsic hepatoprotective mechanisms. Such defense mechanisms include repression of hepatic bile acid uptake and de novo bile acid synthesis. Furthermore, phase I and II bile acid detoxification is induced rendering bile acids more hydrophilic. In addition to "orthograde" export via canalicular export systems, these compounds are also excreted via basolateral "alternative" export systems into the systemic circulation followed by renal elimination. Passive glomerular filtration of hydrophilic bile acids, active renal tubular secretion, and repression of tubular bile acid reabsorption facilitate renal bile acid elimination during cholestasis. The underlying molecular mechanisms are mediated mainly at a transcriptional level via a complex network involving nuclear receptors and other transcription factors. So far, the farnesoid X receptor FXR, pregnane X receptor PXR, and vitamin D receptor VDR have been identified as nuclear receptors for bile acids. However, the intrinsic adaptive response to bile acids cannot fully prevent liver injury in cholestasis. Therefore, additional therapeutic strategies such as targeted activation of nuclear receptors are needed to enhance the hepatic defense against toxic bile acids.

Materials and Methods

Animals

Wistar Rats studies were approved by the Animal Study Committee of the University of Perugia. Male Wistar rats (200-250 g) were obtained from Charles River Breeding Laboratories (Portage, Mich.) and maintained on standard laboratory rat chow on a 12-h light/dark cycle.

Colestatic Models: Method: Alpha-Naphthyl-Isothiocyanate (ANIT)

The first rats group (N=6) was treated, daily, by ANIT 100 mg/kg via gavage (colestatic inducer), the second and third groups (N=6) were treated by ANIT 100 mg/kg via gavage plus UPF-987 5 and 3 mg/kg intraperitoneally daily. Control rats (N=4) were administered vehicle (physiologic solution I.P.). At the end of the study, rats were sacrificed under anaesthesia with sodium pentobarbital (50 mg/kg i.p.) and terminally bled via cardiac puncture; the liver was removed and weighted for examination and blood samples were taken.

Quantitative Real-Time PCR

Rat genes expression was evaluated by quantitative real-time polymerase chain reaction (RT-PCR) as previously described herein. The following PCR primers (SEQ ID NOS.: 35-52) were designed using PRIMER3-OUTPUT software using published sequence data from the NCBI database:

```
rGAPDH (SEQ ID NOS.: 35 & 36):
atgactctacccacggcaag
and atgactctacccacggcaag rSHP (SEQ ID NOS.: 37 & 38):
cctggagcagccctcgtctcag
and aacactgtatgcaaaccgagga rBSEP (SEQ ID NOS.: 39 & 40):
aaggcaagaactcgagataccag
and tttcactttcaatgtccaccaac rCYP7A1 (SEQ ID NOS.: 41 & 42):
ctgcagcgagctttatccac
and cctgggttgctaagggactc rCYP8B1 (SEQ ID NOS.: 43 & 44):
ccctatctctcagtacacatgg
and gaccataaggaggacaaaggtct rNTCP (SEQ ID NOS.: 45 & 46):
gcatgatgccactcctcttatac
and tacatagtgtggccttttggact rMdr1 (SEQ ID NOS.: 47 & 48):
cgttgcctacatccaggttt
and gccattgcctgaaagaacat
```

```
rMdr2 (SEQ ID NOS.: 49 & 50):
gttctcgctggtcttcttgg
and cgtctgtggcgagtcttgta rMMP2 (SEQ ID NOS.: 51 & 52):
gatggatacccgtttgatgg
and tgaacaggaaggggaacttg
```

Results

UPF-987 was tested in vivo for its ability to protect against cholestasis induced in rat by α-naphthylisothiocyanate (ANIT). ANIT administration leads to a severe cholestasis, previous studies by Fiorucci et al. (unpublished) have shown that 6-ECDCA is not effective in reducing liver injury in this model. Administration of UPF-987 attenuates liver injury in ANIT treated rats, as measured by assessing plasma levels of AST, γGT and alkaline phosphatase, three markers of cholestasis and plasma cholesterol. In addition UPF-987, modulates NTCP, CYP7A1 and BSEP expression.

Example 6

Evaluation of Efficacy of INT-1103 in Rat Cholestatic Model (ANIT)

Background

INT-1103 is sulphide derivative of 6-ethyl-chenodeoxycholic acid (6E-CDCA or INT-747), which is disclosed and in U.S. Pat. No. 7,138,390 and incorporated by reference herein.

Material and Methods

Colestatic Models: Alpha-Naphthyl-Isothiocyanate (ANIT)

Wistar Rats

Studies were approved by the Animal Study Committee of the University of Perugia. Male Wistar rats (200-250 g) were obtained from Charles River Breeding Laboratories (Portage, Mich.) and maintained on standard laboratory rat chow on a 12-h light/dark cycle. The first group (N=8) were treated, daily, by ANIT 100 mg/kg via gavage (colestatic inducer), the second and third groups (N=8) were treated by ANIT 100 mg/kg via gavage plus INT-1103 5 mg/kg intraperitoneally daily. Control rats (N=8) were administered vehicle (physiologic solution I.P.). At the end of the study, rats were sacrificed under anaesthesia with sodium pentobarbital (50 mg/kg i.p.) and terminally bled via cardiac puncture; the liver was weighted and removed for examination and blood samples were taken.

Quantitative Real-Time PCR

The expression of rat FXR target genes was evaluated by quantitative real-time polymerase chain reaction (RT-PCR) as previously described herein. The following PCR primers (SEQ ID NOS.: 35-52) were designed using PRIMER3-OUTPUT software using published sequence data from the NCBI database:

```
rGAPDH (SEQ ID NOS.: 35 & 36):
atgactctacccacggcaag
and atgactctacccacggcaag rSHP (SEQ ID NOS.: 37 & 38):
cctggagcagccctcgtctcag
and
```

-continued

```
aacactgtatgcaaaccgagga rBSEP (SEQ ID NOS.: 39 & 40):
aaggcaagaactcgagataccag
and tttcactttcaatgtccaccaac rCYP7A1 (SEQ ID NOS.: 41 & 42):
ctgcagcgagctttatccac
and cctgggttgctaagggactc rCYP8B1 (SEQ ID NOS.: 43 & 44):
cccctatctctcagtacacatgg
and gaccataaggaggacaaaggtct rNTCP (SEQ ID NOS.: 45 & 46):
gcatgatgccactcctcttatac
and tacatagtgtggccttttggact rMdr1 (SEQ ID NOS.: 47 & 48):
cgttgcctacatccaggttt
and gccattgcctgaaagaacat rMdr2 (SEQ ID NOS.: 49 & 50):
gttctcgctggtcttcttgg
and cgtctgtggcgagtcttgta rMMP2 (SEQ ID NOS.: 51 & 52):
gatggatacccgtttgatgg
and tgaacaggaaggggaacttg
```

Example 7

Evaluation of Efficacy of INT-1103 in Rat Cholestatic Model (BTL)

Material and Methods

The (BTL) hepatic cholestatic model was induced by bile duct ligation (BDL) of 225-250 g old male Wistar rats. Sham-operated rats (N=8) received the same laparoscopic procedure, except that the bile duct was manipulated, but not ligated and sectioned. In total, 24 animals were operated. Three days after surgery, surviving rats were randomized to receive placebo, intraperitoneally, (fisiologic solution) (N=6) or INT-1103 5 mg/kg (N=8). Animals were then treated for 7 days. At the end of the study, rats were sacrificed under anaesthesia with sodium pentobarbital (50 mg/kg i.p.) and terminally bled via cardiac puncture; the liver was weighted and removed for examination and blood samples were taken.

Example 8

Evaluation of Efficacy of INT-1103 and INT-747 in Bile Flow on Naïve Rat

Material and Methods

Adult male Wistar rats weighing 200 to 250 g were used throughout the study. Before the experiments, the animals were maintained on standard chow and water ad libitum and housed in a temperature (21-23° C.)- and humidity (45-50%)-controlled room under a 12-h light/dark cycle. All studies were approved by the Animal Study Committee of the University of Perugia. For bile flow measurement, animals were anesthetized with a single dose of sodium pentobarbital (50 mg/kg body wt intraperitoneally) and maintained under this condition throughout the experiment. After catheterization of the jugular vein using a PE-50 polyethylene tubing (Intramedic; Clay Adams, Parsippany, N.J.), a middle abdominal incision was made, and the common bile duct was also cannulated (PE-10, Intramedic; Clay Adams). Body temperature was maintained at 37.0 to 38.5° C. with a warming lamp to prevent hypothermic alterations of bile flow. The bile samples were collected by the external biliary fistula every 15 min for 195 min and then weighed in order to determine the bile flow. Bile flow was determined by gravimetry, assuming a density of the bile of 1.0 g/ml. Bile collection started between 9:00 and 11:00 AM to minimize influence of circadian variations. Drugs administration was done by jugular cannula at the doses of 3 μmoli/kg/min, control group received vehicle alone (BSA 2% on fisilogic solution).

Example 9

Evaluation of Efficacy of INT-1103 and INT-747 in Bile Flow on Estrogen Colestatic Rat Material and Methods Adult male Wistar rats weighing 300 to 350 g were used throughout the study. Before the experiments, the animals were maintained on standard chow and water ad libitum and housed in a temperature (21-23° C.)- and humidity (45-50%)-controlled room under a 12-h light/dark cycle. All studies were approved by the Animal Study Committee of the University of Perugia. Animals were randomly divided into 4 experimental groups
1. Naïve, (N=5).
2. 17-ethynylestradiol 5 mg/kg for 5 days intra-peritoneal, (N=8).
3. 17-ethynylestradiol 5 mg/kg+INT-747 5 mg/kg intra-peritoneal, for 5 days (N=7);
4. 17-ethynylestradiol 5 mg/kg+INT-1103 5 mg/kg intra-peritoneal, for 5 days (N=7).

For bile collection, surgical procedures were made on the sixth day (1 day after the administration of the last dose of E217). For bile flow measurement, animals were anesthetized with a single dose of sodium pentobarbital (50 mg/kg body wt intraperitoneally) and maintained under this condition throughout the experiment. A middle abdominal incision was made, and the common bile duct was also cannulated (PE-10, Intramedic; Clay Adams). Body temperature was maintained at 37.0 to 38.5° C. with a warming lamp to prevent hypothermic alterations of bile flow. Bile collection started between 9:00 and 11:00 AM to minimize influence of circadian variations. Bile was collected at 15-min intervals for 120 min, and bile flow was determined gravimetrically. At the end of the experiments the body and liver rats was weighted.

Example 10

In Vitro Study of Insulin Gene Regulation by INT-747 vs INT-1103

Material and Methods

For RT-PCR assay, pancreatic Beta-TC6 cells were cultured in D-MEM supplemented with 1% penicillin/streptomycin, 1% L-glutamine and 10% fetal bovine serum (high glucose) (CELBIO). Cells were grown at 37° C. in 5% CO2 and treated with INT-1103 and INT-747, at the final concentration 1 μM, for 18 hours. At the and of the experiments the cells were collected for RNA extraction.

Real Time PCR

Quantification of the expression of mouse genes was performed by quantitative real-time polymerase chain reaction (RT-PCR). All PCR primers were designed using PRIMER3-OUTPUT software using published sequence data from the NCBI database. Total RNA was isolated (TRIzol reagen, Invitrogen srl, Milan, Italy) from speciments taken from livers. One microgram of purified RNA was treated with DNAse I for 10 minutes at room temperature, followed by incubation at 95° C. for 3 minutes in the presence of 2.5 mmol/L EDTA. The RNA was reverse transcribed with Superscript III (Invitrogen, Carsbad, Calif.) in 20 μL reaction volume using random primers. For quantitative RT-PCR, 100 ng template was dissolved in a 25 μL containing 0.3 μmol/L of each primer and 12.5 μL of 2×SYBR Green PCR Master mix (Fynnzimes-DyNAmo SYBRR Green qPCR mix). All reactions were performed in triplicate, and the thermal cycling conditions were as follows: 2 minutes at 95° C., followed by 50 cycles of 95° C. for 20 seconds, 55° C. for 20 seconds and 72° C. for 30 seconds on iCycler iQ instrument (Bio-Rad, Hercules, Calif.). The mean value of the replicates for each sample was calculated and expressed as the cycle threshold (CT; cycle number at which each PCR reaction reaches a predetermined fluorescent threshold, set within the linear range of all reactions). The amount of gene expression was then calculated as the difference (ΔCT) between the CT value of the sample for the target gene and the mean CT value of that sample for the endogenous control (GAPDH). Relative expression was calculated as the difference (ΔΔCT) between ΔCT values of the test control sample for each target gene. The relative mRNA expression was shown as $2^{-\Delta\Delta CT}$. The Primers used in Real-Time PCR were:

```
mGAPDH (SEQ ID NOS.: 53 & 54):
gaaggtgaaggtcggagt
and catgggtggaatcatattggaa;

Mshp (SEQ ID NOS.: 55 & 56):
gctgtctggagtccttctgg
and ccaatgatagggcgaaagaagag;

mSREBP1c (SEQ ID NOS.: 57 & 58):
gcaaggccatcgactacatt
and ggtcagtgtgtcctccacct.

mINS (SEQ ID NOS.: 59 & 60):
tgttggtgcacttcctaccc
and ttgttccacttgtgggtcct mSHP (SEQ ID NOS.: 61 & 62):
aagggcttgctggacagtta
and tctcttcttcctccctatca mGLUT2 (SEQ ID NOS.: 63 & 64):
ccctgggtactcttcaccaa
and gccaagtaggatgtgccaat
```

Example 11

Physico-Chemical Properties of INT-747 and INT-1103

Background

The two bile acid analogues, INT-747 and INT-1103, were admitted to a complete physico-chemical properties characterization following protocols previously developed and optimized in our laboratory and previously applied for a complete screening of a large series of Bile acid analogues (UDCA analogues) developed in the R. Pellicciari lab. The physico-chemical properties were selected to accurately define the behaviour in aqueous solutions and in biological fluids and to establish their potential toxicity to biological membranes, their pharmacokinetics and pharmacodynamics and biodistribution in the different biological fluids and organs. Comparative data with natural analogues will be also performed and discussed.

Water Solubility

Only side chain carboxylated BA INT-747, CDCA and UDCA were studied. Solid BA were suspended in 5 ml of 0.1 M HCl. The saturated solutions, after incubation for 1 week, were filtered on a Millipore filter (0.22 μm) and the concentration of BA was measured by HPLC-ESI-MS/MS using C18 column (150 mm×2 mm i.d., 4 μm) and mobile phases of water containing 15 mM acetic acid pH 5 and acetonitrile. The flow rate was 150 μl/min. The mass spectrometry acquisition was performed in the multiple reaction monitoring mode using the ESI source in negative ionization. Water solubility was expressed as μmol/liter

TABLE 3 water solubility of the studied bile acids

| Bile Acid | Water Solubility (μM)* |
|---|---|
| INT-747 | 9.0 |
| INT-103 | — |
| CDCA | 32 |
| UDCA | 7.5 |

*water solubility refers to BA as protonated species and therefore not evaluated for INT-1103

The water solubility was measured for the insoluble protonated species of carboxylated bile acids at a pH 1. The sulphate compound, UPF 1103 is ionized even at low pH and in physiological conditions is always soluble in all biological fluids. The water solubility of INT-747 is 9 μM, lower than CDCA, and comparable with that of UDCA. Since the CMC of INT-747 is relatively low (see next paragraph), the low water solubility of INT-747 do not compromise the behaviour of the compound in a micellar phase; in the case of UDCA, the low water solubility associated with an high CMC compromises the pH at which the protonated acid goes in solution to form micelles. The CMpH is, in fact, for UDCA 8.4, which is too high if is not present a postprandial alkalinization in duodenal content.

Critical Micellar Concentration (CMC)

This value was determined by surface tension measurements using a maximum bubble-pressure method. The tensiometer was a Sensadyne 6000 (Chem-Dyne Research Corp., Milwaukee, Wis.) equipped with two glass probes of 0.5 and 4.0 mm diameters connected to a source of nitrogen. The bubble frequency was 1 bubble/second in distilled water at 26° C. (P=2.7 atm) and the calibration was made with double-distilled water and methanol. The surface tension of BA sodium salts solutions both in water and in NaCl 0.15 M was measured at various concentrations range, 0.2-75 mM and 0.3-100 mM respectively. The surface tension values were plotted against the logarithm of the bile salt concentration; the regression lines corresponding to the two parts of the curve (monomeric and micellar phases) were calculated using the method of least squares, and the intersection of the lines was taken as the CMC value.

TABLE 4

Critical Micellar Concentration of the studied bile acids

| Bile Acid | CMC (mM) | | $ST_{CMC}$ Dyne/cm | $ST_{50}$ Dyne/cm |
|---|---|---|---|---|
| | $H_2O$ | NaCl 0.15 M | | |
| INT-747 | 4.5 | 2.9 | 48.8 | 43.2 |
| INT-1103 | 3.9 | 1.3 | 47.9 | 43.3 |
| CDCA | 7.5 | 3.0 | 55.6 | 48.5 |
| UDCA | 26 | 6.0 | 63.0 | 50.4 |
| TUDCA | 8.0* | 2.2* | — | — |
| TCDCA | 7.0* | 3.0* | — | — |

$ST_{CMC}$: Surface Tension at CMC in water, ST50: Surface Tension of 50 mM aqueous solution;
*values from literature The CMC, as evaluated by surface tension measurements in non equilibrium conditions i.e. in conditions that impurities do not affect the results, of INT-747 and INT-1103 are relatively low, similar to CDCA natural analogue. INT-1103 presents the lower CMC both in water and in presence of counter ion Na+ 150 mM. The low CMC value of INT-747 is related to the topographic distribution of the ethyl and hydroxyl groups: the ethyl group in the 6 position is oriented in the P face, the back of the steroid, contributing to increase the lipophilic extent and area of the surface of this moiety and therefore the tendency to form micelles. INT-1103 presents the lower CMC as result of ethyl group in 6 position and the 23 sulphate in the side chain. The peculiar properties of the sulphate group gave to INT-1103 anionic surfactant like properties (like sodium dodecyl sulphate) as a result of a negative charged head and lipophilic tail with a surface lipophilic moiety. The values of the surface tension activity both at CMC and in micellar phase (50 mM) agree with the present CMC data, both compounds are surface active and able to lower the surface tension to a great extent in respect to UDCA and TUDCA. This data further supports the concept that this compounds are detergent like the CDCA analogue and even more. INT-747 at a relatively high concentration>60 mM and in the presence of Na+ 0.15 M form a gel phase and this account for the relatively inaccurate ST data found in that conditions (FIG. 1) These results are not surprising since other detergent natural BA like deoxycholic acid behave similarly forming this gel (usually viscoelastic) particularly for the effect of counter ions like Na+ and Ca++ This phase evolves to micellar phase with a relatively low kinetics. Moreover this phenomenon occurs at a very high not physiological concentration.

Octanol/Water Partition Coefficient

1-Octanol/water partition coefficient (log P) was evaluated using a conventional shake-flask procedure. The experiments were carried out on 0.1 mM bile salt solution buffered at pH 8 with 0.1 M phosphate buffer to ensure complete ionization of the BA; the log P values refer to the BA in the ionized form, not to the protonated species, and the initial concentration of each BA was below its own CMC value. The aqueous buffer was previously pre-saturated with 1-octanol, 5 ml of 1-octanol pre-saturated with water was then added and the samples were left to equilibrate for 2 weeks under continuous stirring at room temperature After centrifugation the two phases were carefully separated. BA concentration in the water phase was measured with HPLC-ESI-MS/MS using C18 column (150 mm×2 mm i.d., 4 µm) and mobile phases: A: water containing 15 mM acetic acid pH 5, B: acetonitrile. The flow rate was 150 µl/min and the column was maintained at 45° C. The mass spectrometry acquisition was performed in the multiple reaction monitoring mode using the ESI source in negative ionization.

TABLE 5

1-octanol-water partition coefficient of the studied bile acids as ionized species

| Bile Acid | $LogP_A^-$ |
|---|---|
| INT-747 | 2.5 |
| INT-1103 | 2.0 |
| CDCA | 2.2 |
| UDCA | 2.2 |
| TCDCA | 0.9 |
| TUDCA | 1.0* |

*value from literature

The 1-octanol/water partition coefficient was calculated for the ionized species to facilitate the comparison between the carboxyl and sulphate bile acids since the latter do not protonated even at very low pH. INT-747 presents a slightly higher lipophilicity in respect to other dihydroxy bile acids such as UDCA and CDCA. The increased lipophilicity is the result of the introduction of an ethyl group in position 6. The tendency to distribute in a lipid domain is therefore higher. The UPF 1103 shows a log P of 2.0, value slightly lower than INT-747 and natural CDCA and UDCA analogues and this account for the contribution of the sulphate group and side chain length. Moreover the lipophilicity of INT-1103 is still similar to an unconjugated BA and higher than taurine conjugated like TCDCA that present a log P of 0.9. Contrarily to Taurine conjugate which preferentially stay in a water domain, INT-1103 has a tendency to accumulate in a lipid domain like INT-747.

Albumin Binding

Albumin binding was evaluated by equilibrium dialysis at a fixed BA-albumin ratio. BA was dissolved at a concentration of 100 µM in 5% bovine serum albumin-saline solution and left to stand for 24 h at 25° C. Two ml of this solution was dialyzed in cellulose sacs having a molecular weight cut-off of 12-14,000 against 25 ml of saline solution. The system was equilibrated by mechanical shaking for 72 h at 25° C. BA concentrations of the dialyzed solution and of the starting solution were determined with HPLC-ESI-MS/MS in the same conditions of the previous analysis.

TABLE 6

Albumin binding of the studied bile acids

| Bile Acid | % Binding |
|---|---|
| INT-747 | 96 |
| INT1103 | 85 |
| CDCA | 93 |
| UDCA | 94 |
| TUDCA | 67 |
| CA | 40* |

*values from literature

Both INT-747 and UPF 1103 present a strong interaction with albumin quite similar to natural dihydroxy bile acid like CDCA and UDCA suggesting a similar kinetic in the hepatic uptake. Trihydroxy bile acids like cholic acid or taurine conjugated bile acids show a lower interaction with albumin and this account to the lower serum concentration at a similar intestinal uptake as a result of a higher first pass clearance. The unbound fraction (like for many drugs) modulates the liver uptake: as the fraction increase the higher is the uptake. INT-747 and INT-1103 present a low unbound fraction and therefore their serum concentration are higher as a result of a relatively low first pass clearance, and their behaviour is similar to natural analogs.

Critical Micellar pH

This value can be experimentally determined by evaluating the pH at which a given BA starts to precipitate from a micellar solution. It can be calculated from the CMC Water solubility of the protonated species and pKa using the formula: CMpH=pKa+log CMC/WS. The CMpH of the studied compounds in comparison with the natural analogs are reported in Table 1.

TABLE 7

Critical Micellar pH the studied bile acids

| Bile Acid | CMpH |
|---|---|
| UPF 747 | 7.7 |
| UPF1103 | — |
| CDCA | 7.6 |
| UDCA | 8.4 |
| TCDCA | — |

The CMpH value of INT747 is similar to that of CDCA and lower to UDCA. According to this value INT747 do not present problems of intestinal solubility and requires a pH of 7.6 which is physiological to go in solution. For example UDCA with a CMpH of 8.4 requires an higher alkalinization of the duodenal content and only in post-prandial phase is solubilized in a micellar phase. UP 1103 having a sulphate group do not present these problems since is always soluble in the physiological pH from 2 to 9 since the pKa is very low and the compound do not protonated to form insoluble molecule. Its behaviour is similar to taurine conjugated bile acids.

Example 12

Hepatic Metabolism and Secretion of INT-747 and INT-1103 in Rat after One Hour iv Infusion at a Dose of 3 umol/Kg/min Background The BA were administered by infusion to bile fistula rat and bile collected at 15 min intervals for 7 hours. The bile flow was measured and bile analyzed using HPLC-ES-MS-MS for the identification of the rate of biliary secretion and to evaluate the major hepatic metabolites.

HPLC-ES-MS/MS Method

Bile acids and their metabolites were determined by a liquid chromatography-tandem mass spectrometry (HPLC-MS/MS) method using electrospray (ESI) source in negative ionization mode. Rat bile samples were brought to room temperature and diluted 1:100 v/v-1:1000 v/v with 15 mM ammonium acetate buffer (pH=5). Then, 10 μL were injected into the chromatographic column. Liquid chromatography was performed using a Waters Alliance 2695 separation module coupled with autosampler. Bile acids were analyzed using a Synergi Hydro-RP C18 column (150×2.0 mm i.d., 4 μm particle size), protected by a SecurityGuard ODS 4×2.0 mm i.d. precolumn, both supplied from Phenomenex. Bile acids were separated in elution gradient using 15 mM ammonium acetate buffer (pH=5.00) as mobile phase A and acetonitrile as mobile phase B. Mobile phase B was increased from 30% to 64% in 12 min, then to 70% in 8 min, and finally brought to 100% in 10 min and held constant for 1 min. Flow rate was 150 μL/min and the column was maintained at 45° C. The column effluent was analysed by ESI-MS/MS using a Quattro-LC (Micromass) triple quadruple mass spectrometer operating in Multiple Reaction Monitoring (MRM) acquisition mode. MassLynx software version 4.0 was used for data acquisition and processing.

Results

INT-747 is secreted into bile mainly as taurine conjugate and its recovery is almost complete: at the administered dose more than 99% of the infused molecule is secreted into bile as shown in FIG. 3. At the last point of bile collection a relatively high amount of the taurine conj. compound is still secreted in bile. The maximum secretion rate is achieved after 120 minutes just at the end of the infusion. A steady state concentration is maintained for additional 30 minutes. The taurine conjugation process begin very early and appears efficient at the administered dose. Trace amount of the compound is also conjugate with glycine, less than 0.2% and similar amount is secreted as such in bile. The behaviour of INT-747 is similar to that of natural dihydroxy analogs such as CDCA or UDCA which are secreted into bile only as taurine and glycine conjugates. Differently, trihydroxy BA such as CA, can be also partially secreted in unconjugated form. The extent of a BA that can be secreted unmodified is related to its lipophilicity and is dose and species dependent.

Figure 37:
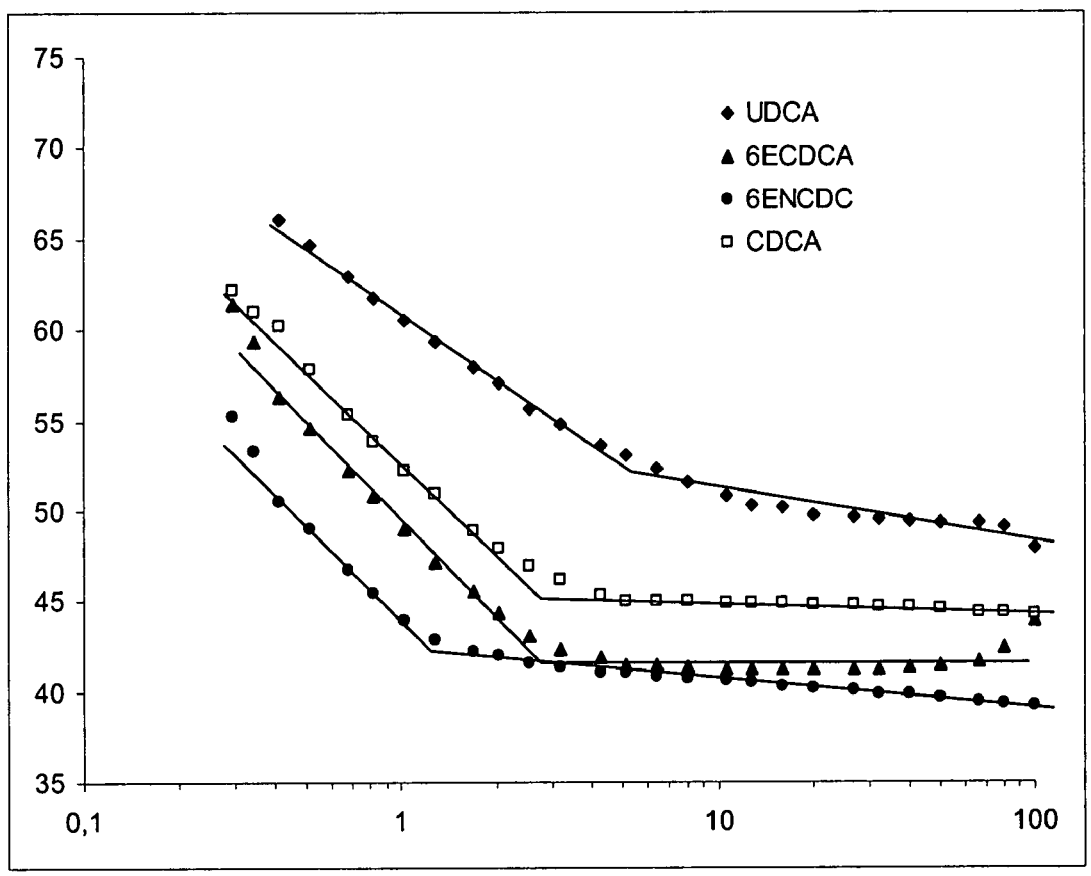
FIG. 37 shows the surface tension (dyne/cm) plotted against the logarithm of the bile salt concentration (mM) in NaCl 0.15 M.
Figure 38:
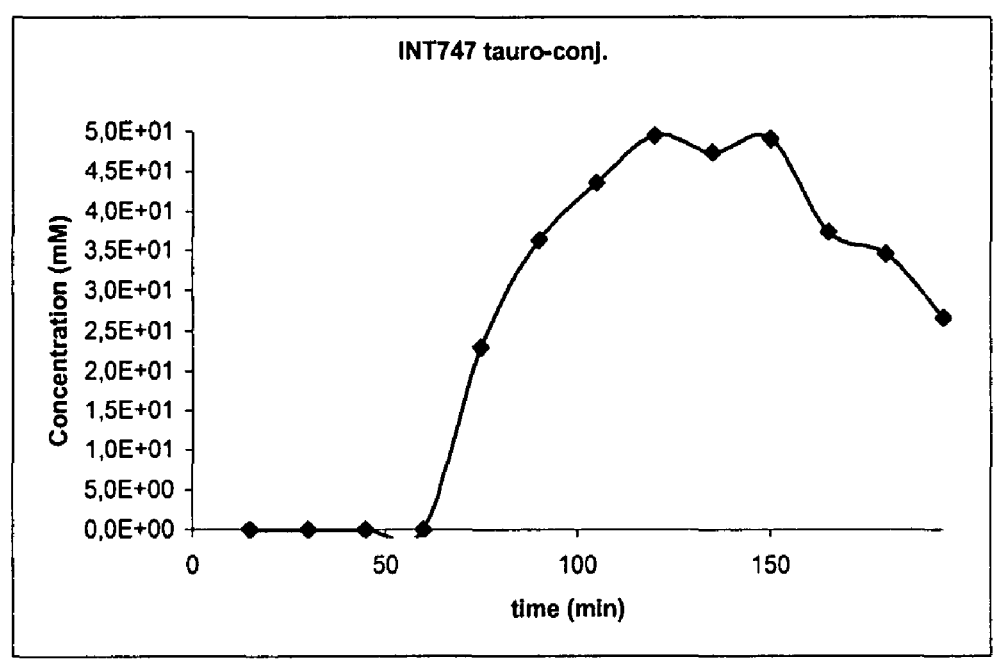
FIG. 38 shows the secretion rate of taurine conjugated INT-747. Data are reported as concentration in bile and should be corrected by the bile volume.
Figure 39:
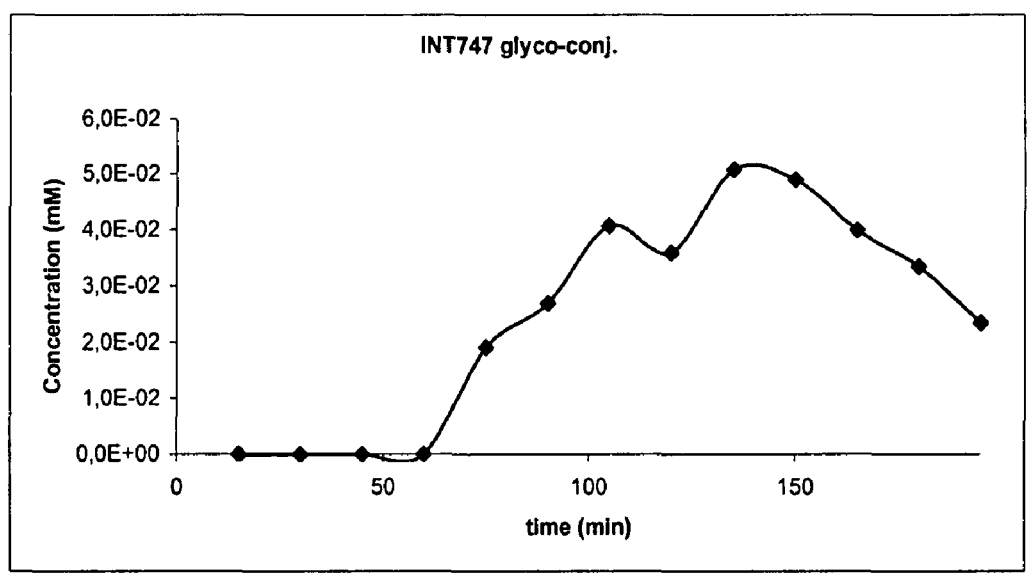
FIG. 39 shows the secretion rate of glycine conjugated INT-747. Data are reported as concentration in bile and should be corrected by the bile volume.
Figure 40:
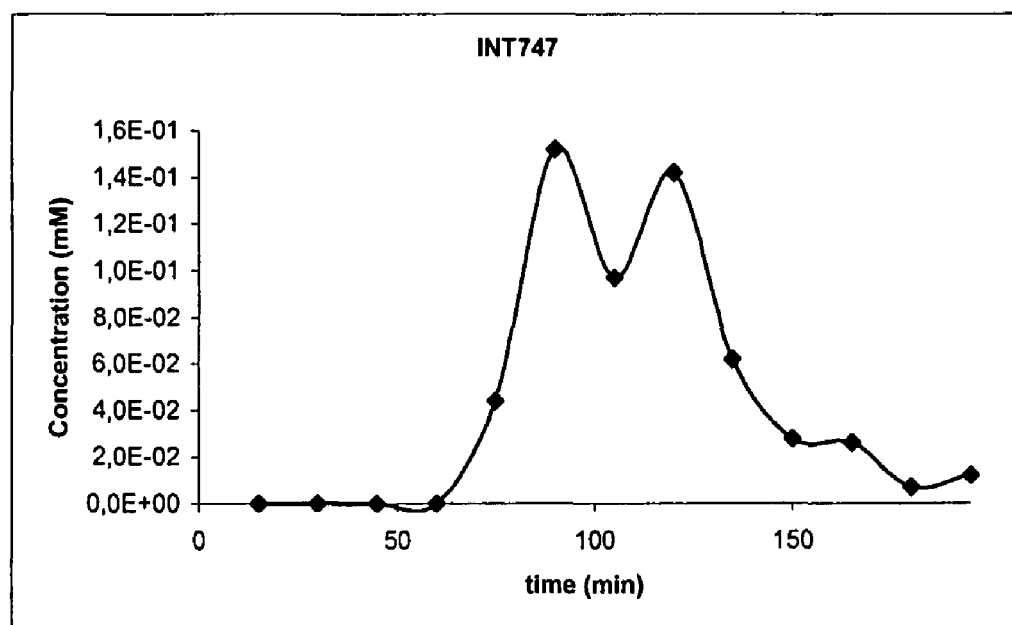
FIG. 40 shows the secretion rate of INT-747. Data are reported as concentration in bile and should be corrected by the bile volume.

The behaviour in term of hepatic uptake and secretion of this molecule is quite similar to natural analogue like CDCA and the rate of hepatic secretion is related to that of taurine conjugation mediated by a CoA activation and taurine liver availability. The preferential conjugation with taurine is peculiar to rat and other species (dog, mice, . . . ) and in man this compound is amidated mainly with glycine. According to these date seems that INT-747 is efficiently take up and secreted by the liver. The hepatic metabolism of INT-747 produces mainly the taurine conjugate form. Trace amount of glycine conjugate are secreted in bile and also very low amount is secreted as such. (FIGS. 37 and 38). Minor epimers of both unconjugated and taurine conjugated are present in bile (FIGS. 39 and 40).

Figure 41:
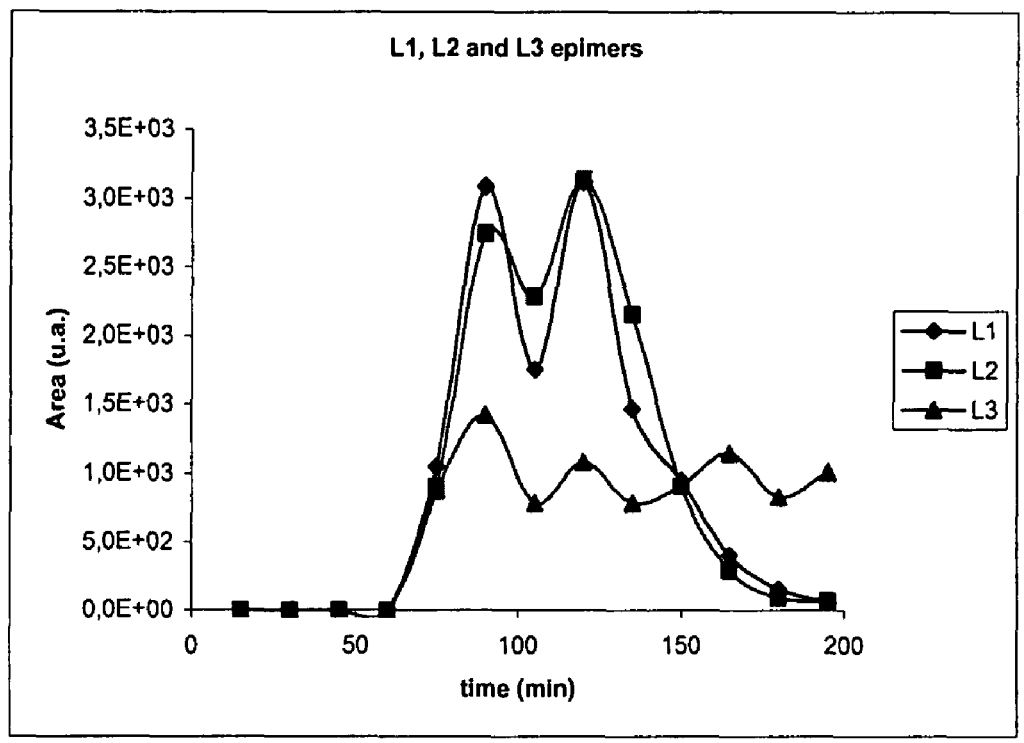
FIG. 41 shows the secretion rate of INT-747 epimers. Data are reported as concentration in bile and should be corrected by the bile volume.
Figure 42:
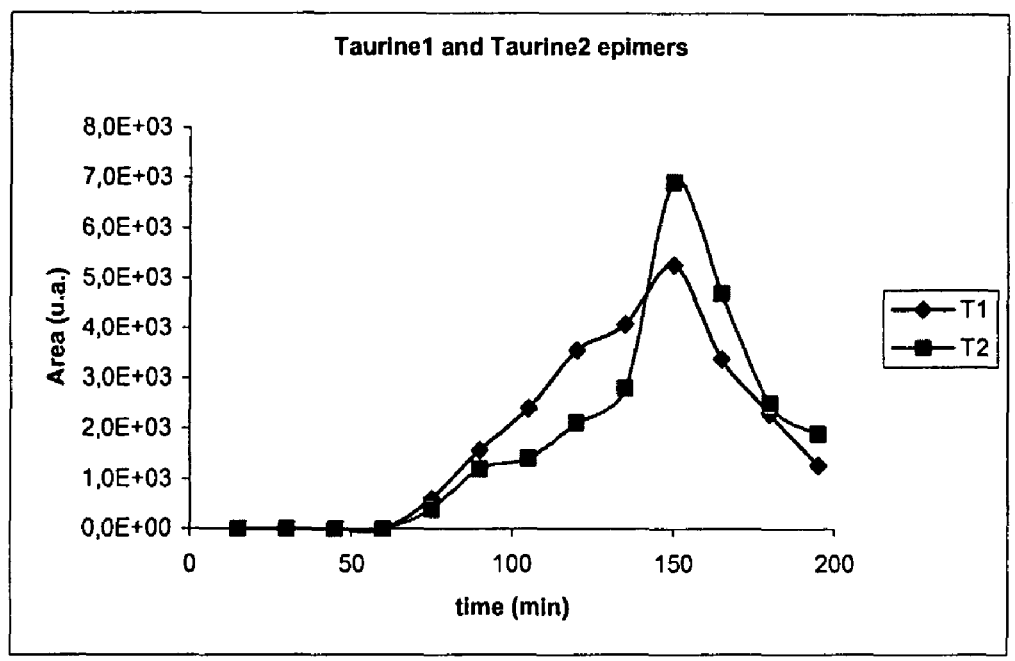
FIG. 42 shows the secretion rate of taurine conjugated epimers of INT-747. Data are reported as concentration in bile and should be corrected by the bile volume.
Figure 43:
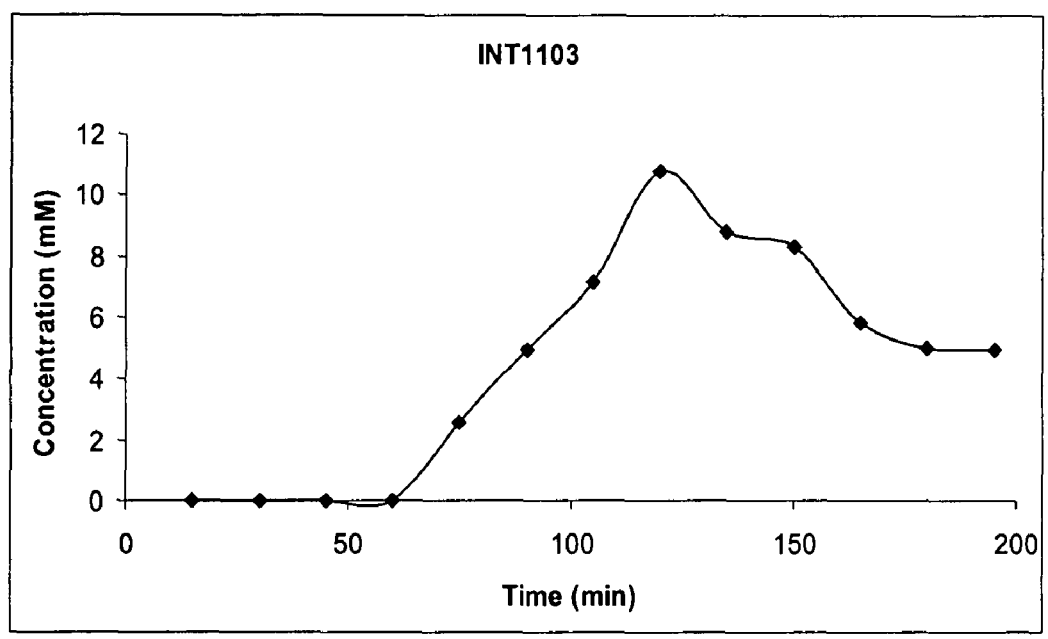
FIG. 43 shows the secretion rate of INT-1103. Data are reported as concentration in bile and should be corrected by the bile volume.
Figure 44:
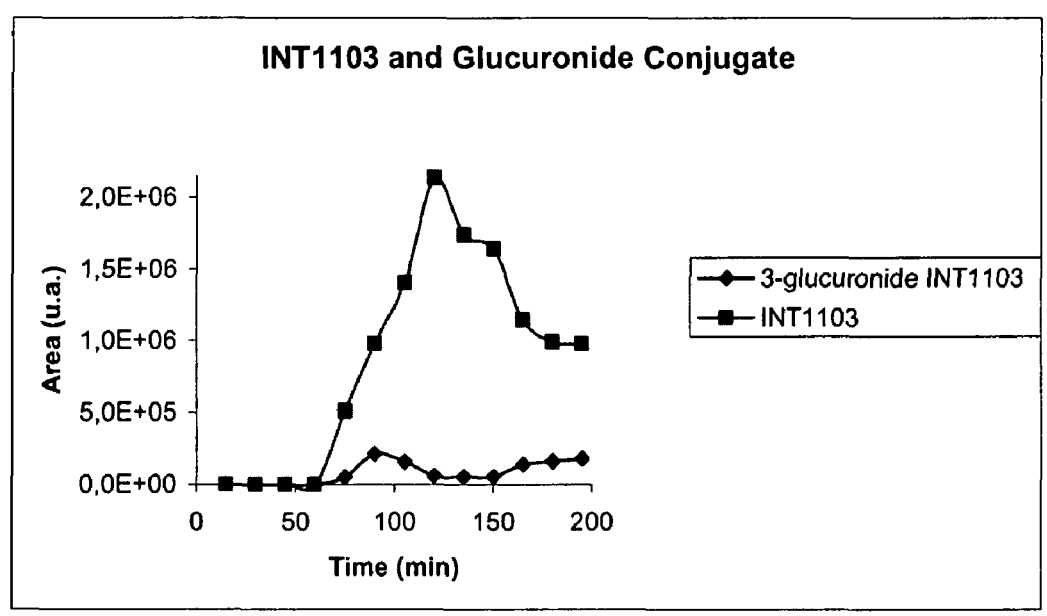
FIG. 44 shows the secretion rate of INT-1103 and its main metabolite 3-Glucuronides. The relative amount are expressed as analytical signal. Data are reported as concentration in bile and should be corrected by the bile volume.

INT-1103 is secreted in bile partially unmodified as reported in FIG. 41. The amount of INT-1103 secreted in bile is approx. 30-40% of the administered dose and its secretion rate is relatively low and at the end of the collection period a relatively high amount of the molecule is still secreted into bile. The main hepatic metabolite of INT-1103 in rat at the administered dose is the 3-glucoronide as reported in FIG. 42. The amount of this compound has not be quantified since the pure reference standard is not available. Other metabolites are secreted into bile as reported in FIG. 43 and in more details in FIG. 43 and FIG. 44. The main identified metabolites is the 3-sulphate conjugate, an hydroxy analog (one more hydroxyl), keto derivatives and epimers of INT-1103. The exact amount of these compound were not quantified since the standards are not yet available.

These data suggest that INT-1103 can be secreted in bile as such and its behaviour is different from natural dihydroxy analogs such as CDCA and INT-747 that require a conjugation with taurine and glycine to be secreted into bile. This is a main requisite for molecules with this lipophilicity. On the contrary trihydrohy BA such as CA or UCA can be secreted in bile also partially as such. The sulphate group present in INT1103 facilitate the secretion process even if the molecule is still quite lipophilic and the behaviour is between an unconjugated and taurine conjugated bile acid. Moreover the liver strong metabolize this compound forming more hydrophilic compound such as 3-glucuronides, 3-sulphates and hydroxylated analogs. The extensive metabolism do to retained compound is related to the animal species and to the administered dose and according to these data we can speculate that this compound present a metabolism more similar to an "acids steroids" slightly different from a common bile acid, but may be sharing same properties. We do not know the metabolism in human but if its behaviour is more like a steroid is may be underwent to 3-glucuronidation even in humans. The compound was administered iv and addition data are required to evaluate the extent of its intestinal absorption ie passive or active like a taurine conjugate.

Example 13

In Vitro Metabolic Stability in Human Stools Culture

Stability to Intestinal Bacteria; 7α-Dehydroxylation

Figure 45:
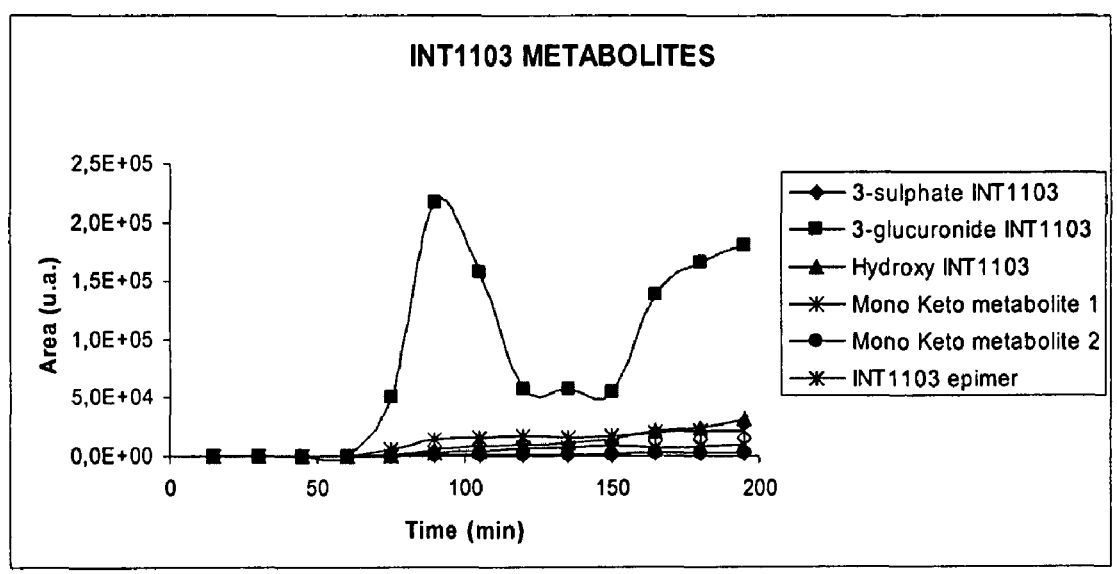
FIG. 45 shows the secretion rate of INT-1103 main metabolites identified in bile using mass spectrometry. Data are reported as concentration in bile and should be corrected by the bile volume.

Homogenized fresh human stools (500 mg) were transferred into sterile vials to which 5 mL of sterilized chopped meat-glucose medium (Scott Lab., Fiskville, R.I.) was added. BA were then added at a final concentration of 0.05 mM. Vials were incubated at 37 C; then, at 0, 4, 8, 16, 20, 24, and 72 h after the addition of the BA, the reaction was stopped with 150 L of 30% KOH. The samples were centrifuged at 3500 rpm for 10 min; from the supernatant the BA were isolated by C-18 solid-phase extraction and analyzed by TLC and HPLC-ES-MS/MS. Thin-layer chromatography (TLC), utilizing silica gel 0.25 m thickness plates (Merck, Darmstat, Germany), was employed as the first screening test. The solvent system used for the separation of conjugated BA was composed of propionic acid/isoamyl acetate/water/N-propanol (3:4:1:2, v/v/v/v; solvent I), and that of the unconjugated BA was acetic acid/carbon tetrachloride/isopropyl ether/isoamyl acetate/water/N-propanol/benzene (1:4:6:8:2:2, v/v/v/v/v/v; solvent II). Separated BA were revealed with 5% phosphomolybdic acid ethanol solution. Both INT-747 and INT-1103 are very stable when incubated in human stool cultures and even after 24 hour more than 85% of the compounds can be recovered unmodified as reported in FIG. 45. On the contrary the reference natural analogue CDCA present an half-life time of almost one hour and after 8 hours of incubation is almost completely metabolized (7-dehydroxylated) to form lithocholic acid.

Results

Figure 46:
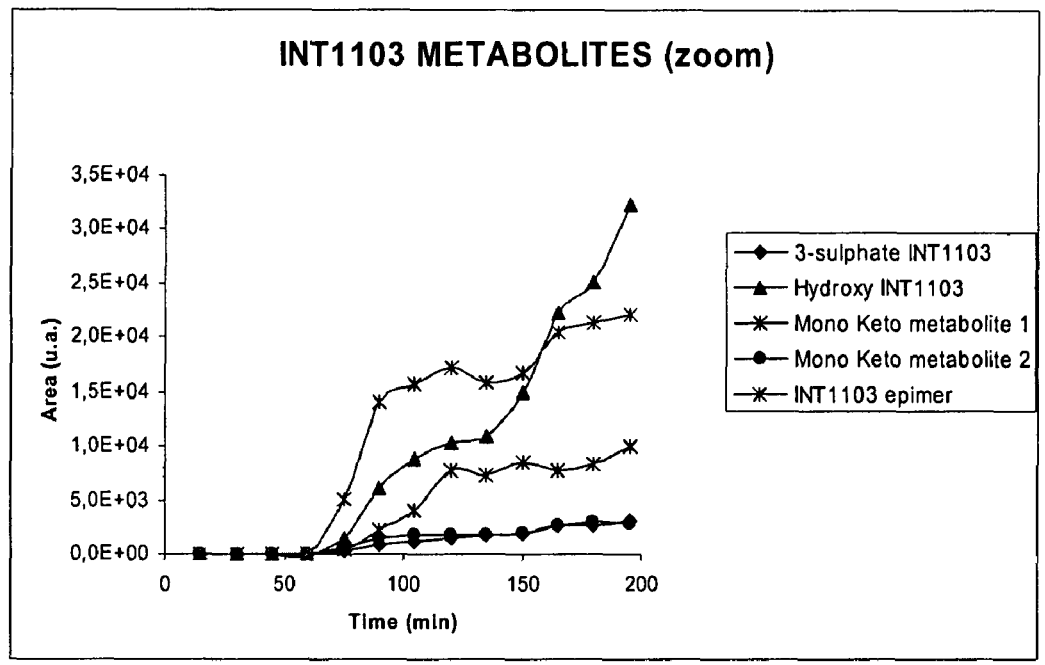
FIG. 46 shows the secretion rate of INT-1103 main metabolites identified in bile using mass spectrometry zoom display. Data are reported as concentration in bile and should be corrected by the bile volume.
Figure 47:
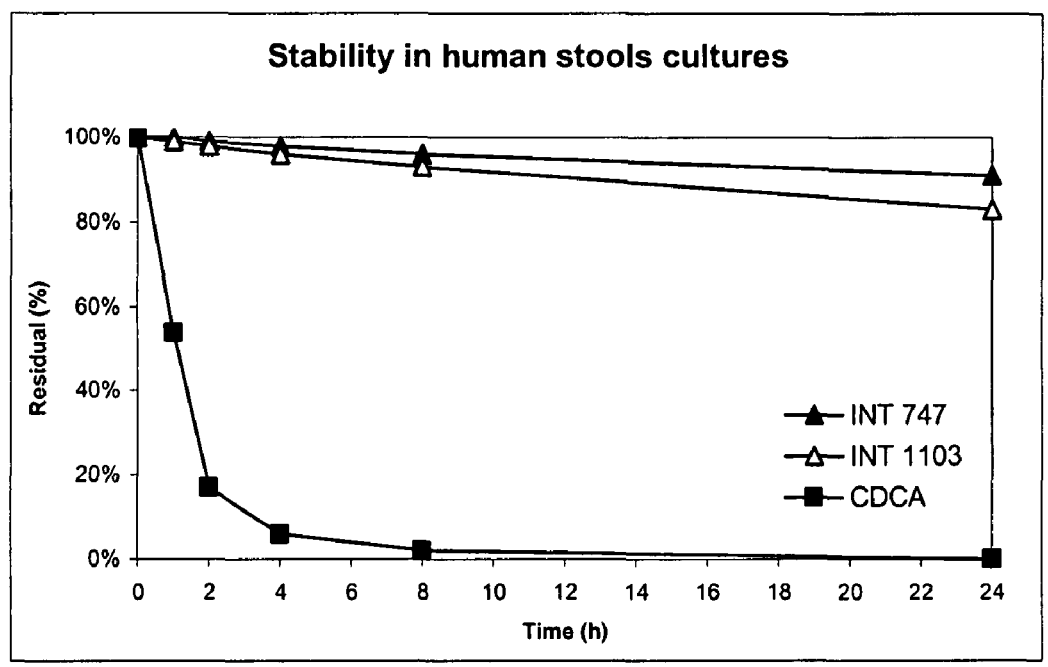
FIG. 47 shows the metabolic stability of INT-747 and INT-1103 in human stools cultures. Chenodeoxycholic was used as a reference natural analogue.
Figure 48:
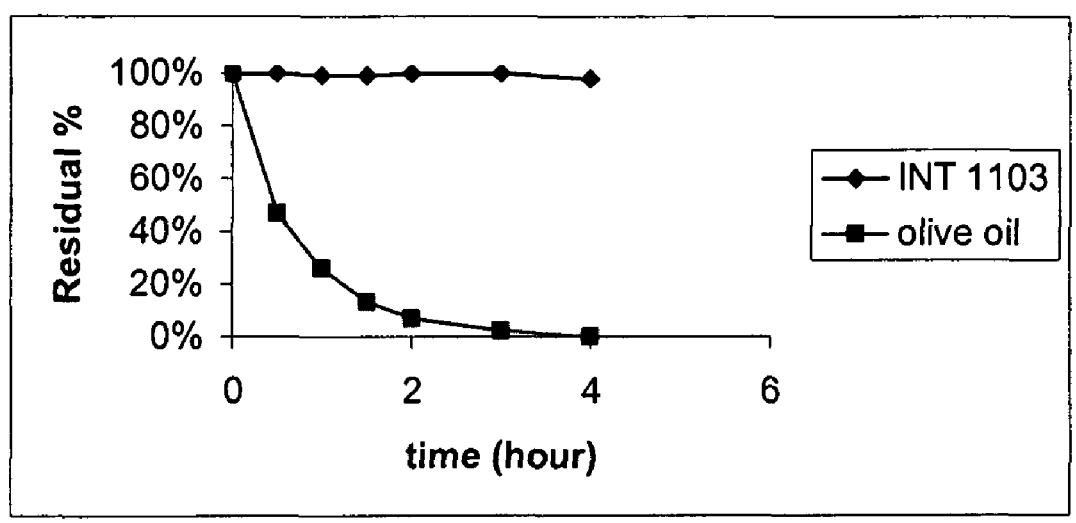
FIG. 48 shows the metabolic stability of INT-1103 in simulated pancreatic fluid. Olive oil was used as a reference as reported in the USP protocol. The compound is very stable and the ester bond (sulphate) is not hydrolyzed by pancreatic esterases, suggesting a high stability in human duodenal and upper intestine content.

These data, shown in FIG. 46, suggest that the presence of the ethyl group in the 6 position protect the 7 hydroxyl group toward oxidation or removal by steric hindrance. In addition both analogues are very stable and particularly INT-1103. The side chain ester bond is quite stable in the human stool culture. No minor metabolites have been found by HPLC-ES-MS/MS Example 14

In Vitro Metabolic Stability in Simulated Duodenal/Pancreatic Fluid (USP Specification)

Material and Methods

This study has been performed only for INT1103 since it contain an ester bond in the side chain and the aim was to verify the stability in presence of esterase enzymes like present in duodenal and pancreatic juice. Simulated pancreatic fluid was prepared by dissolving 10 g/L Pancreatin (Sigma P8096: pancreatin from porcine pancreas, activity 1×USP specifications) in 0.05M phosphate buffer, pH=7.2±0.1. Then, 4-mL aliquots of the simulated pancreatic fluid were added of 50 μM INT-1103 and incubated for different times (0, 30, 60, 90, 120, 180 and 240 min) at 37° C. After incubation, a 2-mL aliquot of each solution was added with 2 mL of 0.1M NaOH and subjected to bile acids extraction by SPE and analysis by thin-layer chromatography and mass spectrometry as described above.

The invention claimed is:

1. A compound of formula (I):

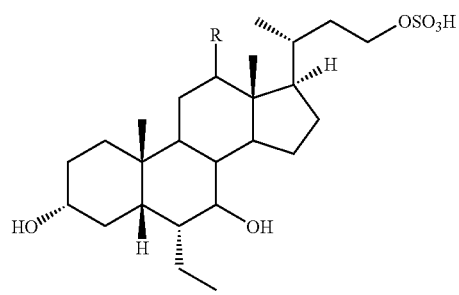

wherein R is hydrogen or alpha-hydroxy, the hydroxyl group in position 7 is in the alpha or beta position;

and pharmaceutically acceptable salts or amino acid conjugates thereof.

2. A compound of formula (I):

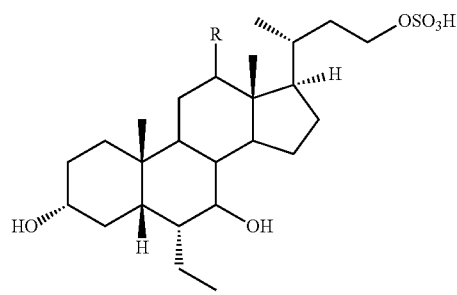

wherein the hydroxy group in position 7 is in the alpha position and R is hydrogen.

3. A compound of formula (I):

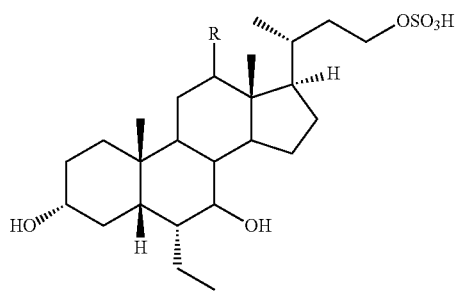

wherein the hydroxy group in position 7 is in the beta position and R is hydrogen.

4. A compound of formula (I):

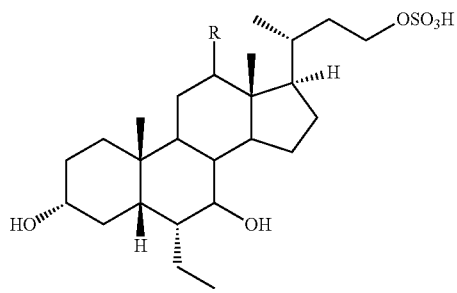

wherein the hydroxy group in position 7 is in the alpha position and R is alpha-hydroxy.

5. A compound of formula (I) according to claim 1 wherein the pharmaceutically acceptable salt is:

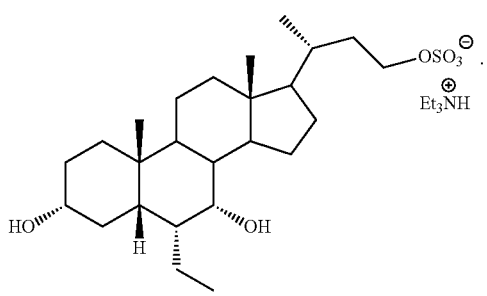

6. A compound of formula (I) according to claim 1 wherein the pharmaceutically acceptable salt is:

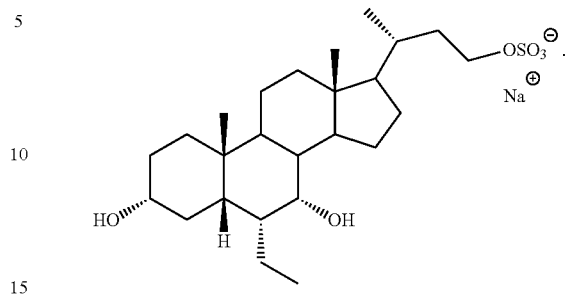

7. A method for the treatment of cholestasis in a mammal comprising administering to the mammal suffering from cholestasis a therapeutically effective amount of a compound of formula (I) according to any one of claims 1-4.

8. A pharmaceutical composition comprising a compound of formula (I) according to any one of claims 1-4 and a pharmaceutically acceptable carrier or diluent.

* * * * *

UNITED STATES PATENT AND TRADEMARK OFFICE
CERTIFICATE OF CORRECTION

PATENT NO. : 7,932,244 B2
APPLICATION NO. : 11/819517
DATED : April 26, 2011
INVENTOR(S) : Roberto Pellicciari et al.

It is certified that error appears in the above-identified patent and that said Letters Patent is hereby corrected as shown below:

Column 55, line 66 and column 56, lines 41 and 66, the term "hydroxy" should read --hydroxyl--.

Signed and Sealed this
Second Day of August, 2011

David J. Kappos
*Director of the United States Patent and Trademark Office*

SEQUENCE LISTING

<160> NUMBER OF SEQ ID NOS: 64

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gaaggtgaag gtcggagt                                               18

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
catgggtgga atcatattgg aa                                          22

<210> SEQ ID NO 3
<211> LENGTH: 20
<212> TYPE: DNA

```
<213> ORGANISM: Artificial Sequence
<220> FEATURE:
<223> OTHER INFORMATION: primer

<400> SEQUENCE: 3
caccttgagg acggttccta                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cgatccaaag ggcatgtagt                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gctgtctgga gtccttctgg                                               20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ccaatgatag ggcgaaagaa gag                                           23

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gggccattgt acgagatcct aa                                            22

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tgcaccgtct tttcactttc tg                                            22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gcaaggccat cgactacatt                                               20
```

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggtcagtgtg tcctccacct                                        20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
ctgagtatgt cgtggagtct ac                                     22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
gttggtggtg caggatgcat tg                                     22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aaatcggatg gtttgactgc                                        20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgacagcgag aatcaccaag                                        20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tctcttcttc cgccctatca                                        20

<210> SEQ ID NO 16
<211> LENGTH: 20
<212> TYPE: DNA
<213> ORGANISM: Artificial Sequence
<220> FEATURE:
<223> OTHER INFORMATION: primer

```
<400> SEQUENCE: 16
aagggcttgc tggacagtta                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aagccatgat gcaaaacctc                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gccggaaata cttggtcaaa                                               20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gatcaaagag gagccagtgc                                               20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tagatggtgg ctgctgagtg                                               20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
acggcatgga tctcaaagac                                               20

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
gtgggtgagc acgtagt                                                  17

<210> SEQ ID NO 23
<211> LENGTH: 20
<212> TYPE: DNA
```

-continued

<213> ORGANISM: Artificial Sequence
<220> FEATURE:
<223> OTHER INFORMATION: primer

<400> SEQUENCE: 23
tcacagcagc acatcaacaa                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tgtcctcatc ctcgaaggtc                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ccggagagga gacttcacag                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tccacgattt cccagagaac                                              20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gctttgcagc tcttcctcat                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gtcaccatcc ttttgccagt                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
acgagacgga taggcagaga                                              20

```
<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cacatgcaag gaagggaact                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ttgcttcagc tccacagaga                                              20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tggttgtaga gggcaaggac                                              20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
tgtgagggct gcaaaggttt                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
acatccccat ctctctgcac                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
atgactctac ccacggcaag                                              20

<210> SEQ ID NO 36
<211> LENGTH: 20
<212> TYPE: DNA
<213> ORGANISM: Artificial Sequence
<220> FEATURE:
<223> OTHER INFORMATION: primer
```

```
<400> SEQUENCE: 36
atgactctac ccacggcaag                                         20

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
cctggagcag ccctcgtctc ag                                      22

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
aacactgtat gcaaaccgag ga                                      22

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
aaggcaagaa ctcgagatac cag                                     23

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
tttcactttc aatgtccacc aac                                     23

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
ctgcagcgag ctttatccac                                         20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
cctgggttgc taagggactc                                         20

<210> SEQ ID NO 43
<211> LENGTH: 23
<212> TYPE: DNA
```

```
<213> ORGANISM: Artificial Sequence
<220> FEATURE:
<223> OTHER INFORMATION: primer

<400> SEQUENCE: 43
cccctatctc tcagtacaca tgg                                              23

<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
gaccataagg aggacaaagg tct                                              23

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
gcatgatgcc actcctctta tac                                              23

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
tacatagtgt ggccttttgg act                                              23

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
cgttgcctac atccaggttt                                                  20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gccattgcct gaaagaacat                                                  20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gttctcgctg gtcttcttgg                                                  20
```

```
<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
cgtctgtggc gagtcttgta                                                    20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
gatggatacc cgtttgatgg                                                    20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
tgaacaggaa ggggaacttg                                                    20

<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53
gaaggtgaag gtcggagt                                                      18

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
catgggtgga atcatattgg aa                                                 22

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
gctgtctgga gtccttctgg                                                    20

<210> SEQ ID NO 56
<211> LENGTH: 23
<212> TYPE: DNA
<213> ORGANISM: Artificial Sequence
<220> FEATURE:
<223> OTHER INFORMATION: primer
```

-continued

```
<400> SEQUENCE: 56
ccaatgatag ggcgaaagaa gag                                        23

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
gcaaggccat cgactacatt                                            20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
ggtcagtgtg tcctccacct                                            20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tgttggtgca cttcctaccc                                            20

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
ttgttccact tgtgggtcct                                            20

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
aagggcttgc tggacagtta                                            20

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
tctcttcttc ctccctatca                                            20

<210> SEQ ID NO 63
<211> LENGTH: 20
<212> TYPE: DNA
```

```
<213> ORGANISM: Artificial Sequence
<220> FEATURE:
<223> OTHER INFORMATION: primer

<400> SEQUENCE: 63
ccctgggtac tcttcaccaa                                               20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
gccaagtagg atgtgccaat                                               20
```